US011173207B2

(12) United States Patent
Baker, Jr. et al.

(10) Patent No.: US 11,173,207 B2
(45) Date of Patent: Nov. 16, 2021

(54) ADJUVANT COMPOSITIONS

(71) Applicants: The Regents of the University of Michigan, Ann Arbor, MI (US); NanoBio Corporation, Ann Arbor, MI (US)

(72) Inventors: James R. Baker, Jr., Ann Arbor, MI (US); Douglas M. Smith, Ann Arbor, MI (US); Susan Ciotti, Ann Arbor, MI (US)

(73) Assignees: THE REGENTS OF THE UNIVERSITY OF MICHIGAN, Ann Arbor, MI (US); NANOBIO CORPORATION, Ann Arbor, MI (US)

( * ) Notice: Subject to any disclaimer, the term of this patent is extended or adjusted under 35 U.S.C. 154(b) by 0 days.

(21) Appl. No.: 16/302,074

(22) PCT Filed: May 19, 2017

(86) PCT No.: PCT/US2017/033515
§ 371 (c)(1),
(2) Date: Nov. 15, 2018

(87) PCT Pub. No.: WO2017/201390
PCT Pub. Date: Nov. 23, 2017

(65) Prior Publication Data
US 2019/0282693 A1  Sep. 19, 2019

Related U.S. Application Data

(60) Provisional application No. 62/338,830, filed on May 19, 2016.

(51) Int. Cl.
*A61K 39/39* (2006.01)
*A61P 37/04* (2006.01)
*A61K 39/385* (2006.01)
*A61K 39/295* (2006.01)
*A61K 39/00* (2006.01)
*A61K 9/107* (2006.01)

(52) U.S. Cl.
CPC ............ *A61K 39/39* (2013.01); *A61K 9/1075* (2013.01); *A61K 39/295* (2013.01); *A61K 39/385* (2013.01); *A61P 37/04* (2018.01); *A61K 2039/55561* (2013.01); *A61K 2039/55566* (2013.01); *A61K 2039/55577* (2013.01)

(58) Field of Classification Search
None
See application file for complete search history.

(56) References Cited

U.S. PATENT DOCUMENTS

| 4,166,452 A | 9/1979 | Generales |
| 4,256,108 A | 3/1981 | Theeuwes |
| 4,265,874 A | 5/1981 | Bonsen et al. |
| 4,596,556 A | 6/1986 | Marrow et al. |
| 4,895,452 A | 1/1990 | Yiournas et al. |
| 5,057,540 A | 10/1991 | Kensil et al. |
| 5,103,497 A | 4/1992 | Hicks |
| 5,565,332 A | 10/1996 | Hoogenboom et al. |
| 5,993,412 A | 11/1999 | Deily et al. |
| 6,005,099 A | 12/1999 | Davies et al. |
| 6,015,832 A | 1/2000 | Baker et al. |
| 6,194,388 B1 | 2/2001 | Krieg et al. |
| 6,207,646 B1 | 3/2001 | Krieg et al. |
| 6,214,806 B1 | 4/2001 | Krieg et al. |
| 6,218,371 B1 | 4/2001 | Krieg et al. |
| 6,239,116 B1 | 5/2001 | Krieg et al. |
| 6,339,068 B1 | 1/2002 | Krieg et al. |
| 6,506,803 B1 | 1/2003 | Baker et al. |

(Continued)

FOREIGN PATENT DOCUMENTS

| EP | 0362279 | 4/1990 |
| EP | 0468520 | 1/1992 |

(Continued)

OTHER PUBLICATIONS

Parkins et al, PSTT Apr. 2000, 3/4:129-137. (Year: 2000).*
Akira, et al., Pathogen recognition and innate immunity. Cell. Feb. 24, 2006;124(4):783-801.
Audibert, F. M. et al. Adjuvants: current status, clinical perspectives and future prospects. Immunol Today. Jun. 1993;14(6):281-4.
Beg, A.A. Endogenous ligands of Toll-like receptors: implications for regulating inflammatory and immune responses. Trends Immunol. Nov. 2002;23(11):509-12.
Beutler et al., Genetic analysis of host resistance: Toll-like receptor signaling and immunity at large. Annu Rev Immunol. 2006;24:353-89.

(Continued)

*Primary Examiner* — Nita M. Minnifield
(74) *Attorney, Agent, or Firm* — Casimir Jones, S.C.

(57) ABSTRACT

The present invention provides methods and compositions for the stimulation of immune responses. In particular, the invention provides methods and compositions for enhancing an immune response to one or more antigens. Compositions and methods of the invention are useful for the treatment and/or prevention of microbial infections, such as infections caused by bacteria, viruses, fungi and parasites, as well as the treatment and/or prevention of cancer and malignant diseases. Compositions and methods of the invention include one or more antigens/immunogens together with an adjuvant formulation comprising an emulsion delivery system in combination with one or more immunostimulatory compounds (e.g., a compound that stimulates the innate immune system (e.g., a toll-like receptor antagonist (e.g., synthetic oligodeoxynucleotides (ODN)))) that enhance immune responses to the one or more antigens/immunogens when administered to a subject. Compositions and methods of the invention find use in, among other things, clinical (e.g. therapeutic and preventative medicine (e.g., vaccination)) and research applications.

4 Claims, 13 Drawing Sheets

(56) References Cited

U.S. PATENT DOCUMENTS

| | | | |
|---|---|---|---|
| 6,559,189 B2 | 5/2003 | Baker et al. | |
| 6,635,676 B2 | 10/2003 | Baker et al. | |
| 8,232,320 B2 * | 7/2012 | Baker, Jr. | A61K 8/062 |
| | | | 514/642 |
| 8,236,335 B2 * | 8/2012 | Baker, Jr. | A61K 8/062 |
| | | | 424/405 |
| 8,771,731 B2 * | 7/2014 | Baker, Jr. | A61K 9/1075 |
| | | | 424/455 |
| 8,877,208 B2 * | 11/2014 | Baker, Jr. | A61P 31/00 |
| | | | 424/203.1 |
| 8,962,026 B2 * | 2/2015 | Baker, Jr. | A61K 31/4425 |
| | | | 424/489 |
| 9,415,006 B2 * | 8/2016 | Baker, Jr. | A61K 39/292 |
| 9,801,842 B2 * | 10/2017 | Baker, Jr. | A61K 33/14 |
| 9,839,685 B2 * | 12/2017 | Baker, Jr. | A61K 39/12 |
| 9,974,844 B2 * | 5/2018 | Myc | A61K 31/00 |
| 10,138,279 B2 * | 11/2018 | Baker, Jr. | C07K 14/32 |
| 10,286,056 B2 * | 5/2019 | Brito | A61K 9/1075 |
| 10,369,205 B2 * | 8/2019 | Agrawal | A61K 39/12 |
| 10,525,121 B2 * | 1/2020 | Hamouda | A61K 39/39 |
| 2002/0045667 A1 | 4/2002 | Baker et al. | |
| 2003/0139364 A1 | 7/2003 | Krieg et al. | |
| 2004/0043041 A1 | 3/2004 | Baker et al. | |
| 2005/0208083 A1 | 9/2005 | Annis | |
| 2005/0238660 A1 | 10/2005 | Babiuk et al. | |
| 2005/0281843 A1 | 12/2005 | Singh et al. | |
| 2006/0251684 A1 | 11/2006 | Annis et al. | |
| 2007/0036831 A1 | 2/2007 | Baker | |
| 2009/0291095 A1 * | 11/2009 | Baker, Jr. | A61K 39/292 |
| | | | 424/184.1 |
| 2010/0203139 A1 * | 8/2010 | Baker, Jr. | A61K 31/14 |
| | | | 424/484 |
| 2012/0107349 A1 * | 5/2012 | Baker, Jr. | A61K 39/0291 |
| | | | 424/203.1 |
| 2012/0141526 A1 * | 6/2012 | Baker | A61P 37/00 |
| | | | 424/208.1 |
| 2014/0093537 A1 * | 4/2014 | Baker, Jr. | A61K 39/245 |
| | | | 424/209.1 |
| 2015/0017191 A1 | 1/2015 | Fox | |
| 2015/0266933 A1 * | 9/2015 | Baker, Jr. | C07K 14/32 |
| | | | 424/246.1 |
| 2016/0317637 A1 * | 11/2016 | Agrawal | A61P 35/00 |
| 2016/0368950 A1 * | 12/2016 | Fischer | A61P 31/04 |
| 2018/0071380 A1 * | 3/2018 | Makidon | A61K 47/44 |
| 2018/0296663 A1 * | 10/2018 | Hipp | A61K 39/12 |
| 2019/0022200 A1 * | 1/2019 | Myc | A61K 9/1075 |
| 2019/0282693 A1 * | 9/2019 | Baker, Jr. | A61K 39/385 |
| 2020/0054731 A1 * | 2/2020 | Agrawal | A61P 35/00 |

FOREIGN PATENT DOCUMENTS

| | | | |
|---|---|---|---|
| EP | 0517565 | 12/1992 | |
| EP | 0549074 | 6/1993 | |
| EP | 0689454 | 1/1996 | |
| EP | 0729473 | 9/1996 | |
| EP | 3454891 A1 * | 3/2019 | A61K 39/39 |
| WO | WO 199219265 | 12/1992 | |
| WO | WO 199303151 | 2/1993 | |
| WO | WO 199313202 | 8/1993 | |
| WO | WO 199400153 | 6/1994 | |
| WO | WO 199413804 | 6/1994 | |
| WO | WO 199517210 | 6/1995 | |
| WO | WO 199602555 | 1/1996 | |
| WO | WO 199611711 | 4/1996 | |
| WO | WO 199633739 | 10/1996 | |
| WO | WO 199748440 | 12/1997 | |
| WO | WO 199828037 | 2/1998 | |
| WO | WO 199816247 | 4/1998 | |
| WO | WO 199856414 | 12/1998 | |
| WO | WO 199912565 | 3/1999 | |
| WO | WO 199910008 | 4/1999 | |
| WO | WO 199927961 | 10/1999 | |
| WO | WO 199911241 | 11/1999 | |
| WO | WO 200122990 | 5/2001 | |
| WO | WO 2003015711 | 2/2003 | |
| WO | WO-2012003361 A2 * | 1/2012 | A61K 9/1075 |
| WO | WO-2017196979 A1 * | 11/2017 | A61K 39/39 |
| WO | WO-2017201390 A1 * | 11/2017 | A61K 39/39 |

OTHER PUBLICATIONS

Brazolot-Millan et al., CpG DNA can induce strong Th1 humoral and cell-mediated immune responses against hepatitis B surface antigen in young mice. Proc Natl Acad Sci U S A. Dec. 22, 1998;95(26):15553-8.

Cole et al., Human monoclonal antibodies. Mol Cell Biochem. Jun. 1984;62(2):109-20.

Coloma et al., Design and production of novel tetravalent bispecific antibodies. Nat Biotechnol. Feb. 1997;15(2):159-63.

Cote et al., Generation of human monoclonal antibodies reactive with cellular antigens. Proc Natl Acad Sci U S A. Apr. 1983;80(7):2026-30.

Davis et al., CpG DNA is a potent enhancer of specific immunity in mice immunized with recombinant hepatitis B surface antigen. J Immunol. Jan. 15, 1998;160(2):870-6.

Donovan et al., Prevention of murine influenza A virus pneumonitis by surfactant nano-emulsions. Antivir Chem Chemother. Jan. 2000;11(1):41-9.

Doyle et al., IRF3 mediates a TLR3/TLR4-specific antiviral gene program. Immunity. Sep. 2002;17(3):251-63.

Flohe, et al. Human heat shock protein 60 induces maturation of dendritic cells versus a Th1-promoting phenotype. J Immunol. Mar. 1, 2003;170(5):2340-8.

Hamouda et al., A novel surfactant nanoemulsion with broad-spectrum sporicidal activity against *Bacillus* species. J Infect Dis. Dec. 1999;180(6):1939-49.

Hamouda et al., Antimicrobial mechanism of action of surfactant lipid preparations in enteric Gram-negative bacilli. J Appl Microbiol. Sep. 2000;89(3):397-403.

Hilgers et al., Synergistic effects of synthetic adjuvants on the humoral immune response. Int Arch Allergy Appl Immunol. 1986;79(4):392-6.

Hilgers et al., Synthetic sulpholipopolysaccharides: novel adjuvants for humoral immune responses. Immunology. Jan. 1987;60(1):141-6.

Hogenesch, H. Mechanisms of stimulation of the immune response by aluminum adjuvants. Vaccine. May 31, 2002;20 Suppl 3:S34-9.

Illum et al. Hyaluronic acid ester microspheres as a nasal delivery system for insulin. J Controlled Rel., 1994, 29:133-141.

Janeway et al., Innate immune recognition. Annu Rev Immunol. 2002;20:197-216. Epub Oct. 4, 2001.

Janeway, et al. in Immunobiology, "The Immune System in Health and Disease," Second Edition, Current Biology Ltd., London, Great Britain (1996). Book: Table of Contents Provided.

Jones et al., Different Toll-like receptor agonists induce distinct macrophage responses. J Leukoc Biol. Jun. 2001;69(6):1036-44.

Kaluza et al., A general method for chimerization of monoclonal antibodies by inverse polymerase chain reaction which conserves authentic N-terminal sequences. Gene. Dec. 15, 1992;122(2):321-8.

Kang, A.S. et al. Antibody redesign by chain shuffling from random combinatorial immunoglobulin libraries. Proc Natl Acad Sci U S A. Dec. 15, 1991;88(24):11120-3.

Kensil et al. Separation and characterization of saponins with adjuvant activity from Quillaja saponaria Molina cortex. J Immunol. Jan. 15, 1991;146(2):431-7.

Kensil, Saponins as vaccine adjuvants. Crit Rev Ther Drug Carrier Syst. 1996;13(1-2):1-55.

Kohler et al., Continuous cultures of fused cells secreting antibody of predefined specificity. Nature. Aug. 7, 1975;256(5517):495-7.

Kozbor et al., J. Immunol. Methods 81, 3142, 1985.

Lacaille-Dubois et al. A review of the biological and pharmacological activities of saponins. Phytomedicine. Mar. 1996;2(4):363-86.

Lemaitre et al., Pillars article: the dorsoventral regulatory gene cassette spätzle/Toll/cactus controls the potent antifungal response in *Drosophila* adults. Cell. 1996. 86: 973-983. J Immunol. Jun. 1, 2012;188(11):5210-20.

(56) References Cited

OTHER PUBLICATIONS

Mallender et al., Construction, expression, and activity of a bivalent bispecific single-chain antibody. J Biol Chem. Jan. 7, 1994;269(1):199-206.

Martin, Remington's Pharmaceutical Sciences, 15th Ed., Mack Publ. Co., Easton, Pa. (1975).

McCluskie et al., CpG DNA is a potent enhancer of systemic and mucosal immune responses against hepatitis B surface antigen with intranasal administration to mice.J Immunol. Nov. 1, 1998;161(9):4463-6.

McCutcheon's vol. 1: Emulsifiers and Detergents North American Edition, 1996. Table of Contents Only.

Meyers, Surfactant Science and Technology, VCH Publishers Inc., New York, pp. 231-245 (1992).

Misch, E.A. et al. Toll-like receptor polymorphisms and susceptibility to human disease. Clin Sci (Lond). Mar. 2008;114(5):347-60.

Morrison et al., Chimeric human antibody molecules: mouse antigen-binding domains with human constant region domains. Proc Natl Acad Sci U S A. Nov. 1984;81(21):6851-5.

Neuberger et al., Recombinant antibodies possessing novel effector functions. Nature. Dec. 13-19, 1984;312(5995):604-8.

Nicholls et al., An improved method for generating single-chain antibodies from hybridomas. J Immunol Methods. Sep. 27, 1993;165(1):81-91.

Ozinsky et al., The repertoire for pattern recognition of pathogens by the innate immune system is defined by cooperation between toll-like receptors. Proc Natl Acad Sci U S A. Dec. 5, 2000;97(25):13766-71.

Remington: The Science and Practice of Pharmacy, Mack Publishing Company, Easton, Pa., 19th edition, 1995, pp. 1402-1403.

Tadros, T., Applied Surfactants: Principles and Applications (Copyright Aug. 2005 WILEY-VCH Verlag GmbH & Co. KGaA, Weinheim ISBN: 3-527-30629-3) Table of Contents Only.

Takeda et al., Construction of chimaeric processed immunoglobulin genes containing mouse variable and human constant region sequences. Nature. Apr. 4-10, 1985;314(6010):452-4.

Takeda et al., Toll-like receptors. Annu Rev Immunol. 2003;21:335-76.

Thirion et al., Mono- and bispecific single-chain antibody fragments for cancer therapy. Eur J Cancer Prev. Dec. 1996;5(6):507-11.

Triantafilou et al., Lipopolysaccharide recognition: CD14, TLRs and the LPS-activation cluster. Trends Immunol. Jun. 2002;23(6):301-4.

Verhaar et al., A single chain Fv derived from a filamentous phage library has distinct tumor targeting advantages over one derived from a hybridoma. Int J Cancer. May 16, 1995;61(4):497-501.

Wang et al. Decellularized liver scaffolds effectively support the proliferation and differentiation of mouse fetal hepatic progenitors. J Biomed Mater Res A. Apr. 2014;102(4):1017-25.

Winter et al., Man-made antibodies. Nature. Jan. 24, 1991;349(6307):293-9.

Yamamoto et al., Essential role for TIRAP in activation of the signalling cascade shared by TLR2 and TLR4. Nature. Nov. 21, 2002;420(6913):324-9.

International Search Report and Written Opinion, International Patent Application No. PCT/US2017/033515, dated Aug. 17, 2017, 13 pages.

\* cited by examiner

A. rH5-specific IgG

B. HAI

FIG. 13

W₈₀5EC + CpG

| | D3 Group 1 5% W₈₀5EC 20μg CpG rH5 (200μg/ml) | D14 Group 1 5% W805EC 20μg CpG H5 (200μg/ml) |
|---|---|---|
| 1:1 (64μg/ml) | | |
| 1:1.5 (42.67μg/ml) | | |
| 1:2 (32μg/ml) | | |
| 1:4 (16μg/ml) | | |
| Test Average (μg/ml): 200μg/mL reference (Fresh) | 217.5 | |

DODAC + CpG

| | D3 Group 2 5% DODAC 20μg CpG H5 (200μg/ml) | D14 Group 2 5% DODAC 20μg CpG H5 (200μg/ml) |
|---|---|---|
| Test Average: | | 205.7 |

DODAC

| | D3 Group 3 5% DODAC H5 (200μg/ml) | D14 Group 3 5% DODAC H5 (200μg/ml) |
|---|---|---|
| 1:1 (64μg/ml) | | |
| 1:1.5 (42.67μg/ml) | | |
| 1:2 (32μg/ml) | | |
| 1:4 (16μg/ml) | | |
| Test Average (μg/ml): 200μg/mL reference (Fresh) | 204.9 | |

CpG

| | D3 Group 4 20μg CpG H5 (200μg/ml) | D14 Group 4 20μg CpG H5 (200μg/ml) |
|---|---|---|
| Test Average: | | 244.1 |

…

ADJUVANT COMPOSITIONS

FIELD OF THE INVENTION

The present invention provides methods and compositions for the stimulation of immune responses. In particular, the invention provides methods and compositions for enhancing an immune response to one or more antigens. Compositions and methods of the invention are useful for the treatment and/or prevention of microbial infections, such as infections caused by bacteria, viruses, fungi and parasites. Compositions and methods of the invention include one or more antigens/immunogens together with an adjuvant formulation comprising an emulsion delivery system in combination with one or more immunostimulatory compounds (e.g., a compound that stimulates the innate immune system (e.g., a toll-like receptor antagonist (e.g., synthetic oligodeoxynucleotides (ODN)))) that enhance immune responses to the one or more antigens/immunogens when administered to a subject. Compositions and methods of the invention find use in, among other things, clinical (e.g. therapeutic and preventative medicine (e.g., vaccination)) and research applications.

BACKGROUND

The body's immune system activates a variety of mechanisms for attacking pathogens (See, e.g., Janeway, Jr, C A. and Travers P., eds., in Immunobiology, "The Immune System in Health and Disease," Second Edition, Current Biology Ltd., London, Great Britain (1996)). However, not all of these mechanisms are necessarily activated after immunization. Protective immunity induced by immunization is dependent upon the capacity of an immunogenic composition to elicit the appropriate immune response to resist or eliminate the pathogen. Depending on the pathogen, cell-mediated and/or humoral immune responses are important for pathogen neutralization and/or elimination.

Many antigens are poorly immunogenic or non-immunogenic when administered by themselves. Strong adaptive immune responses to antigens generally require that the antigens be administered together with an adjuvant, a substance that enhances the immune response (See, e.g., Audbert, F. M. and Lise, L. D. 1993 Immunology Today, 14: 281-284).

Killed or subunit vaccines are often poorly immunogenic, and can result in weak and transient T-cell responses, thus requiring adjuvants to boost the immune response. However, many currently available vaccines include adjuvants that are suboptimal with respect to the quality and magnitude of immune responses they induce. For example, alum, the only approved adjuvant for use in humans in the United States, induces relatively good Th2 type immune responses but is not a potent adjuvant for Th1-type immune responses (See, e.g., HogenEsch et al., Vaccine (2002) 20 Suppl 13:S34-39). Thus, there is a need for additional effective and safer adjuvants.

Two broad categories of adjuvants exist-adjuvant delivery systems and immunostimulatory compounds/adjuvants. Delivery systems include particulate formulations such as microparticles, liposomes and emulsions. The mechanism of action of these systems are not fully understood but are thought to involve increased uptake by antigen presenting cells (APC) and/or formation of a depot at the site of injection. Immunostimulatory adjuvants stimulate innate immunity resulting in the secretion of cytokines and upregulation of costimulatory molecules. These events are now known to play an instructional role in the development of adaptive immune responses.

A major impediment in the development of novel vaccines has been the lack of safe yet effective vaccine adjuvants. In recent years, synthetic oligodeoxynucleotides containing CpG motifs (CpG) have gained considerable interest as vaccine adjuvants owing to their inherent ability to induce and enhance Th1-type immunity. Through their direct interaction with Toll-like receptor 9 (TLR9) on human B cells and dendritic cells (DC), as well as indirect effects on other immune cells such as monocytes, macrophages, and T cells, CpG enhance antigen presentation and induce the production of high levels of Th1 cytokines, resulting in the production of potent antigen-specific Th1-type immune responses. CpG have been shown to enhance both humoral and cellular immunity in multiple species including humans. QS-21 is a triterpene glycoside "saponin" isolated from the bark of the *Quillaja saponaria* Molina tree, a species native to South America. The bark of this tree, particularly the saponin fraction present in the bark, has long been known as a source of immune stimulators that can be used as vaccine adjuvants. Espinet (1951) noted the adjuvant activity of plant saponins to enhance the potency of foot-and-mouth disease vaccines. Unlike most other immunostimulators, QS-21 is water-soluble and has been shown to stimulate both humoral and cell-mediated Th1 and CTL responses to subunit antigens. (See Dalsgaard 1974).

SUMMARY OF THE INVENTION

The present invention provides methods and compositions for the stimulation of immune responses. In particular, the invention provides methods and compositions for enhancing an immune response to one or more antigens. Compositions and methods of the invention are useful for the treatment and/or prevention of microbial infections, such as infections caused by bacteria, viruses, fungi and parasites. Compositions and methods of the invention include one or more antigens/immunogens together with an adjuvant formulation comprising an emulsion delivery system in combination with one or more immunostimulatory compounds (e.g., a compound that stimulates the innate immune system (e.g., a toll-like receptor antagonist (e.g., synthetic oligodeoxynucleotides (ODN)))) that enhance immune responses to the one or more antigens/immunogens when administered to a subject. Compositions and methods of the invention find use in, among other things, clinical (e.g. therapeutic and preventative medicine (e.g., vaccination)) and research applications.

Accordingly, the present invention provides improved adjuvant compositions. In one embodiment, the invention provides an adjuvant formulation for modulating an immune response (e.g., enhancing an immune response (e.g., synergistically enhancing an immune response) to an antigen administered to a subject, the composition comprising: (a) a nanoemulsion adjuvant; and (b) at least one immunostimulatory compound (e.g., a compound that stimulates the innate immune system (e.g., a toll-like receptor antagonist (e.g., synthetic oligodeoxynucleotides (ODN))). The adjuvant formulation provided herein exhibit a surprisingly unexpected adjuvanting effect on an antigen which is greater than the adjuvanting effect attainable by one of the constituents of the adjuvant formulation alone. For example, in one embodiment, an immune response induced in a subject when an immunogenic compositions of the invention comprising one or more antigens/immunogens together with an adjuvant formulation comprising an emulsion in combination with one or more immunostimulatory compounds is administered to a subject may be additive or synergistic (e.g., synergistic compared to when the one or more antigens/immunogens are administered with only the emulsion (e.g., a nanoemulsion described herein); or when the one or more antigens/immunogens are administered with only the immunostimulatory compound (e.g., a compound that stimulates the innate immune system (e.g., a toll-like receptor antagonist (e.g., synthetic oligodeoxynucleotides (ODN)))).

The adjuvant formulation is not limited by the type of nanoemulsion utilized. Indeed, a variety of nanoemulsions find use in an adjuvant formulation including, but not limited to, those nanoemulsions described herein. Similarly, the present invention is not limited to any particular immunostimulatory compound. Indeed, any immunostimulatory compound described herein finds use in an adjuvant formulation (e.g., for use in an immunogenic composition) of the invention. In a preferred embodiment, the immunostimulatory compound is a compound that stimulates the innate immune system (e.g., a toll-like receptor antagonist (TLR) (e.g., synthetic oligodeoxynucleotides (ODN)))). However, the invention is not limited to these immunostimulatory compounds. For example, in some embodiments, an immunostimulatory compound (e.g., for use in combination with a nanoemulsion in an adjuvant formulation of the invention) includes, but is not limited to, a TLR antagonist (e.g., a polyinosinic-polycytidylic acid (poly (IC)) (e.g., that activates TLR3); Pam3CSK4 (e.g., that activates TLR1/2); FSL-1 and/or MALP2 (e.g., that activate TLR2/6); monophosphoryl lipid A, (MPL) (e.g., that activate TLR4); flagellin (e.g., that activate TLR5); imiquimod (e.g., that activate TLR7); a Class B CpG phosphorothioate oligodeoxynucleotide, (CpG ODN) (e.g., that activate TLR9); a multi-pattern recognition receptors (multi-PRR ligand) (e.g., that act as agonists for dual or multiple TLR receptors and other PRRs)); a RIG-I-like receptor agonist (e.g., 5'ppp dsRNA and/or Poly(I:C)/LyoVec complexes); NOD and NOD-like receptor ligand agonists; inflammasome inducers (e.g., alum, alum salts, and/or alum crystals, chitosan, etc.); cytosolic DNA Sensors (CDS) and STING Ligands; immune cell receptors (e.g., CD40L, FMS-like tyrosine kinase ligand (e.g., Flt3 ligand), and multimeric immune cell receptors); Cytokines and chemokines (e.g., IL-1, IL-6, TGF-$\beta$, IL-12, IL-15, interferons ($\alpha$, $\beta$, $\gamma$, $\delta$), GM-CSF and others); synthetic glycolipids (e.g., alpha-galactosylceramide); and/or vitamins (e.g., retinoic acid).

In another embodiment, the invention provides an immunogenic composition for eliciting an immune response in a subject, including a human, the composition comprising: (a) one or more antigens; (b) a nanoemulsion; and (c) at least one immunostimulatory compound.

In another embodiment, the invention provides a method of modulating an immune response (e.g., enhancing an immune response) to an antigen comprising combining the antigen with the adjuvant formulation of the present invention and administering the same to a subject (e.g., administering an effective amount to generate a desired immune response in a subject). The invention is not limited by the type of antigen combined with an adjuvant formulation of the invention. Antigens include, but are not limited to, an inactivated microbial pathogen, an isolated and/or recombinant peptide, an isolated and/or recombinant protein, a glycoprotein, a lipoprotein, a glycopeptide, a lipopeptide, a toxoid, a carbohydrate, and/or a tumor-specific antigen. In some embodiments, an immunogenic composition of the invention is formulated to comprise between 0.1 and 500 µg of a protein antigen (e.g., derived or isolated from a pathogen and/or a recombinant form of an immunogenic pathogen component). However, the present invention is not limited to this amount of protein antigen (e.g., in some embodiments, more than 500 µg of protein antigen is used, and in other embodiments, less than 0.1 µg of protein antigen is used). Mixtures of two or more antigens may be employed. In a preferred embodiment, the peptides, glycopeptides or lipopeptides include an amino acid sequence corresponding to an antigenic determinant of a microbial pathogen that is known in the art. In one embodiment, the protein is influenza hemagglutinin.

In another embodiment, the invention provides a method of generating an immune response in a subject, including a human, comprising administering thereto an immunogenic composition of the present invention (e.g., comprising one or more antigens/immunogens together with an adjuvant formulation comprising an emulsion in combination with one or more immunostimulatory compounds). The invention is not limited by the type of immune response generated and refers to any type of immune response, including, but not limited to, innate immune responses (e.g., activation of Toll receptor signaling cascade), cell-mediated immune responses (e.g., responses mediated by T cells (e.g., antigen-specific T cells) and non-specific cells of the immune system), and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response). Immune responses include, but are not limited to, detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, B cell activation (e.g., antibody generation and/or secretion), binding of an immunogen (e.g., antigen (e.g., immunogenic polypeptide)) to an MHC molecule and inducing a cytotoxic T lymphocyte ("CTL") response, inducing a B cell response (e.g., antibody production), T-helper lymphocyte response, a delayed type hypersensitivity (DTH) response against antigen (e.g., from which an immunogenic polypeptide is derived), expansion (e.g., growth of a population of cells) of cells of the immune system (e.g., T cells, B cells (e.g., of any stage of development (e.g., plasma cells), and/or increased processing and presentation of antigen by antigen presenting cells.

In another embodiment, the invention provides a kit for preparing an immunogenic composition, comprising: (a) means for containing a nanoemulsion; (b) means for containing one or more immunostimulatory compounds; (c) means for containing at least one antigen; and (d) means for combining the nanoemulsion, one or more immunostimulatory compounds and at least one antigen to produce the immunogenic composition.

BRIEF DESCRIPTION OF THE FIGURES

The following figures form part of the present specification and are included to further demonstrate certain aspects and embodiments of the present invention. The invention may be better understood by reference to one or more of these figures in combination with the description of specific embodiments presented herein.

FIG. 13 shows the evaluation of rH5 antigen concentration by SRID analysis for NE+CpG ODN combination vaccines after storage at 5° C. The concentration of rH5 was calculated after measurement of well-diameters.

DEFINITIONS

Figure 1:
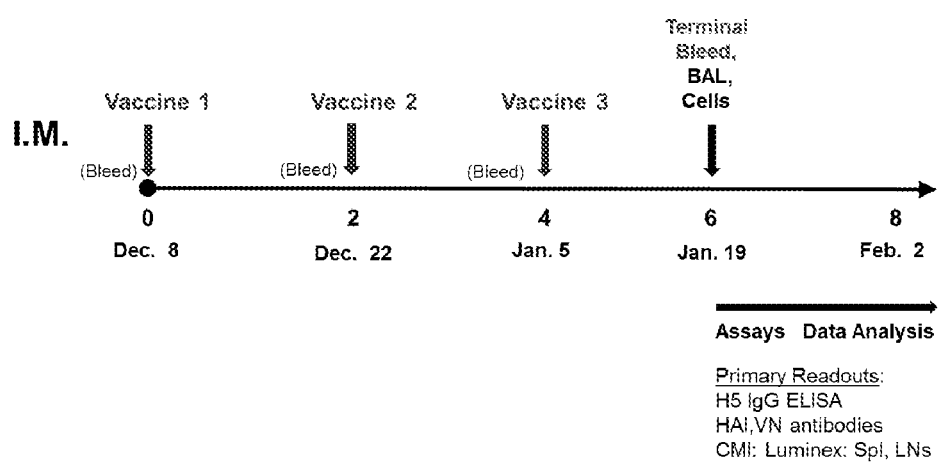
FIG. 1 shows the vaccination timeline for evaluation of nanoemulsion adjuvant in combination with QS21 or CpG ODN or using nanoemulsion adjuvants formulated with DODAC cationic surfactant by the intramuscular route in CD-1 mice in one embodiment of the invention.

To facilitate an understanding of the present invention, a number of terms and phrases are defined below.

As used herein, the term "microorganism" refers to any species or type of microorganism, including but not limited to, bacteria, viruses, archaea, fungi, protozoans, *Mycoplasma*, prions, and parasitic organisms. The term microorganism encompasses both those organisms that are in and of themselves pathogenic to another organism (e.g., animals, including humans, and plants) and those organisms that produce agents that are pathogenic to another organism, while the organism itself is not directly pathogenic or infective to the other organism.

As used herein the term "pathogen," and grammatical equivalents, refers to an organism (e.g., biological agent), including microorganisms, that causes a disease state (e.g., infection, pathologic condition, disease, etc.) in another organism (e.g., animals and plants) by directly infecting the other organism, or by producing agents that causes disease in another organism (e.g., bacteria that produce pathogenic toxins and the like). "Pathogens" include, but are not limited to, viruses, bacteria, archaea, fungi, protozoans, *Mycoplasma*, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc.

As used herein, the term "fungi" is used in reference to eukaryotic organisms such as molds and yeasts, including dimorphic fungi.

As used herein the terms "disease" and "pathologic condition" are used interchangeably, unless indicated otherwise herein, to describe a deviation from the condition regarded as normal or average for members of a species or group (e.g., humans), and which is detrimental to an affected individual under conditions that are not inimical to the majority of individuals of that species or group. Such a deviation can manifest as a state, signs, and/or symptoms (e.g., diarrhea, nausea, fever, pain, blisters, boils, rash, hyper-immune responses, hyper-sensitivity, immune suppression, inflammation, etc.) that are associated with any impairment of the normal state of a subject or of any of its organs or tissues that interrupts or modifies the performance of normal functions. A disease or pathological condition may be caused by or result from contact with a microorganism (e.g., a pathogen or other infective agent (e.g., a virus or bacteria)), may be responsive to environmental factors (e.g., allergens, malnutrition, industrial hazards, and/or climate), may be responsive to an inherent defect of the organism (e.g., genetic anomalies) or to combinations of these and other factors.

The terms "host" or "subject," as used herein, refer to an individual to be treated by (e.g., administered (e.g., injectably administered)) compositions and methods of the present invention. Subjects include, but are not limited to, mammals (e.g., murines, simians, equines, bovines, porcines, canines, felines, and the like), and most preferably includes humans. In the context of the invention, the term "subject" generally refers to an individual who will be administered (e.g., injectably administered) or who has been administered one or more compositions of the present invention (e.g., an injectable composition for inducing an immune response comprising a select nanoemulsion formulated for injection and one or more antigens).

As used herein, the terms "inactivating," "inactivation" and grammatical equivalents, when used in reference to a microorganism (e.g., a pathogen (e.g., a bacterium or a virus)), refer to the killing, elimination, neutralization and/or reducing of the capacity of the microorganism (e.g., a pathogen (e.g., a bacterium or a virus)) to infect and/or cause a pathological response and/or disease in a host.

As used herein, the term "fusigenic" is intended to refer to an emulsion that is capable of fusing with the membrane of a microbial agent (e.g., a bacterium or bacterial spore). Specific examples of fusigenic emulsions are described herein.

As used herein, the term "lysogenic" refers to an emulsion (e.g., a nanoemulsion) that is capable of disrupting the membrane of a microbial agent (e.g., a virus (e.g., viral envelope) or a bacterium or bacterial spore). In preferred embodiments of the present invention, the presence of a lysogenic and a fusigenic agent in the same composition produces an enhanced inactivating effect compared to either agent alone. Methods and compositions (e.g., for inducing an immune response (e.g., used as a vaccine) using this improved antimicrobial composition are described in detail herein.

The term "emulsion," as used herein, includes classic oil-in-water or water in oil dispersions or droplets, as well as other lipid structures that can form as a result of hydrophobic forces that drive apolar residues (e.g., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. Similarly, the term "nanoemulsion," as used herein, refers to oil-in-water dispersions comprising small lipid structures. For example, in some embodiments, the nanoemulsions comprise an oil phase having droplets with a mean particle size of approximately 0.1 to 5 microns (e.g., about 100, 150, 200, 250, 300, 350, 400, 450, 500 nm or larger in diameter), although smaller and larger particle sizes are contemplated. The terms "emulsion" and "nanoemulsion" and "NE" are often used herein, interchangeably, to refer to the nanoemulsions of the present invention.

As used herein, the terms "contact," "contacted," "expose," and "exposed," when used in reference to a nanoemulsion and a live microorganism, refer to bringing one or more nanoemulsions into contact with a microorganism (e.g., a pathogen) such that the nanoemulsion inactivates the microorganism or pathogenic agent, if present. The present invention is not limited by the amount or type of nanoemulsion used for microorganism inactivation. A variety of nanoemulsion that find use in the present invention are described herein and elsewhere (e.g., nanoemulsions described in U.S. Pat. Apps. 20020045667 and 20040043041, and U.S. Pat. Nos. 6,015,832, 6,506,803, 6,635,676, and 6,559,189, each of which is incorporated herein by reference in its entirety for all purposes). Ratios and amounts of nanoemulsion (e.g., sufficient for inactivating the microorganism (e.g., virus inactivation)) and microorganisms (e.g., sufficient to provide an antigenic composition (e.g., a composition capable of inducing an immune response)) are contemplated in the present invention including, but not limited to, those described herein.

The term "surfactant" refers to any molecule having both a polar head group, which energetically prefers solvation by water, and a hydrophobic tail that is not well solvated by water. The term "cationic surfactant" refers to a surfactant with a cationic head group. The term "cationic lipid" refers to a positively charged molecule comprising a positively charged head group and one or more (e.g., two, three or more) hydrocarbon chains. The term "anionic surfactant" refers to a surfactant with an anionic head group. When a single surfactant molecule exhibit both anionic and cationic dissociations it is called amphoteric or zwitterionic. For example, this is the case of synthetic products like betaines or sulfobetaines and natural substances such as aminoacids and phospholipids. Polymeric surfactants and surface active polymers result from the association of one or several macromolecular structures exhibiting hydrophilic and lipophilic characters, either as separated blocks or as grafts.

The terms "Hydrophile-Lipophile Balance Index Number" and "HLB Index Number" refer to an index for correlating the chemical structure of surfactant molecules with their surface activity. The HLB Index Number may be calculated by a variety of empirical formulas as described, for example, by Meyers, (See, e.g., Meyers, Surfactant Science and Technology, VCH Publishers Inc., New York, pp. 231-245 (1992)), incorporated herein by reference. As used herein where appropriate, the HLB Index Number of a surfactant is the HLB Index Number assigned to that surfactant in McCutcheon's Volume 1: Emulsifiers and Detergents North American Edition, 1996 (incorporated herein by reference). The HLB Index Number ranges from 0 to about 70 or more for commercial surfactants. Hydrophilic surfactants with high solubility in water and solubilizing properties are at the high end of the scale, while surfactants with low solubility in water that are good solubilizers of water in oils are at the low end of the scale.

As used herein the term "interaction enhancers" refers to compounds that act to enhance the interaction of an emulsion with a microorganism (e.g., with a cell wall of a bacteria (e.g., a Gram negative bacteria) or with a viral envelope (e.g., Vaccinia virus envelope)). Contemplated interaction enhancers include, but are not limited to, chelating agents (e.g., ethylenediaminetetraacetic acid (EDTA), ethylenebis (oxyethylenenitrilo)tetraacetic acid (EGTA), and the like) and certain biological agents (e.g., bovine serum albumin (BSA) and the like).

The terms "buffer" or "buffering agents" refer to materials, that when added to a solution, cause the solution to resist changes in pH.

The terms "reducing agent" and "electron donor" refer to a material that donates electrons to a second material to reduce the oxidation state of one or more of the second material's atoms.

The term "monovalent salt" refers to any salt in which the metal (e.g., Na, K, or Li) has a net 1+ charge in solution (i.e., one more proton than electron).

The term "divalent salt" refers to any salt in which a metal (e.g., Mg, Ca, or Sr) has a net 2+ charge in solution.

The terms "chelator" or "chelating agent" refer to any materials having more than one atom with a lone pair of electrons that are available to bond to a metal ion.

The term "solution" refers to an aqueous or non-aqueous mixture.

As used herein, the term "a composition for inducing an immune response" refers to a composition that, once administered to a subject (e.g., once, twice, three times or more (e.g., separated by weeks, months or years)), stimulates, generates and/or elicits an immune response in the subject (e.g., resulting in total or partial immunity to a microorganism (e.g., pathogen) capable of causing disease). In preferred embodiments of the invention, the composition comprises one or more antigens/immunogens together with an adjuvant formulation comprising an emulsion delivery system in combination with one or more immunostimulatory compounds (e.g., a compound that stimulates the innate immune system (e.g., a toll-like receptor antagonist (e.g., synthetic oligodeoxynucleotides (ODN) (e.g., ODN containing immunostimulatory CpG motifs (CpG))) or a saponin (e.g., a triterpene glycoside saponin (e.g., QS-21))) formulated for administration (e.g., via injectable route (e.g., intradermal, intramuscular, subcutaneously, etc.), mucosal route (e.g., nasally or vaginally), or other route) to a subject. In further preferred embodiments, the immunogenic composition comprises one or more other compounds or agents including, but not limited to, therapeutic agents, physiologically tolerable liquids, gels, carriers, diluents, adjuvants, excipients, salicylates, steroids, immunosuppressants, immunostimulants, antibodies, cytokines, antibiotics, binders, fillers, preservatives, stabilizing agents, emulsifiers, and/or buffers. An immune response may be an innate (e.g., a non-specific) immune response or a learned (e.g., acquired) immune response (e.g. that decreases the infectivity, morbidity, or onset of mortality in a subject (e.g., caused by exposure to a pathogenic microorganism) or that prevents infectivity, morbidity, or onset of mortality in a subject (e.g., caused by exposure to a pathogenic microorganism)). Thus, in some preferred embodiments, an immunogenic composition of the invention is administered to a subject as a vaccine (e.g., to prevent or attenuate a disease (e.g., allergic disease (e.g., by providing to the subject total or partial immunity against the disease or the total or partial attenuation (e.g., suppression) of a sign, symptom or condition of the disease (e.g., sign, symptom or condition of an allergic disease)))).

As used herein, the term "adjuvant" refers to any substance that can stimulate an immune response. Some adjuvants can cause activation of a cell of the immune system (e.g., an adjuvant can cause an immune cell to produce and secrete a cytokine). Examples of adjuvants that can cause activation of a cell of the immune system include, but are not limited to, nanoemulsion formulations described herein, saponins purified from the bark of the *Q. saponaria* tree, such as QS21 (a glycolipid that elutes in the 21st peak with HPLC fractionation; Aquila Biopharmaceuticals, Inc., Worcester, Mass.); poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and Leishmania elongation factor (a purified Leishmania protein; Corixa Corporation, Seattle, Wash.). Traditional adjuvants are well known in the art and include, for example, aluminum phosphate or hydroxide salts ("alum").

As used herein, the term "an amount effective to induce an immune response" (e.g., of a composition for inducing an immune response comprising a nanoemulsion formulated for injectable administration), refers to the dosage level required (e.g., when administered to a subject) to stimulate, generate and/or elicit an immune response in the subject. An effective amount can be administered in one or more administrations (e.g., via the same or different route), applications or dosages and is not intended to be limited to a particular formulation or administration route. Accordingly, a "therapeutically effective amount" (e.g., of a composition for inducing an immune response) refers to the dosage level or amount of a composition required (e.g., when administered to a subject (e.g., administered via injection)) to stimulate, generate and/or elicit a therapeutic benefit in a subject. A therapeutically effective amount can be administered in one or more administrations (e.g., via the same or different route), applications or dosages and is not intended to be limited to a particular formulation or administration route.

As used herein, the term "under conditions such that said subject generates an immune response" and grammatical equivalents refer to any qualitative or quantitative induction, generation, and/or stimulation of an immune response (e.g., innate or acquired).

A used herein, the term "immune response" and grammatical equivalents refer to a response by the immune system of a subject. For example, immune responses include, but are not limited to, a detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which the immunogenic polypeptide is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign). Thus, it is to be understood that, as used herein, "immune response" refers to any type of immune response, including, but not limited to, innate immune responses (e.g., activation of Toll receptor signaling cascade), cell-mediated immune responses (e.g., responses mediated by T cells (e.g., antigen-specific T cells) and non-specific cells of the immune system), and humoral immune responses (e.g., responses mediated by B cells (e.g., via generation and secretion of antibodies into the plasma, lymph, and/or tissue fluids). The term "immune response" is meant to encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

As used herein, the terms "toll receptors" and "TLRs" refer to a class of receptors (e.g., TLR1, TLR2, TLR3, TLR4, TLR5, TLR6, TLR7, TLR8, TLR9, TLRT0, TLR 11) that recognize special patterns of pathogens, termed pathogen-associated molecular patterns (See, e.g., Janeway and Medzhitov, (2002) Annu. Rev. Immunol. 20, 197-216). These receptors are expressed in innate immune cells (e.g., neutrophils, monocytes, macrophages, dendritic cells) and in other types of cells such as endothelial cells. Their ligands include bacterial products such as LPS, peptidoglycans, and lipopeptides. TLRs are receptors that bind to exogenous ligands and mediate innate immune responses leading to the elimination of invading microbes. The TLR-triggered signaling pathway leads to activation of transcription factors including NFkB, which is important for the induced expression of proinflammatory cytokines and chemokines. TLRs also interact with each other. For example, TLR2 can form functional heterodimers with TLR1 or TLR6. The TLR2/1 dimer has different ligand binding profile than the TLR2/6 dimer (Ozinsky et al., 2000). In some embodiments, a nanoemulsion adjuvant activates cell signaling through a TLR (e.g., TLR2 and/or TLR4). Thus, methods described herein include a nanoemulsion adjuvant composition (e.g., composition comprising NE adjuvant optionally combined with one or more immunogens (e.g., protein antigens or other antigen described herein)) that when administered to a subject, activates one or more TLRs and stimulates an immune response (e.g., innate and/or adaptive/acquired immune response) in a subject. Such an adjuvant can activate TLRs (e.g., TLR2 and/or TLR4) by, for example, interacting with TLRs (e.g., NE adjuvant binding to TLRs) or activating any downstream cellular pathway that occurs upon binding of a ligand to a TLR. NE adjuvants described herein that activate TLRs can also enhance the availability or accessibility of any endogenous or naturally occurring ligand of TLRs. A NE adjuvant that activates one or more TLRs can alter transcription of genes, increase translation of mRNA or increase the activity of proteins that are involved in mediating TLR cellular processes. For example, NE adjuvants described herein that activate one or more TLRs (e.g., TLR2 and/or TLR4) can induce expression of one or more cytokines (e.g., IL-8, IL-12p40, and/or IL-23).

As used herein, the term "immunity" refers to protection from disease (e.g., preventing or attenuating (e.g., suppression) of a sign, symptom or condition of the disease) upon exposure to a microorganism (e.g., pathogen) capable of causing the disease. Immunity can be innate (e.g., non-adaptive (e.g., non-acquired) immune responses that exist in the absence of a previous exposure to an antigen) and/or acquired/adaptive (e.g., immune responses that are mediated by B and T cells following a previous exposure to antigen (e.g., that exhibit increased specificity and reactivity to the antigen)).

As used herein, the terms "immunogen" and "antigen" are used interchangeably to refer to an agent (e.g., a microorganism (e.g., bacterium, virus or fungus) and/or portion or component thereof (e.g., protein, glycoprotein, lipoprotein, peptide, glycopeptide, lipopeptide, toxoid, carbohydrate, tumor-specific antigen, etc.)) that is capable of eliciting an immune response in a subject. In preferred embodiments, immunogens elicit immunity against the immunogen (e.g., microorganism (e.g., pathogen or a pathogen product), cancer and/or tumor, etc.) when administered in combination with a nanoemulsion adjuvant formulation of the invention comprising one or more antigens/immunogens together with an adjuvant formulation comprising an emulsion delivery system in combination with one or more immunostimulatory compounds (e.g., a compound that stimulates the innate immune system (e.g., a toll-like receptor antagonist (e.g., synthetic oligodeoxynucleotides (ODN) (e.g., ODN containing immunostimulatory CpG motifs (CpG))) or a saponin (e.g., a triterpene glycoside saponin (e.g., QS-21))) formulated for administration (e.g., via injectable route (e.g., intradermal, intramuscular, subcutaneously, etc.), mucosal route (e.g., nasally or vaginally), or other route) to a subject.

As used herein, "CpG oligonucleotide" "CpG ODN" and "CpG" refer to an immunostimulatory nucleic acid containing at least one cytosine-guanine dinucleotide sequence (e.g., a 5' cytidine followed by 3' guanosine and linked by a phosphate bond) and which activates the immune system. An "unmethylated CpG oligonucleotide" is a nucleic acid molecule which contains an unmethylated cytosine-guanine dinucleotide sequence (e.g., an unmethylated 5' cytidine followed by 3' guanosine and linked by a phosphate bond) and which activates the immune system. A "methylated CpG oligonucleotide" is a nucleic acid which contains a methylated cytosine-guanine dinucleotide sequence (e.g., a methylated 5' cytidine followed by a 3' guanosine and linked by a phosphate bond) and which activates the immune system. CpG oligonucleotides are well known in the art and are described in, e.g., U.S. Pat. Nos. 6,194,388; 6,207,646; 6,214,806; 6,218,371; 6,239,116; and 6,339,068; PCT Publication No. WO 01/22990; PCT Publication No. WO 03/015711; US Publication No. 20030139364, each of which are hereby incorporated by reference in its entirety.

As used herein, the term "pathogen product" refers to any component or product derived from a pathogen including, but not limited to, polypeptides, peptides, proteins, nucleic acids, membrane fractions, and polysaccharides.

As used herein, the term "enhanced immunity" refers to an increase in the level of adaptive and/or acquired immunity in a subject to a given immunogen (e.g., microorganism (e.g., pathogen)) following administration of a composition (e.g., composition for inducing an immune response of the present invention) relative to the level of adaptive and/or acquired immunity in a subject that has not been administered the composition (e.g., composition for inducing an immune response of the present invention).

As used herein, the terms "purified" or "to purify" refer to the removal of contaminants or undesired compounds from a sample or composition. As used herein, the term "substantially purified" refers to the removal of from about 70 to 90%, up to 100%, of the contaminants or undesired compounds from a sample or composition.

As used herein, the terms "administration" and "administering" refer to the act of giving a composition of the present invention (e.g., a composition for inducing an immune response) to a subject. Exemplary routes of administration to the human body include, but are not limited to, through the eyes (ophthalmic), mouth (oral), skin (transdermal), nose (nasal), lungs (inhalant), oral mucosa (buccal), ear, rectal, by injection (e.g., intravenously, subcutaneously, intraperitoneally, etc.), topically, and the like. A preferred route of administration, according to the invention, is via injection (e.g., intradermal, subcutaneous, intramuscular, intravenous, intraosseous, intraperitoneal, intrathecal, epidural, intracardiac, intraarticular, intracavernous, micropenetrators, microdialysis, and/or intravitreal).

As used herein, the terms "co-administration" and "co-administering" refer to the administration of at least two agent(s) (e.g., an immunogenic composition of the invention and one or more other agents or therapies to a subject). In some embodiments, the co-administration of two or more agents or therapies is concurrent. In other embodiments, a first agent/therapy is administered prior to a second agent/therapy. In some embodiments, co-administration can be via the same or different route of administration. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s) (e.g., lowers the level of toxic immunostimulatory agent (e.g., saponin) needed to be administered to generate a desired immune response), and/or when co-administration of two or more agents results in sensitization of a subject to beneficial effects of one of the agents via co-administration of the other agent. In other embodiments, co-administration is preferable to elicit an immune response in a subject to two or more different immunogens (e.g., antigens) at or near the same time (e.g., when a subject is unlikely to be available for subsequent administration of a second, third, or more composition for inducing an immune response).

As used herein, the term "topically" refers to application to the surface of the skin and/or mucosal cells and tissues (e.g., alveolar, buccal, lingual, masticatory, vaginal or nasal mucosa, and other tissues and cells which line hollow organs or body cavities). Topical administration may utilize a spray (e.g., a nasal spray), a cream, or other viscous solution.

The terms "pharmaceutically acceptable" or "pharmacologically acceptable," as used herein, refer to compositions that do not substantially produce adverse reactions (e.g., toxic, allergic or immunological reactions) when administered to a subject.

As used herein, the term "pharmaceutically acceptable carrier" refers to any of the standard pharmaceutical carriers including, but not limited to, phosphate buffered saline solution, water, and various types of wetting agents (e.g., sodium lauryl sulfate), any and all solvents, dispersion media, coatings, sodium lauryl sulfate, isotonic and absorption delaying agents, disintigrants (e.g., potato starch or sodium starch glycolate), polyethylethe glycol, and the like.. The compositions also can include stabilizers and preservatives. Examples of carriers, stabilizers and adjuvants have been described and are known in the art (See e.g., Martin, Remington's Pharmaceutical Sciences, 15th Ed., Mack Publ. Co., Easton, Pa. (1975), incorporated herein by reference).

As used herein, the term "pharmaceutically acceptable salt" refers to any salt (e.g., obtained by reaction with an acid or a base) of a composition of the present invention that is physiologically tolerated in the target subject. "Salts" of the compositions of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compositions of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$ and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compositions of the present invention are contemplated as being pharmaceutically acceptable. However, salts of acids and bases that are non-pharmaceutically acceptable may also find use, for example, in the preparation or purification of a pharmaceutically acceptable composition.

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., environmental conditions, exposures to detrimental compounds present in the environment, etc.). Thus, it is not intended that the present invention be limited to any particular risk (e.g., a subject may be "at risk for disease" simply by being exposed to and interacting with other people), nor is it intended that the present invention be limited to any particular disease.

"Nasal application", as used herein, means applied through the nose into the nasal or sinus passages or both. The application may, for example, be done by drops, sprays, mists, coatings or mixtures thereof applied to the nasal and sinus passages.

"Vaginal application", as used herein, means applied into or through the vagina so as to contact vaginal mucosa. The application may contact the urethra, cervix, fornix, uterus or other area surrounding the vagina. The application may, for example, be done by drops, sprays, mists, coatings, lubricants or mixtures thereof applied to the vagina or surrounding tissue.

As used herein, the term "kit" refers to any delivery system for delivering materials. In the context of immunogenic agents (e.g., a composition comprising one or more antigens/immunogens together with an adjuvant formulation comprising an emulsion delivery system in combination with one or more immunostimulatory compounds), such delivery systems include systems that allow for the storage, transport, or delivery of immunogenic agents and/or supporting materials (e.g., written instructions for using the materials, a syringe and/or needle, etc.). For example, kits include one or more enclosures (e.g., boxes) containing the relevant immunogenic agents (e.g., nanoemulsions) and/or supporting materials. As used herein, the term "fragmented kit" refers to delivery systems comprising two or more separate containers that each contain a subportion of the total kit components. The containers may be delivered to the intended recipient together or separately. For example, a first container may contain a composition comprising one or more antigens/immunogens together with an adjuvant formulation comprising an emulsion delivery system in combination with one or more immunostimulatory compounds for a particular use, while a second container contains a second agent (e.g., a syringe and/or needle). Indeed, any delivery system comprising two or more separate containers that each contains a subportion of the total kit components are included in the term "fragmented kit." In contrast, a "combined kit" refers to a delivery system containing all of the components of an immunogenic agent needed for a particular use in a single container (e.g., in a single box housing each of the desired components). The term "kit" includes both fragmented and combined kits.

DETAILED DESCRIPTION OF THE INVENTION

The present invention provides methods and compositions for the stimulation of immune responses. In particular, the invention provides methods and compositions for enhancing an immune response to one or more antigens.

Compositions and methods of the invention are useful for the treatment and/or prevention of microbial infections, such as infections caused by bacteria, viruses, fungi and parasites. Compositions and methods of the invention include one or more antigens/immunogens together with an adjuvant formulation comprising an emulsion in combination with one or more immunostimulatory compounds (e.g., a compound that stimulates the innate immune system (e.g., a toll-like receptor antagonist (e.g., synthetic oligodeoxynucleotides (ODN)))) that enhance immune responses to the one or more antigens/immunogens when administered to a subject. Compositions and methods of the invention find use in, among other things, clinical (e.g. therapeutic and preventative medicine (e.g., vaccination)) and research applications.

In general, an immune response is generated to an antigen through the interaction of the antigen with the cells of the immune system. Immune responses may be broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an immunogen). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs. Other responses, cells, and components of the immune system that can be assessed with respect to immune stimulation are known in the art.

An immune response refers to any qualitative or quantitative induction, generation, and/or stimulation of an immune response in a subject that is measurable. An immune response may be an innate immune response (e.g., non-adaptive (e.g., non-acquired) immune response that exists in the absence of a previous exposure to an antigen) or an acquired/adaptive immune response (e.g., immune response that is mediated by B and T cells following an exposure to antigen (e.g., that exhibit increased specificity and reactivity to the antigen)). In a preferred embodiment, an immune response generated by an immunogenic composition of the invention provides protection from disease (e.g., preventing or attenuating (e.g., suppression) of a sign, symptom or condition of the disease) upon exposure to a microorganism (e.g., pathogen) capable of causing the disease (e.g., from which an antigen/immunogen used in the immunogenic composition of the invention is derived). Such protection and/or prevention may be referred to as immunity.

The invention is not limited to any particular immune response. Immune responses include, but are not limited to, a detectable alteration (e.g., increase) in Toll-like receptor (TLR) activation, lymphokine (e.g., cytokine (e.g., Th1 or Th2 type cytokines) or chemokine) expression and/or secretion, macrophage activation, dendritic cell activation, T cell activation (e.g., CD4+ or CD8+ T cells), NK cell activation, and/or B cell activation (e.g., antibody generation and/or secretion). Additional examples of immune responses include binding of an immunogen (e.g., antigen (e.g., immunogenic polypeptide)) to an MHC molecule and inducing a cytotoxic T lymphocyte ("CTL") response, inducing a B cell response (e.g., antibody production), and/or T-helper lymphocyte response, and/or a delayed type hypersensitivity (DTH) response against the antigen from which an antigen/immunogen is derived, expansion (e.g., growth of a population of cells) of cells of the immune system (e.g., T cells, B cells (e.g., of any stage of development (e.g., plasma cells), and increased processing and presentation of antigen by antigen presenting cells. An immune response may be to immunogens that the subject's immune system recognizes as foreign (e.g., non-self antigens from microorganisms (e.g., pathogens), or self-antigens recognized as foreign. Immune responses include, but are not limited to, innate immune responses (e.g., activation of Toll receptor signaling cascade), cell-mediated immune responses (e.g., responses mediated by T cells (e.g., antigen-specific T cells) and non-specific cells of the immune system), and humoral immune responses (e.g., responses mediated by B cells (e.g., via generation and secretion of antibodies into the plasma, lymph, and/or tissue fluids) Immune responses encompass all aspects of the capability of a subject's immune system to respond to antigens and/or immunogens (e.g., both the initial response to an immunogen (e.g., a pathogen) as well as acquired (e.g., memory) responses that are a result of an adaptive immune response).

In a preferred embodiment, an immunogenic compositions of the invention comprising one or more antigens/immunogens together with an adjuvant formulation comprising an emulsion in combination with one or more immunostimulatory compounds induces an immune response to the one or more antigen/immunogens in a subject that is greater than the immune response induced in a subject to the one or more antigens/immunogens when the one or more antigens/immunogens are administered with only a single component of the immunogenic composition (e.g., when the one or more antigens/immunogens are administered with only the emulsion (e.g., a nanoemulsion described herein); or when the one or more antigens/immunogens are administered with only the immunostimulatory compound (e.g., a compound that stimulates the innate immune system (e.g., a toll-like receptor antagonist (e.g., synthetic oligodeoxynucleotides (ODN))))) (See, e.g., Example 1). In a further preferred embodiment, the immune response induced in a subject when an immunogenic compositions of the invention comprising one or more antigens/immunogens together with an adjuvant formulation comprising an emulsion in combination with one or more immunostimulatory compounds is administered to the subject is a synergistic immune response (e.g., synergistic compared to when the one or more antigens/immunogens are administered with only the emulsion (e.g., a nanoemulsion described herein); or when the one or more antigens/immunogens are administered with only the immunostimulatory compound (e.g., a compound that stimulates the innate immune system (e.g., a toll-like receptor antagonist (e.g., synthetic oligodeoxynucleotides (ODN))))) (See, e.g., Example 1).

As described herein, an immune response induced may be an innate immune response and/or an adaptive/acquired immune response.

Host innate immune responses enable a host to differentiate self from pathogen and provide a rapid inflammatory response, including production of cytokines and chemokines, elaboration of effector molecules, such as NO, and interactions with the adaptive immune response (See, e.g., Janeway and Medzhitov, (2002) Annu. Rev. Immunol. 20, 197-216). Molecular understanding of innate immunity in humans evolved the mid-1990s when the *Drosophila* protein Toll was shown to be critical for defending flies against fungal infections (See, e.g., Lemaitre et al., (1996). Cell 86, 973-983). The human Toll-like receptor (TLR) family includes at least ten receptors that play important roles in innate immunity (See, e.g., Akira et al., (2006) Cell 124, 783-801; Beutler et al., (2006) Annu. Rev. Immunol. 24, 353-380; and Takeda et al., (2003). Annu. Rev. Immunol. 21, 335-376).

In general, TLRs recognize and respond to diverse microbial molecules and enable the innate immune system to discriminate among groups of pathogens and to induce an appropriate cascade of effector responses. Individual TLRs recognize a distinct repertoire of conserved molecules (e.g., microbial products). For example, well-characterized receptor-ligand pairs include TLR4 and LPS (lipopolysaccharide), TLR5 and flagellin, TLR1/TLR2/TLR6 and lipoproteins, and TLR3/TLR7/TLR8/TLR9 and different nucleic acid motifs. Collectively, the family of TLRs allows a host's innate immune system to detect the presence of foreign molecules (e.g., microbial products of most microbial pathogens or other substances).

TLRs are classified as members of the IL-1R (IL-1 receptor) superfamily on the basis of a shared cytoplasmic region known as the TIR (Toll/IL-1R) domain. The extracellular portions of TLRs are rather diverse, comprising varying numbers of leucine-rich repeats. Following encounter with a microbe, TLRs trigger a complex cascade of events that lead to the induction of a range of proinflammatory genes (See, e.g., Yamamoto et al., (2002) Nature 420, 324-329 (See, e.g., Misch and Hawn, Clin Sci 2008, 114, 347-360)). Ligand binding results in the recruitment of several molecules to the receptor complex. These include TIR-domain-containing adaptor molecules such as MyD88 (myeloid differentiation primary response gene 88), TIRAP/Mal (TIR-domain-containing adapter/MyD88 adaptor-like), TICAM1/TRIF (TIR-domain-containing adaptor molecule 1/TIR-domain-containing adaptor-inducing interferon b) and TRAM (TRIF-related adaptor molecule). Further recruitment of molecules includes IRAKs (IL-1R-associated kinases (IRAK1, 2, 3 (M) and 4)) as well as TRAF6 (TNF receptor-associated factor 6). IRAK1 and TRAF6 then dissociate and bind another complex that comprises TAK1 (TGF (transforming growth factor)-b-activated kinase 1) and TAB1, 2 and 3 (TAK-1-binding proteins 1, 2 and 3). TAK1 then activates IKK (IkB (inhibitor of NF-kB (nuclear factor kB)) kinase). The activity of this complex is regulated by IKKg (also known as NEMO (NF-kB essential modulator)). IKK-mediated phosphorylation of IkB leads to its degradation, allowing NF-kB to translocate to the nucleus and promote the transcription of multiple proinflammatory genes, including TNF, IL-1b and IL-6.

TLR activation by pathogens, or by molecules derived therefrom, induces intracellular signaling that primarily results in activation of the transcription factor NF-kB (See, e.g., Beg, 2002, Trends Immunol. 2002 23 509-12.) and modulation of cytokine production. However, a series of other pathways can also be triggered, including p38 mitogen activated kinase, c-Jun-N-terminal kinase and extracellular signal related kinase pathways (See, e.g., Flohe, et al., 2003, J Immunol, 170 2340-2348; Triantafilou & Triantafilou, 2002, Trends Immunol, 23 301-304). The patterns of gene expression induced by ligation of the different TLRs are distinct but often overlap. For instance a large proportion of the genes upregulated by TLR3 agonists and double stranded RNA are also upregulated by TLR4 agonists and LPS (See, e.g., Doyle et al., 2002, Immunity, 17 251-263). TLR4 activation by LPS in macrophages results in TNF-α, IL-12 IL-1β, RANTES and MIP1β secretion (See, e.g., Flohe et al., supra; Jones et al., 2002, J Leukoc Biol, 69 1036-1044).

Adaptive/acquired immune responses are broadly categorized into two categories: humoral and cell mediated immune responses (e.g., traditionally characterized by antibody and cellular effector mechanisms of protection, respectively). These categories of response have been termed Th1-type responses (cell-mediated response), and Th2-type immune responses (humoral response).

Stimulation of an immune response can result from a direct or indirect response of a cell or component of the immune system to an intervention (e.g., exposure to an antigen/immunogen (e.g., an antigen combined with an adjuvant formulation of the invention comprising an emulsion in combination with one or more immunostimulatory compounds (e.g., a compound that stimulates an innate immune response (e.g., a toll-like receptor antagonist (e.g., synthetic oligodeoxynucleotides (ODN)))). Immune responses can be measured in many ways including activation, proliferation or differentiation of cells of the immune system (e.g., B cells, T cells, dendritic cells, APCs, macrophages, NK cells, NKT cells etc.); up-regulated or down-regulated expression of markers and cytokines; stimulation of IgA, IgM, or IgG titer; splenomegaly (including increased spleen cellularity); hyperplasia and mixed cellular infiltrates in various organs.

Although an understanding of the mechanism is not necessary to practice the present invention and the present invention is not limited to any particular mechanism of action, in some embodiments, immunogenic compositions and methods of the present invention (e.g., comprising one or more antigens and an adjuvant formulation comprising an emulsion in combination with one or more immunostimulatory compounds) induce an additive or a more than additive expression and/or secretion of cytokines (e.g., by macrophages, dendritic cells and/or CD4+ T cells) when administered to a subject when compared to when the one or more antigens/immunogens are administered with only the emulsion (e.g., a nanoemulsion described herein); or when the one or more antigens/immunogens are administered with only the immunostimulatory compound (e.g., a compound that stimulates the innate immune system (e.g., a toll-like receptor antagonist (e.g., synthetic oligodeoxynucleotides (ODN)))). Modulation of expression of a particular cytokine can occur locally or systemically. It is known that cytokine profiles can determine T cell regulatory and effector functions in immune responses. In some embodiments, Th1-type cytokines are induced, and thus, the immunostimulatory compositions of the present invention promote (and can be used to promote) a Th1 type antigen-specific immune response including cytotoxic T-cells.

Cytokines play a role in directing the T cell response. Helper (CD4+) T cells orchestrate the immune response of mammals through production of soluble factors that act on other immune system cells, including B and other T cells. Most mature CD4+T helper cells express one of two cytokine profiles: Th1 or Th2. Th1-type CD4+ T cells secrete IL-2, IL-3, IFN-γ, GM-CSF and high levels of TNF-α. Th2 cells express IL-3, IL-4, IL-5, IL-6, IL-9, IL-10, IL-13, GM-CSF and low levels of TNF-α. Th1 type cytokines promote both cell-mediated immunity, and humoral immunity that is characterized by immunoglobulin class switching to IgG2a in mice and IgG1 in humans. Th1 responses may also be associated with delayed-type hypersensitivity and autoimmune disease. Th2 type cytokines induce primarily humoral immunity and induce class switching to IgG1 and IgE. The antibody isotypes associated with Th1 responses generally have neutralizing and opsonizing capabilities whereas those associated with Th2 responses are associated more with allergic responses.

Several factors have been shown to influence skewing of an immune response towards either a Th1 or Th2 type response. The best characterized regulators are cytokines. IL-12 and IFN-γ are positive Th1 and negative Th2 regulators. IL-12 promotes IFN-γ production, and IFN-γ provides positive feedback for IL-12. IL-4 and IL-10 appear important for the establishment of the Th2 cytokine profile and to down-regulate Th1 cytokine production.

In some embodiments, immunogenic compositions and methods of the invention stimulate a Th-17 immune response (e.g., comprising expression and/or secretion of IL-17).

In some preferred embodiments, the present invention provides immunogenic compositions and methods of using the same to stimulate a Th1-type immune response in a subject comprising administering to a subject an immunogenic composition described herein.

The invention is not limited by the type of immunostimulatory molecule/compound used in an immunogenic composition of the invention (e.g., in an adjuvant formulation comprising an emulsion in combination with one or more immunostimulatory agents/compounds). Indeed, a variety of a immunostimulatory molecules/compounds may be used including, but not limited to, the following. In some embodiments, monophosphoryl lipid A (e.g., in particular 3-de-O-acylated monophosphoryl lipid A (3D-MPL)), is used. 3D-MPL is a well-known adjuvant manufactured by Ribi Immunochem, Montana. Chemically it is often supplied as a mixture of 3-de-O-acylated monophosphoryl lipid A with either 4, 5, or 6 acylated chains. In some embodiments, diphosphoryl lipid A, and 3-O-deacylated variants thereof are used. Each of these immunogens can be purified and prepared by methods described in GB 2122204B, hereby incorporated by reference in its entirety. Other purified and synthetic lipopolysaccharides have been described (See, e.g., U.S. Pat. No. 6,005,099 and EP 0 729 473; Hilgers et al., 1986, Int. Arch. Allergy. Immunol., 79(4):392-6; Hilgers et al., 1987, Immunology, 60(1):141-6; and EP 0 549 074, each of which is hereby incorporated by reference in its entirety). In some embodiments, 3D-MPL is used in the form of a particulate formulation (e.g., having a small particle size less than 0.2 μm in diameter, described in EP 0 689 454, hereby incorporated by reference in its entirety). In some embodiments, saponins are used in an adjuvant formulation of an immunogenic composition of the present invention. Saponins are well known adjuvants (See, e.g., Lacaille-Dubois and Wagner (1996) Phytomedicine vol 2 pp 363-386). Examples of saponins include Quil A (derived from the bark of the South American tree *Quillaja saponaria* Molina), and fractions thereof (See, e.g., U.S. Pat. No. 5,057,540; Kensil, Crit Rev Ther Drug Carrier Syst, 1996, 12 (1-2):1-55; and EP 0 362 279, each of which is hereby incorporated by reference in its entirety). Also useful in the present invention are the haemolytic saponins QS7, QS17, and QS21 (e.g., HPLC purified fractions of Quil A; See, e.g., Kensil et al. (1991). J. Immunology 146, 431-437, U.S. Pat. No. 5,057,540; WO 96/33739; WO 96/11711 and EP 0 362 279, each of which is hereby incorporated by reference in its entirety). Also useful are combinations of QS21 and polysorbate or cyclodextrin (See, e.g., WO 99/10008, hereby incorporated by reference in its entirety). In some embodiments, an immunogenic oligonucleotide containing unmethylated CpG dinucleotides ("CpG") is used as an adjuvant in the present invention. CpG is an abbreviation for cytosine-guanosine dinucleotide motifs present in DNA. CpG is known in the art as being an adjuvant when administered by both systemic and mucosal routes (See, e.g., WO 96/02555, EP 468520, Davis et al., J. Immunol, 1998, 160(2):870-876; McCluskie and Davis, J. Immunol., 1998, 161(9):4463-6; and U.S. Pat. App. No. 20050238660, each of which is hereby incorporated by reference in its entirety). For example, in some embodiments, the immunostimulatory sequence is Purine-Purine-C-G-pyrimidine-pyrimidine; wherein the CG motif is not methylated.

Although an understanding of the mechanism is not necessary to practice the present invention and the present invention is not limited to any particular mechanism of action, in some embodiments, the presence of one or more CpG oligonucleotides activate various immune subsets including natural killer cells (which produce IFN-γ) and macrophages. In some embodiments, CpG oligonucleotides are formulated into an immunogenic composition of the present invention for inducing an immune response. In some embodiments, a free solution of CpG is co-administered together with an antigen (e.g., present within a NE solution). In some embodiments, a NE plus CpG is co-administered together with an antigen. In some embodiments, a CpG oligonucleotide is covalently conjugated to an antigen (See, e.g., WO 98/16247, hereby incorporated by reference), or formulated with a carrier such as aluminium hydroxide (See, e.g., Brazolot-Millan et al., Proc. Natl. Acad Sci., USA, 1998, 95(26), 15553-8).

In some embodiments, adjuvants such as Complete Freunds Adjuvant and Incomplete Freunds Adjuvant, cytokines (e.g., interleukins (e.g., IL-2, IFN-γ, IL-4, etc.), macrophage colony stimulating factor, tumor necrosis factor, etc.), detoxified mutants of a bacterial ADP-ribosylating toxin such as a cholera toxin (CT), a pertussis toxin (PT), or an *E. Coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (See, e.g., WO93/13202 and WO92/19265, each of which is hereby incorporated by reference), and/or other immunogenic compounds/substances (e.g., that stimulate an immune response) are used in or in combination with an immunogenic composition comprising an adjuvant formulation comprising an emulsion in combination with one or more immunostimulatory compounds of the present invention.

Additional examples of adjuvants that may be used in or in combination with an immunogenic composition of the invention (e.g., an immunogenic composition comprising an adjuvant formulation comprising an emulsion in combination with one or more immunostimulatory compounds) include poly(di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and Leishmania elongation factor (a purified Leishmania protein; Corixa Corporation, Seattle, Wash.).

Adjuvants may be added to a composition comprising a nanoemulsion adjuvant and an immunogen, or, the adjuvant may be formulated with carriers, for example liposomes, or metallic salts (e.g., aluminium salts (e.g., aluminium hydroxide)) prior to combining with or co-administration with a composition comprising a nanoemulsion adjuvant and an immunogen.

In some embodiments, an immunogenic composition comprising a nanoemulsion adjuvant and an immunogen comprises a single additional immunostimulatory compound/molecule and/or adjuvant. In other embodiments, an immunogenic composition comprising a nanoemulsion adjuvant and an immunogen comprises two or more additional immunostimulatory compounds/molecules and/or adjuvants (See, e.g., WO 94/00153; WO 95/17210; WO 96/33739; WO 98/56414; WO 99/12565; WO 99/11241; and WO 94/00153, each of which is hereby incorporated by reference in its entirety).

In some embodiments, an immunogenic composition described herein (e.g., comprising one or more antigens/immunogens together with an adjuvant formulation comprising an emulsion in combination with one or more immunostimulatory compounds) of the present invention comprises one or more mucoadhesives (See, e.g., U.S. Pat. App. No. 20050281843, hereby incorporated by reference in its entirety). The present invention is not limited by the type of mucoadhesive utilized. Indeed, a variety of mucoadhesives are contemplated to be useful in the present invention including, but not limited to, cross-linked derivatives of poly(acrylic acid) (e.g., carbopol and polycarbophil), polyvinyl alcohol, polyvinyl pyrollidone, polysaccharides (e.g., alginate and chitosan), hydroxypropyl methylcellulose, lectins, fimbrial proteins, and carboxymethylcellulose. In some embodiments, one or more components of a NE adjuvant of the immunogenic composition function as a mucoadhesive (e.g., individually, or in combination with other components of the NE adjuvant). Although an understanding of the mechanism is not necessary to practice the present invention and the present invention is not limited to any particular mechanism of action, in some embodiments, use of a mucoadhesive (e.g., in an immunogenic composition of the invention) enhances induction of an immune response (e.g., an innate and/or adaptive immune response) in a subject (e.g., a subject administered an immunogenic composition of the present invention) due to an increase in duration and/or amount of exposure to the immunogenic composition that a subject experiences when a mucoadhesive is used compared to the duration and/or amount of exposure to the immunogenic composition in the absence of using the mucoadhesive.

In some embodiments, one or more components of the immunogenic composition function to delay the release of the antigen/immunogen component of the composition. Although an understanding of the mechanism is not necessary to practice the present invention and the present invention is not limited to any particular mechanism of action, in some embodiments, delayed or time release (e.g., using particle technology and encapsulation technology known in the art enhances induction of an immune response (e.g., an innate and/or adaptive immune response) in a subject (e.g., a subject administered an immunogenic composition of the present invention) due to an increase in duration and/or amount of exposure to the immunogenic composition that a subject experiences compared to the duration and/or amount of exposure to the immunogenic composition in the absence of the delayed and/or timed release component.

In some embodiments, a composition of the present invention may comprise sterile aqueous preparations. Acceptable vehicles and solvents include, but are not limited to, water, Ringer's solution, phosphate buffered saline and isotonic sodium chloride solution. In addition, sterile, fixed oils are conventionally employed as a solvent or suspending medium. For this purpose any bland fixed mineral or non-mineral oil may be employed including synthetic mono-ordi-glycerides. In addition, fatty acids such as oleic acid find use in the preparation of injectables. Carrier formulations suitable for mucosal, subcutaneous, intramuscular, intraperitoneal, intravenous, or administration via other routes may be found in Remington's Pharmaceutical Sciences, Mack Publishing Company, Easton, Pa.

An immunogenic composition of the present invention can be used therapeutically (e.g., to enhance an immune response) or as a prophylactic (e.g., for immunization (e.g., to prevent signs or symptoms of disease)). An immunogenic composition of the present invention can be administered to a subject via a number of different delivery routes and methods.

For example, an immunogenic composition of the present invention can be administered to a subject (e.g., mucosally (e.g., nasal mucosa, vaginal mucosa, etc.)) by multiple methods, including, but not limited to: being suspended in a solution and applied to a surface; being suspended in a solution and sprayed onto a surface using a spray applicator; being mixed with a mucoadhesive and applied (e.g., sprayed or wiped) onto a surface (e.g., mucosal surface); being placed on or impregnated onto a nasal and/or vaginal applicator and applied; being applied by a controlled-release mechanism; being applied as a liposome; or being applied on a polymer.

In some embodiments, compositions of the present invention are administered mucosally (e.g., using standard techniques; See, e.g., Remington: The Science and Practice of Pharmacy, Mack Publishing Company, Easton, Pa., 19th edition, 1995 (e.g., for mucosal delivery techniques, including intranasal, pulmonary, vaginal and rectal techniques), as well as European Publication No. 517,565 and Ilium et al., J. Controlled Rel., 1994, 29:133-141 (e.g., for techniques of intranasal administration), each of which is hereby incorporated by reference in its entirety). Alternatively, the compositions of the present invention may be administered dermally or transdermally, using standard techniques (See, e.g., Remington: The Science arid Practice of Pharmacy, Mack Publishing Company, Easton, Pa., 19th edition, 1995). The present invention is not limited by the route of administration.

In some embodiments, an immunogenic composition of the present invention is used to protect and/or treat a subject susceptible to, or suffering from, a disease by means of administering the composition via injection (e.g., via intradermal, subcutaneous, intramuscular, intravenous, intraosseous, intraperitoneal, intrathecal, epidural, intracardiac, intraarticular, intracavernous, and/or intravitreal route). Methods of systemic administration include conventional syringes and needles, or devices designed for ballistic delivery (See, e.g., WO 99/27961, hereby incorporated by reference), or needleless pressure liquid jet device (See, e.g., U.S. Pat. Nos. 4,596,556; 5,993,412, each of which are hereby incorporated by reference), or transdermal patches (See, e.g., WO 97/48440; WO 98/28037, each of which are hereby incorporated by reference). In some embodiments, the present invention provides a delivery device for systemic administration, pre-filled with an immunogenic composition of the present invention.

In some embodiments, an immunogenic composition of the present invention is used to protect or treat a subject susceptible to, or suffering from, disease by means of administering a composition of the present invention via a mucosal route (e.g., an oral/alimentary or nasal route). Alternative mucosal routes include intravaginal and intrarectal routes. In preferred embodiments of the present invention, a nasal route of administration is used, termed "intranasal administration" or "intranasal vaccination" herein. Methods of intranasal vaccination are well known in the art, including the administration of a droplet or spray form of the vaccine into the nasopharynx of a subject to be immunized. In some embodiments, a nebulized or aerosolized immunogenic composition is provided. Enteric formulations such as gastro resistant capsules for oral administration, suppositories for rectal or vaginal administration also form part of this invention. Compositions of the present invention may also be administered via the oral route. Under these circumstances, an immunogenic composition may comprise a pharmaceutically acceptable excipient and/or include alkaline buffers, or enteric capsules. Formulations for nasal delivery may include those with dextran or cyclodextran and saponin as an adjuvant.

An immunogenic composition may also be administered via a vaginal route. In such cases, an immunogenic composition may comprise pharmaceutically acceptable excipients and/or emulsifiers, polymers (e.g., CARBOPOL), and other known stabilizers of vaginal creams and suppositories. In some embodiments, compositions of the invention are administered via a rectal route. In such cases, an immunogenic composition may comprise excipients and/or waxes and polymers known in the art for forming rectal suppositories.

In some embodiments, the same route of administration (e.g., mucosal administration) is chosen for both a priming and boosting vaccination. In some embodiments, multiple routes of administration are utilized (e.g., at the same time, or, alternatively, sequentially) in order to stimulate an immune response (e.g., using one or more immunogenic compositions of the present invention).

For example, in some embodiments, an immunogenic composition is administered to a mucosal surface of a subject in either a priming or boosting vaccination regime. Alternatively, in some embodiments, an immunogenic composition is administered systemically in either a priming or boosting vaccination regime. In some embodiments, an immunogenic composition is administered to a subject in a priming vaccination regimen via mucosal administration and a boosting regimen via systemic administration. In some embodiments, an immunogenic composition is administered to a subject in a priming vaccination regimen via systemic administration and a boosting regimen via mucosal administration. Examples of systemic routes of administration include, but are not limited to, a parenteral, intramuscular, intradermal, transdermal, subcutaneous, intraperitoneal or intravenous administration. An immunogenic composition may be used for both prophylactic and therapeutic purposes.

NEs have not been shown to be inflammatory when placed on the skin or mucous membranes in studies on animals and in humans. Thus, although an understanding of the mechanism is not necessary to practice the present invention and the present invention is not limited to any particular mechanism of action, in some embodiments, a composition comprising an immunogenic composition of the present invention (e.g., comprising an adjuvant formulation comprising an emulsion in combination with one or more immunostimulatory compounds) acts to transport and/or present antigen/immunogen to the immune system (e.g., to antigen presenting cells of the immune system). In a preferred embodiment, a composition comprising an immunogenic composition of the present invention (e.g., comprising one or more antigens and an adjuvant formulation comprising an emulsion in combination with one or more immunostimulatory compounds) acts to transport and/or present antigen to the immune system (e.g., to antigen presenting cells of the immune system) in a greater way or in a synergistic way compared to when the one or more antigens are administered with only the emulsion (e.g., a nanoemulsion described herein); or when the one or more antigens are administered with only the immunostimulatory compound (e.g., a compound that stimulates the innate immune system (e.g., a toll-like receptor antagonist (e.g., synthetic oligodeoxynucleotides (ODN)))) (See, e.g., Example 1). In some embodiments, mucosal administration of an immunogenic composition of the present invention generates mucosal (e.g., signs of mucosal immunity (e.g., generation of IgA antibody titers)) as well as systemic immunity. In some embodiments, mucosal administration of immunogenic composition of the invention generates an innate immune response (e.g., activates Toll-like receptor signaling and/or activation of NF-kB) in a subject. Both cellular and Immoral immunity play a role in protection against multiple pathogens and both can be induced with immunogenic composition of the present invention.

Accordingly, in a preferred embodiment, administration of an immunogenic composition of the present invention primes, enables and/or enhances induction of both humoral (e.g., development of specific antibodies) and cellular (e.g., cytotoxic T lymphocyte) immune responses (e.g., against a pathogen). In some embodiments, an immunogenic composition of the present invention is used in a vaccine (e.g., as an immunostimulatory adjuvant (e.g., that elicits and/or enhances immune responses (e.g., innate and or adaptive immune responses) in a host administered the immunogenic composition).

In some embodiments, the present invention provides immunogenic compositions comprising an adjuvant formulation comprising an emulsion in combination with one or more immunostimulatory compounds (e.g., a compound that stimulates the innate immune system (e.g., a toll-like receptor antagonist (e.g., synthetic oligodeoxynucleotides (ODN)))) that possesses greater efficacy at eliciting immune responses (e.g., innate immune responses and/or adaptive/acquired immune responses) than either emulsion or the one or more immunostimulatory compounds can individually. Although an understanding of a mechanism is not necessary to practice the present invention, and the present invention is not limited to any particular mechanism of action, in some embodiments, one or more antigens of an immunogenic composition of the invention are more readily internalized by phagocytic cells (e.g., macrophages, dendritic cells, B cells, etc.) or other cells compared to when the one or more antigens/immunogens are administered with only the emulsion (e.g., a nanoemulsion described herein); or when the one or more antigens/immunogens are administered with only the immunostimulatory compound (e.g., leading to greater internalization of the one or more antigens (e.g., by antigen presenting cells), processing of antigen, and/or presentation of antigen to B and/or T cells). Thus, in some embodiments, greater internalization and/or processing of antigen and/or presentation of antigen to B and/or T cells leads to stronger, more robust immune responses (e.g., to an antigen administered in an immunogenic composition of the invention.

In some embodiments, the present invention provides an immunogenic composition that generates a desired immune response in a subject administered the same (e.g., an adaptive immune response). For example, in some embodiments, the present invention provides an immunogenic composition that skew a host's immune response away from Th2 type immune response and toward a Th1 type immune response (e.g., based upon selection of the constituents of an the immunogenic composition). In particular, conventional alum based vaccines for a variety of diseases such as respiratory syncitial virus (RSV), anthrax, and hepatitis B virus each lead to a predominant Th2 type immune response in a subject administered the vaccine (e.g., characterized by enhanced expression of Th2 type cytokines and the production of IgG1 antibodies). However, an immunogenic composition of the invention is able to, in one embodiment, redirect the conventionally observed Th2 type immune response in host subjects administered conventional vaccines. Thus, in some embodiments, the present invention provides immunogenic compositions and methods for skewing and/or redirecting a host's immune response (e.g., away from Th2 type immune responses and toward Th1 type immune responses) to one or a plurality of immunogens/antigens. In some embodiments, skewing and/or redirecting a host's immune response (e.g., away from Th2 type immune responses and toward Th1 type immune responses) to one or a plurality of immunogens/antigens comprises providing one or more antigens (e.g., recombinant antigens, isolated and/or purified antigens, and/or killed whole pathogens) that are historically associated with generation of a Th2 type immune response when administered to a subject (e.g., RSV antigen, hepatitis B virus antigen, etc.), combining the one or more antigens with an immunogenic composition of the invention, and administering the immunogenic composition to a subject under conditions sufficient to induce the desired immune response.

In some embodiments, the present invention provides an immunogenic composition that reduces the number of booster injections (e.g., of an antigen containing composition) required to achieve a desired immune response (e.g., a protective immune response (e.g., a memory immune response)). In some embodiments, the present invention provides an immunogenic composition that results in a higher proportion of recipients achieving seroconversion and/or more consistent immune responses within a population of subjects administered the immunogenic composition. In some embodiments, the present invention provides immunogenic compositions that are useful for selectively skewing adaptive immunity toward Th1, Th2, or cytotoxic T cell responses (e.g., allowing effective immunization by distinct routes (e.g., such as via mucosa or via injection)). In some embodiments, the present invention provides immunogenic compositions that elicit optimal responses in subjects in which most contemporary vaccination strategies are not optimally effective (e.g., in very young and/or very old populations). In some embodiments, the present invention provides immunogenic compositions that provide efficacy and safety needed for vaccination regimens that involve different delivery routes and elicitation of distinct types of immunity. In some embodiments, the present invention provides immunogenic compositions that stimulate antibody responses and have little toxicity and that can be utilized with a range of antigens for which they provide adjuvanticity and the types of immune responses they elicit. In some embodiments, the present invention provides immunogenic compositions that meet global supply requirements (e.g., in response to a pathogenic (e.g., influenza) pandemic).

Generation of Antibodies

An immunogenic composition of the invention can be used to immunize a mammal, such as a mouse, rat, rabbit, guinea pig, monkey, or human, to produce polyclonal antibodies. If desired, an antigen can be conjugated to a carrier protein, such as bovine serum albumin, thyroglobulin, keyhole limpet hemocyanin or other carrier described herein. Depending on the host species, various additional adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, nanoemulsions described herein, keyhole limpet hemocyanin, and dinitrophenol). Among adjuvants used in humans, BCG (bacilli Calmette-Guerin) and *Corynebacterium parvum* are especially useful.

Monoclonal antibodies can be prepared using any technique which provides for the production of antibody molecules by continuous cell lines in culture. These techniques include, but are not limited to, the hybridoma technique, the human B cell hybridoma technique, and the EBV hybridoma technique (See, e.g., Kohler et al., Nature 256, 495 497, 1985; Kozbor et al., J. Immunol. Methods 81, 3142, 1985; Cote et al., Proc. Natl. Acad. Sci. 80, 2026 2030, 1983; Cole et al., Mol. Cell. Biol. 62, 109 120, 1984).

In addition, techniques developed for the production of "chimeric antibodies," the splicing of mouse antibody genes to human antibody genes to obtain a molecule with appropriate antigen specificity and biological activity, can be used (See, e.g., Morrison et al., Proc. Natl. Acad. Sci. 81, 68516855, 1984; Neuberger et al., Nature 312, 604 608, 1984; Takeda et al., Nature 314, 452 454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions.

Alternatively, humanized antibodies can be produced using recombinant methods, as described below. Antibodies which specifically bind to a particular antigen can contain antigen binding sites which are either partially or fully humanized, as disclosed in U.S. Pat. No. 5,565,332.

Alternatively, techniques described for the production of single chain antibodies can be adapted using methods known in the art to produce single chain antibodies which specifically bind to a particular antigen. Antibodies with related specificity, but of distinct idiotypic composition, can be generated by chain shuffling from random combinatorial immunoglobin libraries (See, e.g., Burton, Proc. Natl. Acad. Sci. 88, 11120 23, 1991).

Single-chain antibodies also can be constructed using a DNA amplification method, such as PCR, using hybridoma cDNA as a template (See, e.g., Thirion et al., 1996, Eur. J. Cancer Prev. 5, 507-11). Single-chain antibodies can be mono- or bispecific, and can be bivalent or tetravalent. Construction of tetravalent, bispecific single-chain antibodies is taught, for example, in Coloma & Morrison, 1997, Nat. Biotechnol. 15, 159-63. Construction of bivalent, bispecific single-chain antibodies is taught, for example, in Mallender & Voss, 1994, J. Biol. Chem. 269, 199-206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (See, e.g., Verhaar et al., 1995, Int. J. Cancer 61, 497-501; Nicholls et al., 1993, J. Immunol. Meth. 165, 81-91).

Antibodies can be produced by inducing in vivo production in the lymphocyte population or by screening immunoglobulin libraries or panels of highly specific binding reagents as disclosed in the literature (See, e.g., Orlandi et al., Proc. Natl. Acad. Sci. 86, 3833 3837, 1989; Winter et al., Nature 349, 293 299, 1991).

Chimeric antibodies can be constructed as disclosed in WO 93/03151. Binding proteins which are derived from immunoglobulins and which are multivalent and multispecific, such as the "diabodies" described in WO 94/13804, also can be prepared. Antibodies can be purified by methods well known in the art. For example, antibodies can be affinity purified by passage over a column to which the relevant antigen is bound. The bound antibodies can then be eluted from the column using a buffer with a high salt concentration.

Immunogenic compositions of the invention are not limited by the type of nanoemulsion utilized. Any number of suitable nanoemulsion compositions may be utilized in the immunogenic compositions (e.g., vaccines) compositions of the present invention, including, but not limited to, those disclosed in Hamouda et al., J. Infect Dis., 180:1939 (1999); Hamouda and Baker, J. Appl. Microbiol., 89:397 (2000); and Donovan et al., Antivir. Chem. Chemother., 11:41 (2000). Preferred nanoemulsions of the present invention are those that are non-toxic to animals. In preferred embodiments, nanoemulsions utilized in the compositions and methods of the present invention are stable, and do not decompose even after long storage periods (e.g., one or more years). Additionally, preferred emulsions maintain stability even after exposure to high temperature and freezing. This is especially useful if they are to be applied in extreme conditions (e.g., extreme heat or cold).

Some embodiments of the present invention employ an oil phase containing ethanol. For example, in some embodiments, the emulsions of the present invention contain (i) an aqueous phase and (ii) an oil phase containing ethanol as the organic solvent and optionally a germination enhancer, and (iii) TYLOXAPOL as the surfactant (preferably 2-5%, more preferably 3%). This formulation is highly efficacious for inactivation of pathogens and is also non-irritating and non-toxic to mammalian subjects (e.g., and thus can be used for administration to a mucosal surface).

In some other embodiments, the emulsions of the present invention comprise a first emulsion emulsified within a second emulsion, wherein (a) the first emulsion comprises (i) an aqueous phase; and (ii) an oil phase comprising an oil and an organic solvent; and (iii) a surfactant; and (b) the second emulsion comprises (i) an aqueous phase; and (ii) an oil phase comprising an oil and a cationic containing compound; and (iii) a surfactant.

Nanoemulsions.

As described herein, experiments conducted during development of embodiments of the invention identified certain, specific nanoemulsion formulations that, when combined with other immunostimulatory compounds/molecules, displayed synergistic immunostimulatory properties (e.g., when administered to a subject (See, e.g., Example 1)).

Emulsion formulations described herein are simply examples to illustrate the variety of nanoemulsion adjuvants that find use in the present invention. The present invention contemplates that many variations of these formulations, as well as additional nanoemulsions, find use in the methods of the present invention. Candidate emulsions can be easily tested to determine if they are suitable for use in the immunogenic compositions of the invention.

In preferred embodiments of the present invention, emulsion formulations are non-toxic (e.g., to humans, plants, or animals), non-irritant (e.g., to humans, plants, or animals), and non-corrosive (e.g., to humans, plants, or animals or the environment), while retaining stability when mixed with other agents (e.g., a composition comprising an immunogen (e.g., bacteria, fungi, viruses, and spores).

The nanoemulsion can comprise an aqueous phase, at least one oil, at least one surfactant, and at least one solvent. Nanoemulsions of the present disclosure may comprise the following properties and components.

The nanoemulsion vaccine of the present disclosure comprises droplets having an average diameter size of less than about 1000 nm, less than about 950 nm, less than about 900 nm, less than about 850 nm, less than about 800 nm, less than about 750 nm, less than about 700 nm, less than about 650 nm, less than about 600 nm, less than about 550 nm, less than about 500 nm, less than about 450 nm, less than about 400 nm, less than about 350 nm, less than about 300 nm, less than about 250 nm, less than about 200 nm, less than about 150 nm, or any combination thereof. In one embodiment, the droplets have an average diameter size greater than about 125 nm and less than or equal to about 600 nm. In a different embodiment, the droplets have an average diameter size greater than about 50 nm or greater than about 70 nm, and less than or equal to about 125 nm.

Aqueous Phase. The aqueous phase can comprise any type of aqueous phase including, but not limited to, water (e.g., $H_2O$, distilled water, purified water, water for injection, de-ionized water, tap water) and solutions (e.g., phosphate buffered saline (PBS) solution). In certain embodiments, the aqueous phase comprises water at a pH of about 4 to 10, preferably about 6 to 8. The water can be deionized (hereinafter "$DiH_2O$"). In some embodiments the aqueous phase comprises phosphate buffered saline (PBS). The aqueous phase may further be sterile and pyrogen free.

Organic Solvents. Organic solvents in the nanoemulsion include, but are not limited to, $C_1$-$C_{12}$ alcohol, diol, triol, dialkyl phosphate, tri-alkyl phosphate, such as tri-n-butyl phosphate, semi-synthetic derivatives thereof, and combinations thereof. In one aspect of the disclosed, the organic solvent is an alcohol chosen from a nonpolar solvent, a polar solvent, a protic solvent, or an aprotic solvent.

Suitable organic solvents include, but are not limited to, ethanol, methanol, isopropyl alcohol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, glycerol, sorbitol, industrial methylated spirit, triacetin, hexane, benzene, toluene, diethyl ether, chloroform, 1,4-dixoane, tetrahydrofuran, dichloromethane, acetone, acetonitrile, dimethylformamide, dimethyl sulfoxide, formic acid, semi-synthetic derivatives thereof, and any combination thereof.

Oil Phase. The oil in the nanoemulsion can be any cosmetically or pharmaceutically acceptable oil. The oil can be volatile or non-volatile, and may be chosen from animal oil, vegetable oil, natural oil, synthetic oil, hydrocarbon oils, silicone oils, semi-synthetic derivatives thereof, and combinations thereof.

Suitable oils include, but are not limited to, mineral oil, squalene oil, flavor oils, silicon oil, essential oils, water insoluble vitamins, Isopropyl stearate, Butyl stearate, Octyl palmitate, Cetyl palmitate, Tridecyl behenate, Diisopropyl adipate, Dioctyl sebacate, Menthyl anthranhilate, Cetyl octanoate, Octyl salicylate, Isopropyl myristate, neopentyl glycol dicarpate cetols, Ceraphyls®, Decyl oleate, diisopropyl adipate, $C_{12-15}$ alkyl lactates, Cetyl lactate, Lauryl lactate, Isostearyl neopentanoate, Myristyl lactate, Isocetyl stearoyl stearate, Octyldodecyl stearoyl stearate, Hydrocarbon oils, Isoparaffin, Fluid paraffins, Isododecane, Petrolatum, Argan oil, Canola oil, Chile oil, Coconut oil, corn oil, Cottonseed oil, Flaxseed oil, Grape seed oil, Mustard oil, Olive oil, Palm oil, Palm kernel oil, Peanut oil, Pine seed oil, Poppy seed oil, Pumpkin seed oil, Rice bran oil, Safflower oil, Tea oil, Truffle oil, Vegetable oil, Apricot (kernel) oil, Jojoba oil (*Simmondsia chinensis* seed oil), Grapeseed oil, Macadamia oil, Wheat germ oil, Almond oil, Rapeseed oil, Gourd oil, Soybean oil, Sesame oil, Hazelnut oil, Maize oil, Sunflower oil, Hemp oil, Bois oil, Kuki nut oil, Avocado oil, Walnut oil, Fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, Marhoram flower oil, orange flower oil, rose flower oil, ylang-ylang flower oil, Bark oil, cassia Bark oil, cinnamon bark oil, sassafras Bark oil, Wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, Oleic acid, Linoleic acid, Oleyl alcohol, Isostearyl alcohol, semi-synthetic derivatives thereof, and any combinations thereof.

The oil may further comprise a silicone component, such as a volatile silicone component, which can be the sole oil in the silicone component or can be combined with other silicone and non-silicone, volatile and non-volatile oils. Suitable silicone components include, but are not limited to, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

The volatile oil can be the organic solvent, or the volatile oil can be present in addition to an organic solvent. Suitable volatile oils include, but are not limited to, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, chenopodium oil, citronellal, citral, citronellol, chamazulene, yarrow, guaiazulene, chamomile, semi-synthetic derivatives, or combinations thereof. In one aspect of the disclosed, the volatile oil in the silicone component is different than the oil in the oil phase.

Surfactants. The surfactant in the nanoemulsion can be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

Exemplary useful surfactants are described in *Applied Surfactants: Principles and Applications* (Tharwat F. Tadros, Copyright August 2005 WILEY-VCH Verlag GmbH & Co. KGaA, Weinheim ISBN: 3-527-30629-3), which is specifically incorporated by reference. Further, the surfactant can be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Examples of polymeric surfactants include, but are not limited to, a graft copolymer of a poly (methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Surface active agents or surfactants, are amphipathic molecules that consist of a non-polar hydrophobic portion, usually a straight or branched hydrocarbon or fluorocarbon chain containing 8-18 carbon atoms, attached to a polar or ionic hydrophilic portion. The hydrophilic portion can be nonionic, ionic or zwitterionic. The hydrocarbon chain interacts weakly with the water molecules in an aqueous environment, whereas the polar or ionic head group interacts strongly with water molecules via dipole or ion-dipole interactions. Based on the nature of the hydrophilic group, surfactants are classified into anionic, cationic, zwitterionic, nonionic and polymeric surfactants.

Suitable surfactants include, but are not limited to, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate, sorbitan monolaurate, sorbitan monopalmitate, sorbitan monostearate, sorbitan monooleate, ethoxylated hydrogenated ricin oils, sodium laurylsulfate, a diblock copolymer of ethyleneoxyde and propyleneoxyde, Ethylene Oxide-Propylene Oxide Block Copolymers, and tetra-functional block copolymers based on ethylene oxide and propylene oxide, Glyceryl monoesters, Glyceryl caprate, Glyceryl caprylate, Glyceryl cocate, Glyceryl erucate, Glyceryl hydroxysterate, Glyceryl isostearate, Glyceryl lanolate, Glyceryl laurate, Glyceryl linolate, Glyceryl myristate, Glyceryl oleate, Glyceryl PABA, Glyceryl palmitate, Glyceryl ricinoleate, Glyceryl stearate, Glyceryl thiglycolate, Glyceryl dilaurate, Glyceryl dioleate, Glyceryl dimyristate, Glyceryl disterate, Glyceryl sesuioleate, Glyceryl stearate lactate, Polyoxyethylene cetyl/stearyl ether, Polyoxyethylene cholesterol ether, Polyoxyethylene laurate or dilaurate, Polyoxyethylene stearate or distearate, polyoxyethylene fatty ethers, Polyoxyethylene lauryl ether, Polyoxyethylene stearyl ether, polyoxyethylene myristyl ether, a steroid, Cholesterol, Betasitosterol, Bisabolol, fatty acid esters of alcohols, isopropyl myristate, Aliphati-isopropyl n-butyrate, Isopropyl n-hexanoate, Isopropyl n-decanoate, Isproppyl palmitate, Octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG40 lanolin, PEG- 40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional suitable surfactants include, but are not limited to, non-ionic lipids, such as glyceryl laurate, glyceryl myristate, glyceryl dilaurate, glyceryl dimyristate, semi-synthetic derivatives thereof, and mixtures thereof.

In additional embodiments, the surfactant is a polyoxyethylene fatty ether having a polyoxyethylene head group ranging from about 2 to about 100 groups, or an alkoxylated alcohol having the structure $R_5$—$(OCH_2\ CH_2)_y$—OH, wherein $R_5$ is a branched or unbranched alkyl group having from about 6 to about 22 carbon atoms and y is between about 4 and about 100, and preferably, between about 10 and about 100. Preferably, the alkoxylated alcohol is the species wherein $R_5$ is a lauryl group and y has an average value of 23. In a different embodiment, the surfactant is an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, but are not limited to, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, Bis(polyethylene glycol bis[imidazoyl carbonyl]), nonoxynol-9, Bis(polyethylene glycol bis[imidazoyl carbonyl]), Brij® 35, Brij® 56, Brij® 72, Brij® 76, Brij® 92V, Brij® 97, Brij® 58P, Cremophor® EL, Decaethylene glycol monododecyl ether, N-Decanoyl-N-methylglucamine, n-Decyl alpha-D-glucopyranoside, Decyl beta-D-maltopyranoside, n-Dodecanoyl-N-methylglucamide, n-Dodecyl alpha-D-maltoside, n-Dodecyl beta-D-maltoside, n-Dodecyl beta-D-maltoside, Heptaethylene glycol monodecyl ether, Heptaethylene glycol monododecyl ether, Heptaethylene glycol monotetradecyl ether, n-Hexadecyl beta-D-maltoside, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-alpha-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-beta-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from *Quillaja* bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tergitol, Tergitol, Type TMN-10, Tergitol, Type TMN-6, Tetradecyl-beta-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165, Triton® X-305, Triton® X-405, Triton® X-45, Triton® X-705-70, TWEEN® 20, TWEEN® 21, TWEEN® 40, TWEEN® 60, TWEEN® 61, TWEEN® 65, TWEEN® 80, TWEEN® 81, TWEEN® 85, Tyloxapol, n-Undecyl beta-D-glucopyranoside, semi-synthetic derivatives thereof, or combinations thereof.

In addition, the nonionic surfactant can be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, Poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, Poloxamers are used in the formulation of skin cleansers, bath products, shampoos, hair conditioners, mouthwashes, eye makeup remover and other skin and hair products. Examples of Poloxamers include, but are not limited to, Poloxamer 101, Poloxamer 105, Poloxamer 108, Poloxamer 122, Poloxamer 123, Poloxamer 124, Poloxamer 181, Poloxamer 182, Poloxamer 183, Poloxamer 184, Poloxamer 185, Poloxamer 188, Poloxamer 212, Poloxamer 215, Poloxamer 217, Poloxamer 231, Poloxamer 234, Poloxamer 235, Poloxamer 237, Poloxamer 238, Poloxamer 282, Poloxamer 284, Poloxamer 288, Poloxamer 331, Poloxamer 333, Poloxamer 334, Poloxamer 335, Poloxamer 338, Poloxamer 401, Poloxamer 402, Poloxamer 403, Poloxamer 407, Poloxamer 105 Benzoate, and Poloxamer 182 Dibenzoate.

Suitable cationic surfactants include, but are not limited to, a quaternary ammonium compound, an alkyl trimethyl ammonium chloride compound, a dialkyl dimethyl ammonium chloride compound, a cationic halogen-containing compound, such as cetylpyridinium chloride, Benzalkonium chloride, Benzalkonium chloride, Benzyldimethylhexadecylammonium chloride, Benzyldimethyltetradecylammonium chloride, Benzyldodecyldimethylammonium bromide, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Girard's reagent T, Hexadecyltrimethylammonium bromide, Hexadecyltrimethylammonium bromide, N,N',N'-Polyoxyethylene(10)-N-tallow-1,3-diaminopropane, Thonzonium bromide, Trimethyl (tetradecyl)ammonium bromide, 1,3,5-Triazine-1,3,5(2H, 4H,6H)-triethanol, 1-Decanaminium, N-decyl-N, N-dimethyl-, chloride, Didecyl dimethyl ammonium chloride, 2-(2-(p-(Diisobutyl)cresosxy)ethoxy)ethyl dimethyl benzyl ammonium chloride, 2-(2-(p-(Diisobutyl)phenoxy) ethoxy)ethyl dimethyl benzyl ammonium chloride, Alkyl 1 or 3 benzyl-1-(2-hydroxethyl)-2-imidazolinium chloride, Alkyl bis(2-hydroxyethyl) benzyl ammonium chloride, Alkyl demethyl benzyl ammonium chloride, Alkyl dimethyl 3,4-dichlorobenzyl ammonium chloride (100% $C_{12}$), Alkyl dimethyl 3,4-dichlorobenzyl ammonium chloride (50% $C_{14}$, 40% Cu, 10% $C_{16}$), Alkyl dimethyl 3,4-dichlorobenzyl ammonium chloride (55% $C_{14}$, 23% Cu, 20% $C_{16}$), Alkyl dimethyl benzyl ammonium chloride, Alkyl dimethyl benzyl ammonium chloride (100% $C_{14}$), Alkyl dimethyl benzyl ammonium chloride (100% $C_{16}$), Alkyl dimethyl benzyl ammonium chloride (41% $C_{14}$, 28% Cu), Alkyl dimethyl benzyl ammonium chloride (47% Cu, 18% $C_{14}$), Alkyl dimethyl benzyl ammonium chloride (55% C16, 20% $C_{14}$), Alkyl dimethyl benzyl ammonium chloride (58% $C_{14}$, 28% $C_{16}$), Alkyl dimethyl benzyl ammonium chloride (60% $C_{14}$, 25% $C_{12}$), Alkyl dimethyl benzyl ammonium chloride (61% Cu, 23% $C_{14}$), Alkyl dimethyl benzyl ammonium chloride (61% Cu, 23% $C_{14}$), Alkyl dimethyl benzyl ammonium chloride (65% Cu, 25% $C_{14}$), Alkyl dimethyl benzyl ammonium chloride (67% Cu, 24% $C_{14}$), Alkyl dimethyl benzyl ammonium chloride (67% $C_{12}$, 25% $C_{14}$), Alkyl dimethyl benzyl ammonium chloride (90% $C_{14}$, 5% $C_{12}$), Alkyl dimethyl benzyl ammonium chloride (93% $C_{14}$, 4% Cu), Alkyl dimethyl benzyl ammonium chloride (95% $C_{16}$, 5% $C_{18}$), Alkyl dimethyl benzyl ammonium chloride, Alkyl didecyl dimethyl ammonium chloride, Alkyl dimethyl benzyl ammonium chloride, Alkyl dimethyl benzyl ammonium chloride ($C_{12-16}$), Alkyl dimethyl benzyl ammonium chloride ($C_{12-18}$), Alkyl dimethyl benzyl ammonium chloride, dialkyl dimethyl benzyl ammonium chloride, Alkyl dimethyl dimethybenzyl ammonium chloride, Alkyl dimethyl ethyl ammonium bromide (90% $C_{14}$, 5% $C_{16}$, 5% $C_{12}$), Alkyl dimethyl ethyl ammonium bromide (mixed alkyl and alkenyl groups as in the fatty acids of soybean oil), Alkyl dimethyl ethylbenzyl ammonium chloride, Alkyl dimethyl ethylbenzyl ammonium chloride (60% $C_{14}$), Alkyl dimethyl isopropylbenzyl ammonium chloride (50% Cu, 30% $C_{14}$, 17% $C_{16}$, 3% $C_{18}$), Alkyl trimethyl ammonium chloride (58% $C_{18}$, 40% $C_{16}$, 1% $C_{14}$, 1% $C_{12}$), Alkyl trimethyl ammonium chloride (90% $C_{18}$, 10% $C_{16}$), Alkyldimethyl (ethylbenzyl) ammonium chloride ($C_{12-18}$), Di-($C_{8-10}$)-alkyl dimethyl ammonium chlorides, Dialkyl dimethyl ammonium chloride, Dialkyl methyl benzyl ammonium chloride, Didecyl dimethyl ammonium chloride, Diisodecyl dimethyl ammonium chloride, Dioctyl dimethyl ammonium chloride, Dodecyl bis (2-hydroxyethyl) octyl hydrogen ammonium chloride, Dodecyl dimethyl benzyl ammonium chloride, Dodecylcarbamoyl methyl dinethyl benzyl ammonium chloride, Heptadecyl hydroxyethylimidazolinium chloride, Hexahydro-1,3,5-tris(2-hydroxyethyl)-s-triazine, Hexahydro-1,3,5-tris(2-hydroxyethyl)-s-triazine, Myristalkonium chloride (and) Quat RNIUM 14, N,N-Dimethyl-2-hydroxypropylammonium chloride polymer, n-Tetradecyl dimethyl benzyl ammonium chloride monohydrate, Octyl decyl dimethyl ammonium chloride, Octyl dodecyl dimethyl ammonium chloride, Octyphenoxyethoxyethyl dimethyl benzyl ammonium chloride, Oxydiethylenebis(alkyl dimethyl ammonium chloride), Quaternary ammonium compounds, dicoco alkyldimethyl, chloride, Trimethoxysily propyl dimethyl octadecyl ammonium chloride, Trimethoxysilyl quats, Trimethyl dodecylbenzyl ammonium chloride, semi-synthetic derivatives thereof, and combinations thereof.

Exemplary cationic halogen-containing compounds include, but are not limited to, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. In some particular embodiments, suitable cationic halogen containing compounds comprise, but are not limited to, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In particularly preferred embodiments, the cationic halogen containing compound is CPC, although the compositions of the present disclosed are not limited to formulation with an particular cationic containing compound.

Suitable anionic surfactants include, but are not limited to, a carboxylate, a sulphate, a sulphonate, a phosphate, chenodeoxycholic acid, chenodeoxycholic acid sodium salt, cholic acid, ox or sheep bile, Dehydrocholic acid, Deoxycholic acid, Deoxycholic acid, Deoxycholic acid methyl ester, Digitonin, Digitoxigenin, N,N-Dimethyldodecylamine N-oxide, Docusate sodium salt, Glycochenodeoxycholic acid sodium salt, Glycocholic acid hydrate, synthetic, Glycocholic acid sodium salt hydrate, synthetic, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine solution, N-Lauroylsarcosine solution, Lithium dodecyl sulfate, Lithium dodecyl sulfate, Lithium dodecyl sulfate, Lugol solution, Niaproof 4, Type 4, 1-Octanesulfonic acid sodium salt, Sodium 1-butanesulfonate, Sodium 1-decanesulfonate, Sodium 1-decanesulfonate, Sodium 1-dodecanesulfonate, Sodium 1-heptanesulfonate anhydrous, Sodium 1-heptanesulfonate anhydrous, Sodium 1-nonanesulfonate, Sodium 1-propanesulfonate monohydrate, Sodium 2-bromoethanesulfonate, Sodium cholate hydrate, Sodium choleate, Sodium deoxycholate, Sodium deoxycholate monohydrate, Sodium dodecyl sulfate, Sodium hexanesulfonate anhydrous, Sodium octyl sulfate, Sodium pentanesulfonate anhydrous, Sodium taurocholate, Taurochenodeoxycholic acid sodium salt, Taurodeoxycholic acid sodium salt monohydrate, Taurohyodeoxycholic acid sodium salt hydrate, Taurolithocholic acid 3-sulfate disodium salt, Tauroursodeoxycholic acid sodium salt, Trizma® dodecyl sulfate, TWEEN® 80, Ursodeoxycholic acid, semi-synthetic derivatives thereof, and combinations thereof.

Suitable zwitterionic surfactants include, but are not limited to, an N-alkyl betaine, lauryl amindo propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(Decyldimethylammonio)propanesulfonate inner salt, 3-Dodecyldimethylammonio)propanesulfonate inner salt, SigmaUltra, 3-(Dodecyldimethylammonio)propanesulfonate inner salt, 3-(N,N-Dimethylmyristylammonio) propanesulfonate, 3-(N,N-Dimethyloctadecylammonio)propanesulfonate, 3-(N,N-Dimethyloctylammonio) propanesulfonate inner salt, 3-(N,N-Dimethylpalmitylammonio)propanesulfonate, semi-synthetic derivatives thereof, and combinations thereof.

In some embodiments, the nanoemulsion comprises a cationic surfactant, which can be cetylpyridinium chloride. In other embodiments of the disclosed, the nanoemulsion comprises a cationic surfactant, and the concentration of the cationic surfactant is less than about 5.0% and greater than about 0.001%. In yet another embodiment of the disclosed, the nanoemulsion comprises a cationic surfactant, and the concentration of the cationic surfactant is selected from the group consisting of less than about 5%, less than about 4.5%, less than about 4.0%, less than about 3.5%, less than about 3.0%, less than about 2.5%, less than about 2.0%, less than about 1.5%, less than about 1.0%, less than about 0.90%, less than about 0.80%, less than about 0.70%, less than about 0.60%, less than about 0.50%, less than about 0.40%, less than about 0.30%, less than about 0.20%, or less than about 0.10%. Further, the concentration of the cationic agent in the nanoemulsion is greater than about 0.002%, greater than about 0.003%, greater than about 0.004%, greater than about 0.005%, greater than about 0.006%, greater than about 0.007%, greater than about 0.008%, greater than about 0.009%, greater than about 0.010%, or greater than about 0.001%. In one embodiment, the concentration of the cationic agent in the nanoemulsion is less than about 5.0% and greater than about 0.001%.

In another embodiment, the nanoemulsion comprises at least one cationic surfactant and at least one non-cationic surfactant. The non-cationic surfactant is a nonionic surfactant, such as a polysorbate (Tween), such as polysorbate 80 or polysorbate 20. In one embodiment, the non-ionic surfactant is present in a concentration of about 0.01% to about 5.0%, or the non-ionic surfactant is present in a concentration of about 0.1% to about 3%. In yet another embodiment, the nanoemulsion comprises a cationic surfactant present in a concentration of about 0.01% to about 2%, in combination with a nonionic surfactant.

Additional Ingredients. Additional compounds suitable for use in the nanoemulsion include but are not limited to one or more solvents, such as an organic phosphate-based solvent, bulking agents, coloring agents, pharmaceutically acceptable excipients, a preservative, pH adjuster, buffer, chelating agent, etc. The additional compounds can be admixed into a previously emulsified nanoemulsion vaccine, or the additional compounds can be added to the original mixture to be emulsified. In certain of these embodiments, one or more additional compounds are admixed into an existing nanoemulsion composition immediately prior to its use.

Suitable preservatives in the nanoemulsion include, but are not limited to, cetylpyridinium chloride, benzalkonium chloride, benzyl alcohol, chlorhexidine, imidazolidinyl urea, phenol, potassium sorbate, benzoic acid, bronopol, chlorocresol, paraben esters, phenoxyethanol, sorbic acid, alpha-tocophernol, ascorbic acid, ascorbyl palmitate, butylated hydroxyanisole, butylated hydroxytoluene, sodium ascorbate, sodium metabisulphite, citric acid, edetic acid, semi-synthetic derivatives thereof, and combinations thereof. Other suitable preservatives include, but are not limited to, benzyl alcohol, chlorhexidine (bis (p-chlorophenyldiguanido) hexane), chlorphenesin (3-(-4-chloropheoxy)-propane-1,2-diol), Kathon CG (methyl and methylchloroisothiazolinone), parabens (methyl, ethyl, propyl, butyl hydrobenzoates), phenoxyethanol (2-phenoxyethanol), sorbic acid (potassium sorbate, sorbic acid), Phenonip (phenoxyethanol, methyl, ethyl, butyl, propyl parabens), Phenoroc (phenoxyethanol 0.73%, methyl paraben 0.2%, propyl paraben 0.07%), Liquipar Oil (isopropyl, isobutyl, butylparabens), Liquipar PE (70% phenoxyethanol, 30% liquipar oil), Nipaguard MPA (benzyl alcohol (70%), methyl & propyl parabens), Nipaguard MPS (propylene glycol, methyl & propyl parabens), Nipasept (methyl, ethyl and propyl parabens), Nipastat (methyl, butyl, ethyl and propyel parabens), Elestab 388 (phenoxyethanol in propylene glycol plus chlorphenesin and methylparaben), and Killitol (7.5% chlorphenesin and 7.5% methyl parabens).

The nanoemulsion vaccine may further comprise at least one pH adjuster. Suitable pH adjusters in the nanoemulsion vaccine of the disclosed include, but are not limited to, diethyanolamine, lactic acid, monoethanolamine, triethylanolamine, sodium hydroxide, sodium phosphate, semi-synthetic derivatives thereof, and combinations thereof.

In addition, the nanoemulsion can comprise a chelating agent. In one embodiment, the chelating agent is present in an amount of about 0.0005% to about 1%. Examples of chelating agents include, but are not limited to, ethylenediamine, ethylenediaminetetraacetic acid (EDTA), phytic acid, polyphosphoric acid, citric acid, gluconic acid, acetic acid, lactic acid, and dimercaprol, and a preferred chelating agent is ethylenediaminetetraacetic acid. The nanoemulsion can comprise a buffering agent, such as a pharmaceutically acceptable buffering agent. Examples of buffering agents include, but are not limited to, 2-Amino-2 methyl-1,3-propanediol, ≥99.5% (NT), 2-Amino-2-methyl-1-propanol, ≥99.0% (GC), L-(+) Tartaric acid, ≥99.5% (T), ACES, ≥99.5% (T), ADA, ≥99.0% (T), Acetic acid, ≥99.5% (GC/T), Acetic acid, for luminescence, ≥99.5% (GC/T), Ammonium acetate solution, for molecular biology, ~5 M in $H_2O$, Ammonium acetate, for luminescence, ≥99.0% (calc. on dry substance, T), Ammonium bicarbonate, ≥99.5% (T), Ammonium citrate dibasic, ≥99.0% (T), Ammonium formate solution, 10 M in $H_2O$, Ammonium formate, ≥99.0% (calc. based on dry substance, NT), Ammonium oxalate monohydrate, ≥99.5% (RT), Ammonium phosphate dibasic solution, 2.5 M in $H_2O$, Ammonium phosphate dibasic, ≥99.0% (T), Ammonium phosphate monobasic solution, 2.5 M in $H_2O$, Ammonium phosphate monobasic, ≥99.5% (T), Ammonium sodium phosphate dibasic tetrahydrate, ≥99.5% (NT), Ammonium sulfate solution, for molecular biology, 3.2 M in $H_2O$, Ammonium tartrate dibasic solution, 2 M in 1120 (colorless solution at 20° C.), Ammonium tartrate dibasic, ≥99.5% (T), BES buffered saline, for molecular biology, 2× concentrate, BES, ≥99.5% (T), BES, for molecular biology, ≥99.5% (T), BICINE buffer Solution, for molecular biology, 1 M in $H_2O$, BICINE, ≥99.5% (T), BIS-TRIS, ≥99.0% (NT), Bicarbonate buffer solution, ≥0.1 M $Na_2CO_3$, ≥0.2 M $NaHCO_3$, Boric acid, ≥99.5% (T), Boric acid, for molecular biology, ≥99.5% (T), CAPS, ≥99.0% (TLC), CHES, ≥99.5% (T), Calcium acetate hydrate, ≥99.0% (calc. on dried material, KT), Calcium carbonate, precipitated, ≥99.0% (KT), Calcium citrate tribasic tetrahydrate, ≥98.0% (calc. on dry substance, KT), Citrate Concentrated Solution, for molecular biology, 1 M in $H_2O$, Citric acid, anhydrous, ≥99.5% (T), Citric acid, for luminescence, anhydrous, ≥99.5% (T), Diethanolamine, ≥99.5% (GC), EPPS, ≥99.0% (T), Ethylenediaminetetraacetic acid disodium salt dihydrate, for molecular biology, ≥99.0% (T), Formic acid solution, 1.0 M in $H_2O$, Gly-Gly-Gly, ≥99.0% (NT), Gly-Gly, ≥99.5% (NT), Glycine, ≥99.0% (NT), Glycine, for luminescence, ≥99.0% (NT), Glycine, for molecular biology, ≥99.0% (NT), HEPES buffered saline, for molecular biology, 2× concentrate, HEPES, ≥99.5% (T), HEPES, for molecular biology, ≥99.5% (T), Imidazole buffer Solution, 1 M in $H_2O$, Imidazole, ≥99.5% (GC), Imidazole, for luminescence, ≥99.5% (GC), Imidazole, for molecular biology, ≥99.5% (GC), Lipoprotein Refolding Buffer, Lithium acetate dihydrate, ≥99.0% (NT), Lithium citrate tribasic tetrahydrate, ≥99.5% (NT), MES hydrate, ≥99.5% (T), MES monohydrate, for luminescence, ≥99.5% (T), MES solution, for molecular biology, 0.5 M in $H_2O$, MOPS, ≥99.5% (T), MOPS, for luminescence, ≥99.5% (T), MOPS, for molecular biology, ≥99.5% (T), Magnesium acetate solution, for molecular biology, ~1 M in $H_2O$, Magnesium acetate tetrahydrate, ≥99.0% (KT), Magnesium citrate tribasic nonahydrate, ≥98.0% (calc. based on dry substance, KT), Magnesium formate solution, 0.5 M in H₂O, Magnesium phosphate dibasic trihydrate, ≥98.0% (KT), Neutralization solution for the in-situ hybridization for in-situ hybridization, for molecular biology, Oxalic acid dihydrate, ≥99.5% (RT), PIPES, ≥99.5% (T), PIPES, for molecular biology, ≥99.5% (T), Phosphate buffered saline, solution (autoclaved), Phosphate buffered saline, washing buffer for peroxidase conjugates in Western Blotting, 10× concentrate, Piperazine, anhydrous, ≥99.0% (T), Potassium D-tartrate monobasic, ≥99.0% (T), Potassium acetate solution, for molecular biology, Potassium acetate solution, for molecular biology, 5 M in H₂O, Potassium acetate solution, for molecular biology, ~1 M in H₂O, Potassium acetate, ≥99.0% (NT), Potassium acetate, for luminescence, ≥99.0% (NT), Potassium acetate, for molecular biology, ≥99.0% (NT), Potassium bicarbonate, ≥99.5% (T), Potassium carbonate, anhydrous, ≥99.0% (T), Potassium chloride, ≥99.5% (AT), Potassium citrate monobasic, ≥99.0% (dried material, NT), Potassium citrate tribasic solution, 1 M in H₂O, Potassium formate solution, 14 M in H₂O, Potassium formate, ≥99.5% (NT), Potassium oxalate monohydrate, ≥99.0% (RT), Potassium phosphate dibasic, anhydrous, ≥99.0% (T), Potassium phosphate dibasic, for luminescence, anhydrous, ≥99.0% (T), Potassium phosphate dibasic, for molecular biology, anhydrous, ≥99.0% (T), Potassium phosphate monobasic, anhydrous, ≥99.5% (T), Potassium phosphate monobasic, for molecular biology, anhydrous, ≥99.5% (T), Potassium phosphate tribasic monohydrate, ≥95% (T), Potassium phthalate monobasic, ≥99.5% (T), Potassium sodium tartrate solution, 1.5 M in H₂O, Potassium sodium tartrate tetrahydrate, ≥99.5% (NT), Potassium tetraborate tetrahydrate, ≥99.0% (T), Potassium tetraoxalate dihydrate, ≥99.5% (RT), Propionic acid solution, 1.0 M in H₂O, STE buffer solution, for molecular biology, pH 7.8, STET buffer solution, for molecular biology, pH 8.0, Sodium 5,5-diethylbarbiturate, ≥99.5% (NT), Sodium acetate solution, for molecular biology, ~3 M in H₂O, Sodium acetate trihydrate, ≥99.5% (NT), Sodium acetate, anhydrous, ≥99.0% (NT), Sodium acetate, for luminescence, anhydrous, ≥99.0% (NT), Sodium acetate, for molecular biology, anhydrous, ≥99.0% (NT), Sodium bicarbonate, ≥99.5% (T), Sodium bitartrate monohydrate, ≥99.0% (T), Sodium carbonate decahydrate, ≥99.5% (T), Sodium carbonate, anhydrous, ≥99.5% (calc. on dry substance, T), Sodium citrate monobasic, anhydrous, ≥99.5% (T), Sodium citrate tribasic dihydrate, ≥99.0% (NT), Sodium citrate tribasic dihydrate, for luminescence, ≥99.0% (NT), Sodium citrate tribasic dihydrate, for molecular biology, ≥99.5% (NT), Sodium formate solution, 8 M in H₂O, Sodium oxalate, 299.5% (RT), Sodium phosphate dibasic dihydrate, 299.0% (T), Sodium phosphate dibasic dihydrate, for luminescence, ≥99.0% (T), Sodium phosphate dibasic dihydrate, for molecular biology, 299.0% (T), Sodium phosphate dibasic dodecahydrate, ≥99.0% (T), Sodium phosphate dibasic solution, 0.5 M in H₂O, Sodium phosphate dibasic, anhydrous, ≥99.5% (T), Sodium phosphate dibasic, for molecular biology, ≥99.5% (T), Sodium phosphate monobasic dihydrate, ≥99.0% (T), Sodium phosphate monobasic dihydrate, for molecular biology, ≥99.0% (T), Sodium phosphate monobasic monohydrate, for molecular biology, ≥99.5% (T), Sodium phosphate monobasic solution, 5 M in H₂O, Sodium pyrophosphate dibasic, ≥99.0% (T), Sodium pyrophosphate tetrabasic decahydrate, ≥99.5% (T), Sodium tartrate dibasic dihydrate, ≥99.0% (NT), Sodium tartrate dibasic solution, 1.5 M in H₂O (colorless solution at 20° C.), Sodium tetraborate decahydrate, ≥99.5% (T), TAPS, ≥99.5% (T), TES, ≥99.5% (calc. based on dry substance, T), TM buffer solution, for molecular biology, pH 7.4, TNT buffer solution, for molecular biology, pH 8.0, TRIS Glycine buffer solution, 10× concentrate, TRIS acetate-EDTA buffer solution, for molecular biology, TRIS buffered saline, 10× concentrate, TRIS glycine SDS buffer solution, for electrophoresis, 10× concentrate, TRIS phosphate-EDTA buffer solution, for molecular biology, concentrate, 10× concentrate, Tricine, ≥99.5% (NT), Triethanolamine, ≥99.5% (GC), Triethylamine, ≥99.5% (GC), Triethylammonium acetate buffer, volatile buffer, ~1.0 M in H₂O, Triethylammonium phosphate solution, volatile buffer, ~1.0 M in H₂O, Trimethylammonium acetate solution, volatile buffer, ~1.0 M in H₂O, Trimethylammonium phosphate solution, volatile buffer, ~1 M in H₂O, Tris-EDTA buffer solution, for molecular biology, concentrate, 100× concentrate, Tris-EDTA buffer solution, for molecular biology, pH 7.4, Tris-EDTA buffer solution, for molecular biology, pH 8.0, Trizma® acetate, ≥99.0% (NT), Trizma® base, ≥99.8% (T), Trizma® base, ≥99.8% (T), Trizma® base, for luminescence, ≥99.8% (T), Trizma® base, for molecular biology, ≥99.8% (T), Trizma® carbonate, ≥98.5% (T), Trizma® hydrochloride buffer solution, for molecular biology, pH 7.2, Trizma® hydrochloride buffer solution, for molecular biology, pH 7.4, Trizma® hydrochloride buffer solution, for molecular biology, pH 7.6, Trizma® hydrochloride buffer solution, for molecular biology, pH 8.0, Trizma® hydrochloride, ≥99.0% (AT), Trizma® hydrochloride, for luminescence, ≥99.0% (AT), Trizma® hydrochloride, for molecular biology, ≥99.0% (AT), and Trizma® maleate, ≥99.5% (NT).

The nanoemulsion can comprise one or more emulsifying agents to aid in the formation of emulsions. Emulsifying agents include compounds that aggregate at the oil/water interface to form a kind of continuous membrane that prevents direct contact between two adjacent droplets. Certain embodiments feature nanoemulsion that may readily be diluted with water or another aqueous phase to a desired concentration without impairing their desired properties.

As described herein, an immunogenic composition of the invention may comprise one or more immunostimulatory compounds. Examples of immunostimulatory compounds include, but are not limited to, chitosan, glucan, enterotoxin, nucleic acid (e.g., CpG motifs), MF59, alum, ASO system, etc. Indeed, a variety of immunostimulatory compounds known in the art may be used in an adjuvant formulation (e.g., for use in an immunogenic composition) of the invention. Immunostimulatory compounds include, but are not limited to, a TLR antagonist (e.g., a polyinosinic-polycytidylic acid (poly (IC)) (e.g., that activates TLR3); Pam3CSK4 (e.g., that activates TLR1/2); FSL-1 and/or MALP2 (e.g., that activate TLR2/6); monophosphoryl lipid A, (MPL) (e.g., that activate TLR4); flagellin (e.g., that activate TLR5); imiquimod (e.g., that activate TLR7); a Class B CpG phosphorothioate oligodeoxynucleotide, (CpG ODN) (e.g., that activate TLR9); a multi-pattern recognition receptors (multi-PRR ligand) (e.g., that act as agonists for dual or multiple TLR receptors and other PRRs)); a RIG-I-like receptor agonist (e.g., 5′ppp dsRNA and/or Poly(I:C)/ LyoVec complexes); NOD and NOD-like receptor ligand agonists; inflammasome inducers (e.g., alum, alum salts, and/or alum crystals, chitosan, etc.); cytosolic DNA Sensors (CDS) and STING Ligands; immune cell receptors (e.g., CD40L, FMS-like tyrosine kinase ligand (e.g., Flt3 ligand), and multimeric immune cell receptors); Cytokines and chemokines (e.g., IL-1, IL-6, TGF-β, IL-12, IL-15, interferons (α, β, γ, δ), GM-CSF and others); synthetic glycolipids (e.g., alpha-galactosylceramide); and/or vitamins (e.g., retinoic acid). It is within the purview of one of ordinary skill in the art to employ suitable immunostimulatory compounds/immune modulators in the context of the present disclosure An immunostimulatory compound can be present in an immunogenic composition at any pharmaceutically acceptable amount including, but not limited to, from about 0.001% up to about 10%, and any amount in between, such as about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10%.

Exemplary Nanoemulsions. An exemplary nanoemulsion adjuvant composition according to the invention is designated "W805EC" or "DODAC NE" adjuvant. The composition of W805EC or DODAC NE adjuvant is shown in Table 1. The mean droplet size for the either adjuvant is ~400-500 nm. All of the components of the nanoemulsion are included on the FDA inactive ingredient list for Approved Drug Products.

TABLE 1

Exemplary Nanoemulsion Formulations.

| Function | Nanoemulsion-Adjuvant |
|---|---|
| Aqueous Diluent | Purified Water, USP |
| Hydrophobic Oil (Core) | Soybean Oil, USP (super refined) |
| Organic Solvent | Dehydrated Alcohol, USP (anhydrous ethanol) |
| Surfactant | Polysorbate 80, NF |
| Emulsifying Agent | Cetylpyridinium Chloride (CPC), USP or |
| Preservative | Dioctadecyldimethylammonium chloride (DODAC) |

The nanoemulsion adjuvants may be formed by emulsification of an oil, purified water, nonionic detergent, organic solvent and surfactant, such as a cationic surfactant. An exemplary specific nanoemulsion adjuvant is designated as "60% W805EC" or 60% DODAC NE". The 60% W805EC-vaccine adjuvant or 60% DODAC-vaccine adjuvant is composed of the ingredients shown in Table 2, below: purified water, USP; soybean oil USP; Dehydrated Alcohol, USP [anhydrous ethanol]; Polysorbate 80, NF, cetylpyridinium chloride, USP (CPC) and/or dioctadecyldimethylammonium chloride (DODAC). All components of this exemplary nanoemulsion adjuvant are included on the FDA list of approved inactive ingredients for Approved Drug Products.

TABLE 2

Composition of 60% W805EC-Adjuvant (w/w %).

| Ingredients | 60% W$_{80}$5EC | 60% DODAC NE |
|---|---|---|
| Purified Water, USP | 54.10% | 54.10% |
| Soybean Oil, USP | 37.67% | 37.67% |
| Dehydrated Alcohol, USP (anhydrous ethanol) | 4.04% | 4.04% |
| Polysorbate 80, NF | 3.55% | 3.55% |
| Cetylpyridinium Chloride (CPC), USP | 0.64% | — |
| Dioctadecyldimethylammonium chloride (DODAC) | — | 0.64% |

For the purposes of the present disclosure, a nanoemulsion as provided here (e.g. W805EC or DODAC NE) can make up between 1-99% (w/w %) of an immunogenic composition (e.g., a vaccine composition) of the disclosure. For instance, the nanoemulsion can be about 1, about 5, about 10, about 15, about 20, about 25, about 30, about 35, about 40, about 45, about 50, about 55, about 60, about 65, about 70, about 75, about 80, about 85, about 90, about 95, or about 99% of a vaccine formulation of the disclosure.

Pharmaceutical Compositions. Immunogenic compositions of the present disclosure may be formulated into pharmaceutical compositions, such as a vaccine, that are administered in a therapeutically effective amount to a subject and may further comprise suitable, pharmaceutically-acceptable excipients, additives, or preservatives. Suitable excipients, additives, and preservatives are well known in the art.

By the phrase "therapeutically effective amount" it is meant any amount of the composition that is effective in preventing, treating, or ameliorating a disease, pathogen, malignancy, or condition associated with the protein or antigen present in immunogenic composition. By "protective immune response" it is meant that the immune response is associated with prevention, treating, or amelioration of a disease. Complete prevention is not required, though is encompassed by the present disclosure. The immune response can be evaluated using the methods discussed herein or by any method known by a person of skill in the art.

The pharmaceutical compositions may be formulated for immediate release, sustained release, controlled release, delayed release, or any combinations thereof, into the epidermis or dermis. In some embodiments, the formulations may comprise a penetration-enhancing agent. Suitable penetration-enhancing agents include, but are not limited to, alcohols such as ethanol, triglycerides and aloe compositions. The amount of the penetration-enhancing agent may comprise from about 0.5% to about 40% by weight of the formulation.

In one aspect of the disclosure, the invention relates to a method for vaccination against, or for prophylaxis or therapy (prevention or treatment) of exposure to, infection with, or poisoning by a pathogen (e.g., a bacterial, viral, and/or fungal pathogen) via administration of a therapeutically or prophylactically effective amount of (a pharmaceutical composition comprising) an immunogenic composition of the disclosure as defined above, or obtainable as defined herein, to a subject in need of prophylaxis or therapy.

An immunogenic compositions of the present disclosure can be administered by any suitable route of administration. It will also be appreciated that the preferred route will vary with the condition and age of the recipient, and the disease being treated.

For example, the compositions can be administered by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration. Non-limiting examples of carriers include phosphate buffered saline (PBS), saline or a biocompatible matrix material such as a decellularized liver matrix (DCM as disclosed in Wang et al. (2014) J. Biomed. Mater Res. A. 102(4):1017-1025) for topical or local administration. The compositions can optionally contain a protease inhibitor, glycerol and/or dimethyl sulfoxide (DMSO).

The compositions can be conveniently presented in dosage unit form and can be prepared by any of the methods well known in the art of pharmacy. The compositions can be, for example, prepared by uniformly and intimately bringing the active ingredient into association with a liquid carrier, a finely divided solid carrier or both, and then, if necessary, shaping the product into the desired formulation. In the composition the protein or peptide is included in an amount sufficient to produce the desired therapeutic effect. For example, pharmaceutical compositions of the disclosure may take a form suitable for virtually any mode of administration, including, for example, topical, ocular, oral, buccal, systemic, nasal, injection, transdermal, rectal, and vaginal, or a form suitable for administration by inhalation or insufflation.

Intranasal administration is a particularly preferred mode of administration that includes administration via the nose, either with or without concomitant inhalation during administration. Such administration is typically through contact by the pharmaceutical composition comprising the nanoemulsion composition with the nasal mucosa, nasal turbinates or sinus cavity. Administration by inhalation comprises intranasal administration, or may include oral inhalation. Such administration may also include contact with the oral mucosa, bronchial mucosa, and other epithelia.

However, the disclosure is not limited to intranasal administration and pharmaceutical compositions of the disclosure may be administered by alternative means, like oral or injectable administration, as well. Useful injectable preparations include sterile suspensions, solutions, or emulsions of the active compound(s) in aqueous or oily vehicles. The compositions may also contain formulating agents, such as suspending, stabilizing, and/or dispersing agents. The formulations for injection can be presented in unit dosage form, e.g., in ampules or in multidose containers, and may contain added preservatives.

Compositions intended for oral use can be prepared according to any method known to the art for the manufacture of pharmaceutical compositions, and such compositions may contain one or more agents selected from the group consisting of sweetening agents, flavoring agents, coloring agents, and preserving agents in order to provide pharmaceutically elegant and palatable preparations. Tablets contain the active ingredient (including drug and/or prodrug) in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch or alginic acid); binding agents (e.g., starch, gelatin, or acacia); and lubricating agents (e.g., magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They may also be coated by the techniques described in the U.S. Pat. Nos. 4,256,108; 4,166,452; and U.S. Pat. No. 4,265,874 to form osmotic therapeutic tablets for control release. The pharmaceutical compositions of the disclosure may also be in the form of oil-in-water emulsions.

Liquid preparations for oral administration may take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin, or acacia); non-aqueous vehicles (e.g., almond oil, oily esters, ethyl alcohol, Cremophore™, or fractionated vegetable oils); and preservatives (e.g., methyl or propyl-p-hydroxybenzoates or sorbic acid). The preparations may also contain buffer salts, preservatives, flavoring, coloring, and sweetening agents as appropriate.

Exemplary dosage forms for pharmaceutical administration are described herein. Examples include but are not limited to liquids, ointments, creams, emulsions, lotions, gels, bioadhesive gels, sprays, aerosols, pastes, foams, sunscreens, capsules, microcapsules, suspensions, pessary, powder, semi-solid dosage form, etc.

The immunogenic compositions can likewise be applied and/or delivered utilizing electrophoretic delivery/electrophoresis. Further, the compositions may be applied by a transdermal delivery system such as a patch or administered by a pressurized or pneumatic device (i.e., "gene gun"). Such methods, which comprise applying an electrical current, are well known in the art.

The pharmaceutical compositions for administration may be applied in a single administration or in multiple administrations.

If applied topically, the compositions may be occluded or semi-occluded. Occlusion or semi-occlusion may be performed by overlaying a bandage, polyoleofin film, article of clothing, impermeable barrier, or semi-impermeable barrier to the topical preparation.

The present disclosure contemplates that many variations of the describe compositions will be useful in the methods of the present disclosure. To determine if a candidate composition is suitable for pharmaceutical use, three criteria are analyzed. Using the methods and standards described herein, candidate compositions can be easily tested to determine if they are suitable. First, the desired ingredients are prepared using the methods described herein, to determine if a buffer-stabilized compositions can be formed. If a buffer-stabilized compositions cannot be formed, the candidate is rejected. Second, the candidate buffer-stabilized compositions should be stable. A buffer-stabilized composition is stable if it remains in solution, with the biological activity of a protein or peptide preserved for a sufficient period to allow for its intended use. For example, for pharmaceutical buffer-stabilized compositions that are to be stored, shipped, etc., it may be desired that the buffer-stabilized composition remain in solution form for months to years. Typical buffer-stabilized compositions that are relatively unstable, will lose their form within a day. Third, the candidate pharmaceutical buffer-stabilized compositions should have efficacy for its intended use. For example, the pharmaceutical buffer-stabilized compositions disclosed herein should induce a protective immune response or a therapeutic effect to a detectable level.

The disclosed compositions can be provided in many different types of containers and delivery systems. For example, in some embodiments of the disclosed, the compositions are provided in a cream or other solid or semi-solid form. The disclosed compositions may be incorporated into hydrogel formulations.

The compositions can be delivered (e.g., to a subject or customers) in any suitable container. Suitable containers can be used that provide one or more single use or multi-use dosages of the vaccines for the desired application. In some embodiments of the disclosed, the compositions are provided in a suspension or liquid form. Such compositions can be delivered in any suitable container including spray bottles and any suitable pressurized spray device. Such spray bottles may be suitable for delivering the compositions intranasally or via inhalation. These containers can further be packaged with instructions for use to form kits.

Formulation Techniques

Nanoemulsions of the present invention can be formed using classic emulsion forming techniques. In brief, the oil phase is mixed with the aqueous phase under relatively high shear forces (e.g., using high hydraulic and mechanical forces) to obtain an oil-in-water nanoemulsion. The emulsion is formed by blending the oil phase with an aqueous phase on a volume-to-volume basis ranging from about 1:9 to 5:1, preferably about 5:1 to 3:1, most preferably 4:1, oil phase to aqueous phase. The oil and aqueous phases can be blended using any apparatus capable of producing shear forces sufficient to form an emulsion such as French Presses or high shear mixers (e.g., FDA approved high shear mixers are available, for example, from Admix, Inc., Manchester, N.H.). Methods of producing such emulsions are described in U.S. Pat. Nos. 5,103,497 and 4,895,452, and U.S. Patent Application Nos. 20070036831, 20060251684, and 20050208083, herein incorporated by reference in their entireties.

In preferred embodiments, compositions used in the methods of the present invention comprise droplets of an oily discontinuous phase dispersed in an aqueous continuous phase, such as water. In preferred embodiments, nanoemulsions of the present invention are stable, and do not decompose even after long storage periods (e.g., greater than one or more years). Furthermore, in some embodiments, nanoemulsions are stable (e.g., in some embodiments for greater than 3 months, in some embodiments for greater than 6 months, in some embodiments for greater than 12 months, in some embodiments for greater than 18 months) after combination with an immunogen. In preferred embodiments, nanoemulsions of the present invention are non-toxic and safe when administered (e.g., via spraying or contacting mucosal surfaces, swallowed, inhaled, etc.) to a subject.

In some embodiments, a portion of the emulsion may be in the form of lipid structures including, but not limited to, unilamellar, multilamellar, and paucilamellar lipid vesicles, micelles, and lamellar phases.

In general, the preferred non-toxic nanoemulsions are characterized by the following: they are approximately 200-800 nm in diameter, although both larger and smaller diameter nanoemulsions are contemplated; the charge depends on the ingredients; they are stable for relatively long periods of time (e.g., up to two years); they are non-irritant and non-toxic compared to their individual components due, at least in part, to their oil contents that markedly reduce the toxicity of the detergents and the solvents; they are effective at concentrations as low as, for example, 0.1%.

The present invention is not limited by the type of subject administered (e.g., in order to stimulate an immune response (e.g., in order to generate protective immunity (e.g., mucosal and/or systemic immunity))) a composition of the present invention. Indeed, a wide variety of subjects are contemplated to be benefited from administration of a composition of the present invention. In preferred embodiments, the subject is a human. In some embodiments, human subjects are of any age (e.g., adults, children, infants, etc.) that have been or are likely to become exposed to a microorganism (e.g., a pathogenic microorganism). In some embodiments, the human subjects are subjects that are more likely to receive a direct exposure to pathogenic microorganisms or that are more likely to display signs and symptoms of disease after exposure to a pathogen (e.g., immune suppressed subjects). In some embodiments, the general public is administered (e.g., vaccinated with) a composition of the present invention (e.g., to prevent the occurrence or spread of disease). For example, in some embodiments, compositions and methods of the present invention are utilized to vaccinate a group of people (e.g., a population of a region, city, state and/or country) for their own health (e.g., to prevent or treat disease). In some embodiments, the subjects are non human mammals (e.g., pigs, cattle, goats, horses, sheep, or other livestock; or mice, rats, rabbits or other animal). In some embodiments, compositions and methods of the present invention are utilized in research settings (e.g., with research animals).

In preferred embodiments, an immunogenic composition of the present invention comprises a suitable amount of the antigen/immunogen to induce an immune response in a subject when administered to the subject. In preferred embodiments, the immune response is sufficient to provide the subject protection (e.g., immune protection) against a subsequent exposure to the immunogen or the microorganism (e.g., bacteria or virus) from which the immunogen was derived. The present invention is not limited by the amount of immunogen used. In some preferred embodiments, the amount of immunogen (e.g., protein antigen) in an immunogenic composition (e.g., for use as an immunization dose) is selected as that amount which induces an immunoprotective response without significant, adverse side effects. The amount will vary depending upon which specific immunogen or combination thereof is/are employed, and can vary from subject to subject, depending on a number of factors including, but not limited to, the species, age and general condition (e.g., health) of the subject, and the mode of administration. Procedures for determining the appropriate amount of immunogen administered to a subject to elicit an immune response (e.g., a protective immune response (e.g., protective immunity)) in a subject are well known to those skilled in the art.

In some embodiments, it is expected that each dose (e.g., of an immunogenic composition (e.g., administered to a subject to induce an immune response (e.g., a protective immune response (e.g., protective immunity))) comprises 0.05-5000 µg of each immunogen (e.g., recombinant and/or purified protein), in some embodiments, each dose will comprise 1-500 µg, in some embodiments, each dose will comprise 350-750 µg, in some embodiments, each dose will comprise 50-200 µg, in some embodiments, each dose will comprise 25-75 µg of immunogen (e.g., recombinant and/or purified protein). In some embodiments, each dose comprises an amount of the immunogen sufficient to generate an immune response. An effective amount of the immunogen in a dose need not be quantified, as long as the amount of immunogen generates an immune response in a subject when administered to the subject. An optimal amount for a particular administration (e.g., to induce an immune response (e.g., a protective immune response (e.g., protective immunity))) can be ascertained by one of skill in the art using standard studies involving observation of antibody titers and other responses in subjects.

In some embodiments, it is expected that each dose (e.g., of an immunogenic composition (e.g., administered to a subject to induce and immune response)) is from 0.001 to 15% or more (e.g., 0.001-10%, 0.5-5%, 1-3%, 2%, 6%, 10%, 15% or more) by weight immunogen (e.g., neutralized bacteria or virus, or recombinant and/or purified protein). In some embodiments, an initial or prime administration dose contains more immunogen than a subsequent boost dose.

In some embodiments, an immunogenic composition of the present invention is formulated in a concentrated dose that can be diluted prior to administration to a subject. For example, dilutions of a concentrated composition may be administered to a subject such that the subject receives any one or more of the specific dosages provided herein. In some embodiments, dilution of a concentrated composition may be made such that a subject is administered (e.g., in a single dose) a composition comprising about 0.1-50% of the nanoemulsion adjuvant present in the concentrated composition. In some preferred embodiments, a subject is administered in a single dose a composition comprising 1% of the NE present in the concentrated composition. Concentrated compositions are contemplated to be useful in a setting in which large numbers of subjects may be administered a composition of the present invention (e.g., an immunization clinic, hospital, school, etc.). In some embodiments, an immunogenic composition of the present invention (e.g., a concentrated composition) is stable at room temperature for more than 1 week, in some embodiments for more than 2 weeks, in some embodiments for more than 3 weeks, in some embodiments for more than 4 weeks, in some embodiments for more than 5 weeks, and in some embodiments for more than 6 weeks.

Generally, an immunogenic composition comprising an emulsion of the invention will comprise at least 0.001% to 100%, preferably 0.01 to 90%, of emulsion per ml of liquid composition. It is envisioned that the formulations may comprise about 0.001%, about 0.0025%, about 0.005%, about 0.0075%, about 0.01%, about 0.025%, about 0.05%, about 0.075%, about 0.1%, about 0.25%, about 0.5%, about 1.0%, about 2.5%, about 5%, about 7.5%, about 10%, about 12.5%, about 15%, about 20%, about 25%, about 30%, about 35%, about 40%, about 50%, about 55%, about 60%, about 65%, about 70%, about 75%, about 80%, about 85%, about 90%, about 95% or about 100% of emulsion per ml of liquid composition. It should be understood that a range between any two figures listed above is specifically contemplated to be encompassed within the metes and bounds of the present invention. Some variation in dosage will necessarily occur depending on the condition of the specific pathogen and the subject being immunized.

In some embodiments, following an initial administration of a composition of the present invention (e.g., an initial vaccination), a subject may receive one or more boost administrations (e.g., around 2 weeks, around 3 weeks, around 4 weeks, around 5 weeks, around 6 weeks, around 7 weeks, around 8 weeks, around 10 weeks, around 3 months, around 4 months, around 6 months, around 9 months, around 1 year, around 2 years, around 3 years, around 5 years, around 10 years) subsequent to a first, second, third, fourth, fifth, sixth, seventh, eighth, ninth, tenth, and/or more than tenth administration. Although an understanding of the mechanism is not necessary to practice the present invention and the present invention is not limited to any particular mechanism of action, in some embodiments, reintroduction of an immunogen in a boost dose enables vigorous systemic immunity in a subject. The boost can be with the same formulation given for the primary immune response, or can be with a different formulation that contains the immunogen. The dosage regimen will also, at least in part, be determined by the need of the subject and be dependent on the judgment of a practitioner.

Dosage units may be proportionately increased or decreased based on several factors including, but not limited to, the weight, age, and health status of the subject. In addition, dosage units may be increased or decreased for subsequent administrations (e.g., boost administrations).

It is contemplated that the compositions and methods of the present invention will find use in various settings, including research settings. For example, compositions and methods of the present invention also find use in studies of the immune system (e.g., characterization of adaptive immune responses (e.g., protective immune responses (e.g., mucosal or systemic immunity))). Uses of the compositions and methods provided by the present invention encompass human and non-human subjects and samples from those subjects, and also encompass research applications using these subjects. Compositions and methods of the present invention are also useful in studying and optimizing nanoemulsions, immunogens, and other components and for screening for new components. Thus, it is not intended that the present invention be limited to any particular subject and/or application setting.

In some embodiments, the present invention provides a kit comprising an immunogenic composition. In some embodiments, the kit further provides a device for administering the composition. The present invention is not limited by the type of device included in the kit. In some embodiments, the device is configured for nasal application of the composition of the present invention (e.g., a nasal applicator (e.g., a syringe) or nasal inhaler or nasal mister). In some embodiments, a kit comprises a composition comprising a nanoemulsion adjuvant in a concentrated form (e.g., that can be diluted prior to administration to a subject).

In some embodiments, all kit components are present within a single container (e.g., vial or tube). In some embodiments, each kit component is located in a single container (e.g., vial or tube). In some embodiments, one or more kit component are located in a single container (e.g., vial or tube) with other components of the same kit being located in a separate container (e.g., vial or tube). In some embodiments, a kit comprises a buffer. In some embodiments, the kit further comprises instructions for use.

EXAMPLES

The following examples serve to illustrate certain preferred embodiments and aspects of the present invention and are not to be construed as limiting the scope thereof.

In the experimental disclosure which follows, the following abbreviations apply: eq (equivalents); µ (micron); M (Molar); µM (micromolar); mM (millimolar); N (Normal); mol (moles); mmol (millimoles); µmol (micromoles); nmol (nanomoles); g (grams); mg (milligrams); µg (micrograms); ng (nanograms); L (liters); ml (milliliters); µl (microliters); cm (centimeters); mm (millimeters); µm (micrometers); nM (nanomolar); ° C. (degrees Centigrade); and PBS (phosphate buffered saline).

Example 1 rH5 Antigen, QS-21, CpG and Nanoemulsion

A series of experiments were generated and conducted in order to identify and characterize the adjuvant properties of various different emulsion delivery systems in combination with different immunostimulatory compounds. In particular, experiments were conducted during development of embodiments of the invention in order to evaluate the combination of 3 different adjuvants, a TLR9 agonist, composed of synthetic oligodeoxynucleotides (ODN) containing immunostimulatory CpG motifs (CpG), a QS-21 and nanoemulsion adjuvant, composed of two surfactants, oil, and organic solvent, which possesses both immunostimulatory and delivery properties. While individual adjuvant members have previously been documented to be effective adjuvants, there exists no report or data in the field indicating what might happen to the adjuvant properties of each individual adjuvant member if the members are combined.

Accordingly, combinations of various TLR agonists and nanoemulsion adjuvant (NE) formulations were evaluated for adjuvant activity when used in combination with antigen/immunogen as described below.

Materials and Methods. rH5 was obtained from Fraunhofer USA Center for Molecular Biotechnology, Newark Del. Briefly, the recombinant rH5 protein was expressed in tobacco plants by *Agrobacterium* gene transfer. The transgene encoding amino acids 17-532 of the HA gene of the A/Indonesia/05/2005 (H5N1) virus was cloned into a plasmid vector. This vector was transformed into *Agrobacterium tumefaciens*. The transformed bacteria were cultured overnight and subsequently vacuum infiltrated into 6-week-old *Nicotiana benthamiana* plants. After seven days, leaves were harvested and homogenized, the extracts were clarified by centrifugation, and the HA protein was purified by immobilized metal affinity chromatography and anion exchange chromatography.

Purified QS-21 was purchased from Desert King International (San Diego, Calif., USA). ODN 1826 is a CpG oligodeoxynucleotides (ODN) class B ODN specific for murine TLR9. B-class CpG ODNs contain a full phosphorothioate backbone with one or more CpG dinucleotides. They strongly activate B cells but weakly stimulate IFN-α secretion. ODN 1826 VACCIGRADE™ is a preclinical grade preparation of the CpG ODN 1826. It is tested for sterility and the presence of endotoxins. ODN 1826 VACCIGRADE™ is guaranteed sterile and its endotoxin level is <1 EU/mg (measurement by kinetic chromogenic LAL assay). ODN1826 sequence: 5'-tccatgacgttcctgacgtt-3' (20 mer) was purchased from In vivo Gen (San Diego, Calif., USA).

Phosphate-buffered saline was purchased from Sigma Chemical Company (Saint Louis, Mo., USA).

The nanoemulsion adjuvants were formed by emulsification of an oil, purified water, nonionic detergent, organic solvent and surfactant, such as a cationic surfactant. An exemplary specific nanoemulsion adjuvant is designated as "60% W805EC" or 60% DODAC NE". The 60% W805EC-vaccine adjuvant or 60% DODAC-vaccine adjuvant is composed of the ingredients shown in Table 3 below: purified water, USP; soybean oil USP; Dehydrated Alcohol, USP [anhydrous ethanol]; Polysorbate 80, NF, cetylpyridinium chloride, USP (CPC) and/or dioctadecyldimethylammonium chloride (DODAC). All components of this exemplary nanoemulsion adjuvant are included on the FDA list of approved inactive ingredients for Approved Drug Products.

TABLE 3

Composition of 60% W805EC-Adjuvant (w/w %)

| Ingredients | 60% $W_{80}5EC$ | 60% DODAC NE | 60% DODAC/ CPC NE |
|---|---|---|---|
| Purified Water, USP | 54.10% | 54.10% | 54.10% |
| Soybean Oil, USP | 37.67% | 37.67% | 37.67% |
| Dehydrated Alcohol, USP (anhydrous ethanol) | 4.04% | 4.04% | 4.04% |

TABLE 3-continued

Composition of 60% W805EC-Adjuvant (w/w %)

| Ingredients | 60% $W_{80}5EC$ | 60% DODAC NE | 60% DODAC/ CPC NE |
|---|---|---|---|
| Polysorbate 80, NF | 3.55% | 3.55% | 3.55% |
| Cetylpyridinium Chloride (CPC), USP | 0.64% | — | 0.32% |
| Dioctadecyldimethylammonium chloride (DODAC) | — | 0.64% | 0.32% |

Combinations of various TLR agonists and nanoemulsion adjuvant (NE) formulations were generated and tested for adjuvant activity. Specifically, formulations were prepared and tested for potential adjuvant activity for inducing immune responses upon an intramuscular route of administration. Immune responses analyzed/characterized included production of hemagglutination-inhibition (HAI) antibody titers and viral neutralizing (VN) antibody titers, both of which provide an indication of the functional components of an induced immune response. Various formulations were generated (See Table 4) and tested. It is noted that a cut-off for geometric mean titer (GMT) of ≥1:40 for HAI is accepted in the art as a correlate of protection against influenza.

TABLE 4

Evaluation of W805EC adjuvant in combination with QS21 or CpG ODN, or using nanoemulsions formulated with DODAC cationic surfactant by the intramuscular route in CD-1 mice.

| Group/F# | Description | Amount (μg) of rH5 antigen per 50 μL IM dose | Additional Adjuvant amount (μg) per 50 μL IM dose |
|---|---|---|---|
| First Set Exploratory Formulations | | | |
| 1 | QS-21 (alone) | 10 μg | QS-21: 10 μg |
| 2 | 5% $W_{80}5EC$ + QS-21 | 10 μg | QS-21: 10 μg |
| 3 | 5% DODAC NE | 10 μg | — |
| 4 | 5% DODAC/CPC NE | 10 μg | — |
| 5 | CpG (alone) | 10 μg | CpG: 10 μg |
| 6 | 5% $W_{80}5EC$ + CpG | 10 μg | CpG: 10 μg |
| 7 | rH5 | 10 μg | 0 |
| 8 | No Treatment (Naïve) | 0 | 0 |
| Second Set of Exploratory Formulations | | | |
| 1 | 5% $W_{80}5EC$ + CpG | 10 μg | CpG: 20 μg |
| 2 | 5% DODAC NE + CpG | 10 μg | CpG: 20 μg |
| 3 | 5% DODAC NE | 10 μg | — |
| 4 | CpG (alone) | 10 μg | CpG: 20 μg |
| 5 | 5% DODAC NE + CpG | 10 μg | CpG: 10 μg |
| 6 | CpG (alone) | 10 μg | CpG: 10 μg |
| 7 | 5% DODAC NE + CpG | 10 μg | CpG: 5 μg |
| 8 | CpG (alone) | 10 μg | CpG: 5 μg |
| 9 | 5% DODAC NE + CpG | 5 μg | CpG: 10 μg |
| 10 | CpG (alone) | 5 μg | CpG: 10 μg |

Animals were vaccinated as follows: PBS; rH5: (10 μg/animal); 8 animals per group/64 animals; Three IM immunizations each delivered in a volume of 50121 at 0, 2, and 4 wks; Sacrifice at week 6. Briefly, the mixing protocol for a 700 μL batch size of a test vaccine formulation comprised of mixing three or four components, the volume of each constituent in each test formulations is shown in Table 5. A PBS solution was mixed gently with 5.8 mg/mL rH5 antigen solution. The nanoemulsion adjuvant, either 60% W805EC, 60% DODAC/CPC NE or 60% DODAC NE was than added and mixed gently. CpG (1 mg/ml) solution or QS-21 (1 mg/ml) solution was added last and mixed gently. The test vaccine formulation contained rH5 antigen and 5% nanoemulsion adjuvant with or without CpG or QS-21 in PBS (1×).

ing enzyme (RDE, Denka-Seiken) at 37° C. followed by heat inactivation of RDE at 56° C. and storage at 4° C. during analysis. The assays used A/Indonesia/05/05 (xPR8 IBCDC RG-2 from CDC) virus and 1% horse red blood cells. Serum dilutions started at 1:20 and samples without detectable HAI activity were assigned a value of 10.

TABLE 5

Composition of vaccine formulations of nanoemulsion adjuvant in combination with QS-21 or CpG ODN.

| Group | Description | Volume of PBS (µL) in 700 µL | Volume of 5.8 mg/mL rH5 solution (µL) in 700 µL | Volume of 60% NE (µL) in 700 µL | Volume of 1 mg/ml CpG or 1 mg/ml QS-21 solution (µL) in 700 µL |
|---|---|---|---|---|---|
| | First Set Exploratory Formulations | | | | |
| 1 | QS-21 (alone) | 536 | 24 | — | 140 |
| 2 | 5% $W_{80}5EC$ + QS-21 | 478 | 24 | 58 | 140 |
| 3 | 5% DODAC NE | 618 | 24 | 58 | — |
| 4 | 5% DODAC/CPC NE | 618 | 24 | 58 | — |
| 5 | CpG (alone) | 396 | 24 | 0 | 280 |
| 6 | 5% $W_{80}5EC$ + CpG | 338 | 24 | 58 | 280 |
| 7 | rH5 | 676 | 24 | — | — |
| 8 | No Treatment (Naïve) | — | — | — | — |
| | Second Set of Exploratory Formulations | | | | |
| 1 | 5% $W_{80}5EC$ + CpG | 338 | 24 | 58 | 280 |
| 2 | 5% DODAC NE + CpG | 338 | 24 | 58 | 280 |
| 3 | 5% DODAC NE | 618 | 24 | 58 | — |
| 4 | CpG (alone) | 396 | 24 | 58 | 280 |
| 5 | 5% DODAC NE + CpG | 478 | 24 | 58 | 140 |
| 6 | CpG (alone) | 536 | 24 | 58 | 140 |
| 7 | 5% DODAC NE + CpG | 548 | 24 | 58 | 70 |
| 8 | CpG (alone) | 606 | 24 | — | 70 |
| 9 | 5% DODAC NE + CpG | 490 | 12 | 58 | 140 |
| 10 | CpG (alone) | 548 | 12 | — | 140 |

Figure 9:
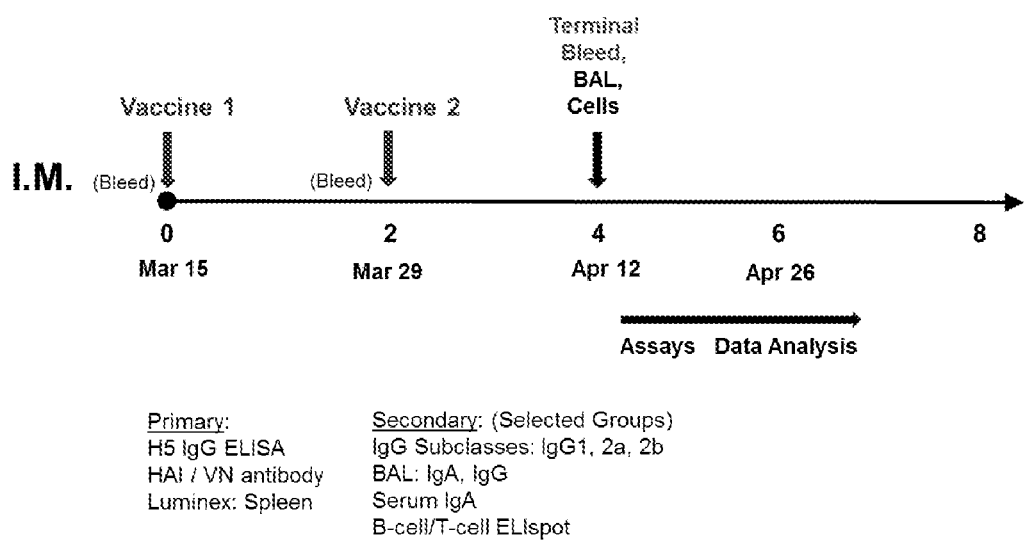
FIG. 9 show the experimental timeline for evaluation of DODAC+CpG ODN nanoemulsion combination adjuvant in CD-1 mice. Buffer system for vaccine formulation: PBS; rH5 (10 μg/animal); 8 animals per group/64 animals; Three IM immunizations each delivered in a volume of 50 μl at 0, 2, and 4 wks; Sacrifice at week 6.

Vaccinations. Six- to eight-week-old female CD-1 mice (6-8 wk; n=6-10/group) (Charles River Laboratories) were immunized twice (FIG. 9) or three times (FIG. 1) intramuscularly at 2 week intervals with 504, of test vaccine formulations. All test vaccine formulations at a dosing volume of 50 µL were administered by intramuscular (IM) injection in the left tibialis anterior (TA) muscle of mice lightly anaesthetized with Isoflurane (CDMV, Saint Hyacinthe, QC).

Mice were immunized at the intervals described above using rH5 antigen, either alone, or co-formulated with CpG, nanoemulsion, or nanoemulsion+CpG as described in Table 4. Naïve animals were used for comparison as controls.

Immune response assays. Animals were bled from the saphenous vein at various timepoints after immunization and antigen-specific total IgG, was measured in serum by endpoint ELISA (in triplicate) for individual animals, using 96-well plates coated with rHA (1 µg/well).

rH5-specific IgG ELISA. Serum was obtained from the saphenous vein every 2-weeks post-initial immunization, and anti-rH5 specific IgG end-titers were measured by ELISA. Briefly, serum samples were serially diluted in PBS with 0.1% BSA, and incubated on microtiter plates coated with 1 µg/mL rH5. ELISAs were developed with an alkaline phosphatase detection system, and quantified by measuring the optical density (OD) at 405 nm (OD405). Endpoint titers are reported as the reciprocal of the highest serum dilution giving an OD above a cutoff value (sum of OD of the same dilution of a control serum from an untreated mouse and two times the standard deviation).

Hemagglutination inhibition assay. Mouse serum samples from week 6 were analyzed using the HAI assay. Prior to analysis, serum samples were treated with receptor-destroy- Cell-mediated immunity. Spleens were removed aseptically at the time of sacrifice 2 weeks following the final immunization. Splenocytes were pelleted by centrifugation at 2000 rpm for 5 min and resuspended in ACK lysis buffer for <3 minutes to remove red blood cells (150 mM NH4Cl, 10 mM KHCO3, 0.1 mM EDTA). PBS was added to stop lysis, and cells were pelleted and washed again in PBS. The cell pellet was then resuspended in T-Cell media (DMEM supplemented with 5% FBS, 2 mM L-glutamine, 1× non-essential amino acids, 1 mM sodium pyruvate, 10 mM MOPS, 50 µM 2-mercaptoethanol, 100 IU penicillin, and 100 µg/mL streptomycin and filtered through a cell strainer. Splenocytes were then plated at a density of $4\times10^5$ cells/well in 96-well tissue culture plates and stimulated using 5 µg/ml rH5 antigen or medium alone. Cell-free supernatants were harvested after 72 hours culture at 37° C. Supernatants were stored at −80° C. prior to Luminex multiplex analysis (Millipore) to determine cytokine profiles using selected kits according to manufacturers' instructions (Milliplex Catalog ID. MCYTOMAG-70K-08. Mou).

Statistical Analysis. Data were analyzed using Graph-Pad Prism (GraphPad Software, San Diego, Calif.). Statistical significance of the difference between the two groups was calculated by Student's 2-tailed t-test and between three or more groups by 1-factor analysis of variance (ANOVA) followed by post hoc analysis.

Analytical Methods Used in the Short Term Stability Studies. The various formulations were filled into 1.8 mL Type 1 glass vials with a PTFE-lined screw cap. The stability parameters assessed for these formulations were physical appearance, pH, mean particle size, SDS-Page Gel for 70-80 kd. Dynamic light scattering using the Malvern Zetasizer was used to determine particle size, particle size distribution profiles and a polydispersity index. Acceptable criteria developed and considered for each criteria are depicted in Table 6.

TABLE 6

Test method and acceptance criteria for the formulations placed on informal stability.

| | | Acceptance Criteria for Each Formulation Type | |
|---|---|---|---|
| Stability Parameter | Test Method | Control Solution: rH5 + CpG | 20% $W_{80}5EC$ + rH5 +/− CpG |
| Physical Appearance | Visual | No Precipitation and/or Cloudy Solution | No Phase Separation |
| pH | pH Meter | +/−0.5 | +/−0.5 |
| Particle Size | Dynamic Light Scattering | — | Z-Ave: +/−200 nm |

TABLE 6-continued

Test method and acceptance criteria for the formulations placed on informal stability.

| | | Acceptance Criteria for Each Formulation Type | |
|---|---|---|---|
| Stability Parameter | Test Method | Control Solution: rH5 + CpG | 20% $W_{80}5EC$ + rH5 +/− CpG |
| PdI | Dynamic Light Scattering | Less than 0.25 | Less than 0.25 |
| rH5 Integrity | SDS Page Gel (kDa) | Band Present Profile compares to reference material | Band Present Profile compares to reference material |
| rH5 Potency | SRID | Concentration compares to reference material | Concentration compares to reference material |

Physical Appearance Test. Observations of physical appearance were recorded according to the nanoemulsion stability assessment criteria shown in Table 7. Physical appearance of the formulations was determined at the initial time point and upon various storage conditions.

TABLE 7

Nanoemulsion Stability Parameters, Description and Acceptance Criteria pH Assessment: The pH was measured using a standard pH meter with the appropriate probe that was used.

| Stability Parameter | Description | Acceptance Criteria | |
|---|---|---|---|
| Color | A white to off white liquid | A white to off white liquid acceptable. Yellow (light to dark), tan, and shades of brown not acceptable. | |
| Creaming | A white, creamy layer on top of the emulsion that is more opaque than the rest of the emulsion. Remixing will restore homogeneity. | Presence (+) or absence (−) All stages of creaming are acceptable | |
| Settling | A gradual decrease in opacity of the emulsion from top to bottom. Remixing will restore homogeneity. | Mild - cloudiness gradient from top to bottom (no defining layers) Moderate - clear at bottom of vial with increasing opacity toward the cap Severe - 3-4 distinct layers Extreme - only 2 layers All stages of settling are acceptable | |
| Phase Separation | Separation of the oil and water phases of the emulsion. Remixing will not restore homogeneity. | Pass: None Insignificant - a few droplets are visible at surface Mild - oil layer equals <1% of total height | Fail: Moderate - a film of oil >1% of emulsion height Severe - 3 distinct layers Extreme - total separation into 2 phases (oil and water) |

Mean Particle Size Analysis and Polydispersity Index (PdI): The mean particle size (Z-average) and polydispersity index (PdI) were determined for all the stability samples. The particle size and PdI of the sample was measured by photon correlation spectroscopy using a Malvern Zetasizer Nano ZS90 (Malvern Instruments, Worcestershire, UK), according to the Malvern user's manual for Particle Sizing (Malvern). All measurements were carried out at 25° C. after dilution to 1% nanoemulsion with sterile water. The aqueous systems were not diluted.

Sodium Dodecyl Sulfate-Polyacrylamide Gel Electrophoresis Method for rH5: The nanoemulsion vaccine samples containing rH5 antigen, or rH5 antigen alone, were prepared by acetone precipitation at (−)20° C. for 60 minutes to remove nanoemulsion while precipitating the antigen for subsequent SDS-PAGE analysis (Invitrogen Xcell mini-gel electrophoresis System). After precipitation, the samples were spun for 15 minutes at 14,000×g and the supernatant was removed. The slightly dried pellet was resuspended in 50 ul of 1× sample buffer (Thermo 39000, lot #PJ207541) and incubated at 4° C. for 2 hours. The samples next were mixed by pipetting up and down followed by −20° C. storage. Samples (5 ul per lane, 1 ug rH5 antigen per lane) were loaded onto a Criterion™ XT, 12% Bis-Tris, 18 well, gel (BioRad Cat #345-0118) and run at 120 volts using XT MES, (Biorad 161-0789) running buffer until the dye front reached the end of the gel. Gels were stained at room temperature for 2 hours using Imperial™ Protein Stain, (ThermoScientific, Cat #24615), followed by destaining overnight in water. Precision Plus markers (BioRad) were used as a standard to assess molecular weight.

Formulations as shown in Table 8 were administered to mice according to the schedule shown in FIG. 1.

TABLE 8

Evaluation of $W_{80}5EC$ adjuvant in combination with QS21 or CpG ODN, or using nanoemulsions formulated with DODAC cationic surfactant by the intramuscular route in CD-1 mice.

Figure 2:
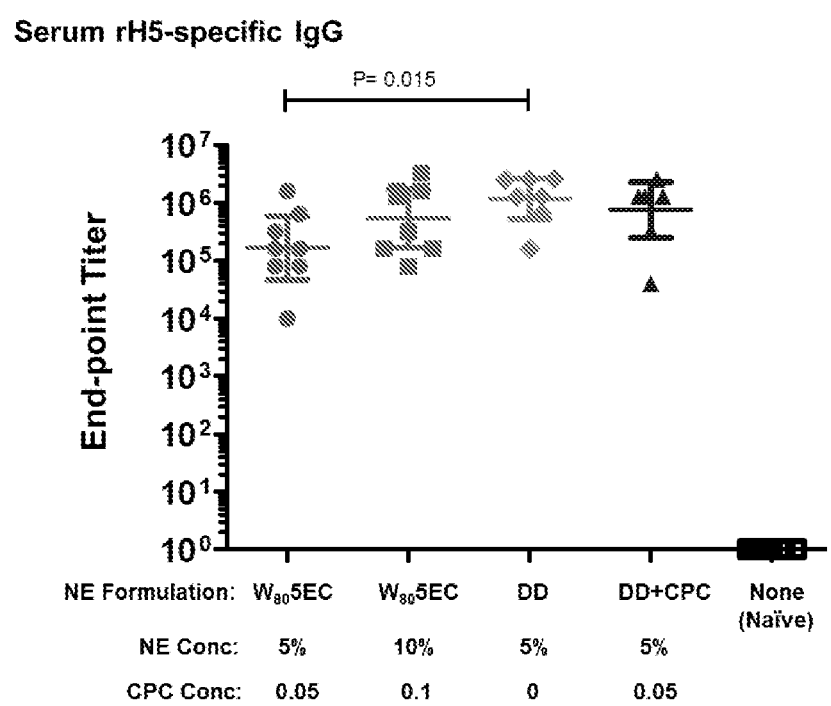
FIG. 2 shows endpoint rH5-specific IgG titers upon intramuscular administration using adjuvant formulations detailed in Table 8. Serum rH5-specific IgG was determined by ELISA at week 4 (2 weeks post-second immunization).
Figure 3:
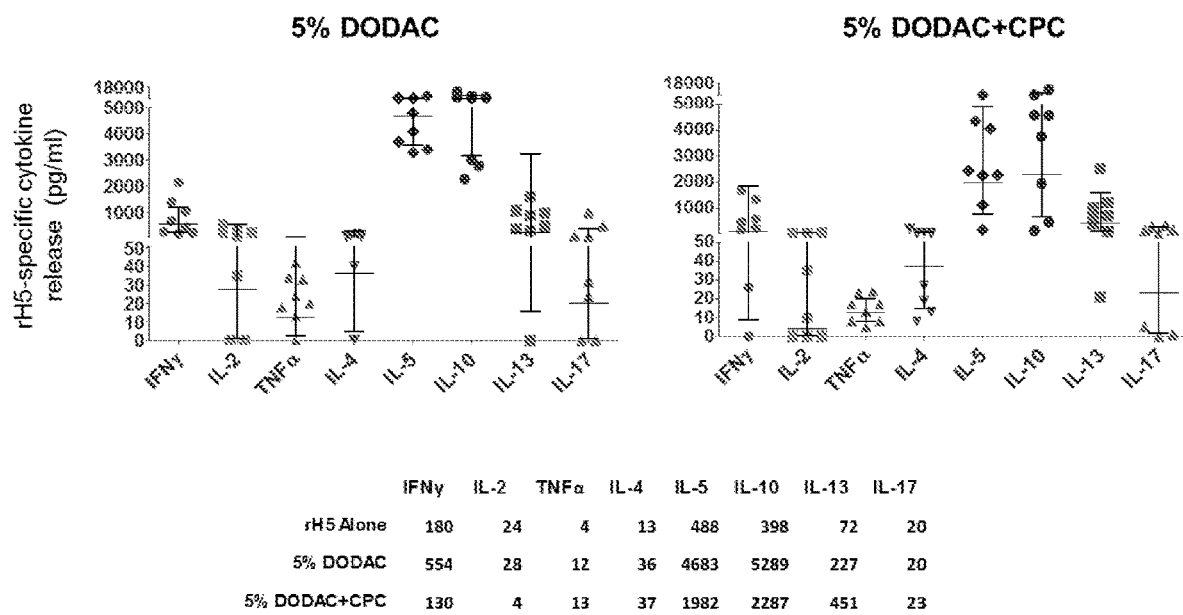
FIG. 3 shows cytokine release profiles for I. M. nanoemulsion dose range experiments: Comparison of the 5% DODAC (single cationic surfactant) vs. 5% DODAC+CPC (dual cationic surfactant) adjuvant formulations.

| Group | Description | Amount of rH5 per each Immunization (µg per 50 µL dose) | Adjuvant System Concentration or Amount (µg) per 50 µL IM dose |
|---|---|---|---|
| 1 | QS-21 | 10 | QS-21 (10 µg) |
| 2 | NE + QS-21 | 10 | 5% $W_{80}5EC$ NE + QS-21 (10 µg) |
| 3 | DODAC NE | 10 | 5% DODAC NE |
| 4 | DODAC/CPC NE | 10 | 5% DODAC/CPC NE |
| 5 | CpG | 10 | CpG (10 µg) |
| 6 | NE + CpG | 10 | 5% $W_{80}5EC$ NE + CpG (20 µg) |
| 7 | Antigen Alone | 10 | — |
| 8 | Naive | 0 | — | rH5-specific serum IgG in treatment groups assessing a single cationic DODAC formulation (Group 3) were compared to dual cationic formulation (5% DODAC/CPC NE) (Group 4) using serum obtained 2 weeks following the second intramuscular vaccination (See FIG. 2). Interestingly, the geometric mean titer (GMT) of rH5-specific serum IgG was highest in the group immunized using the DODAC single-cationic formulation (GMT: $1.17 \times 10^6$) compared to W805EC (GMT: $1.65 \times 10^5$) (P=0.015). The dual cationic combination of CPC+DODAC (GMT: $7.61 \times 10^5$) was not significantly different than DODAC alone (GMT: $1.17 \times 10^6$). Addition of the CPC cationic surfactant to the DODAC formulation did not enhance the cytokine response compared to DODAC alone (See FIG. 3).

Groups of CD-1 mice were immunized intramuscularly in a series of three vaccinations at 2 week intervals. Mice were sacrificed 2 weeks after the final immunization (Week 6) for evaluation of serum antibodies and rH5-specific cytokine release by spleen cells.

Figure 4:
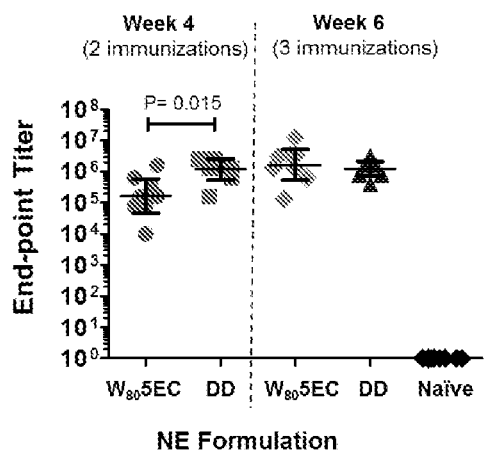
FIG. 4 shows evaluation of serum rH5-specific antibody responses after intramuscular immunization of CD-1 mice using nanoemulsion formulations containing CPC or DODAC (DD).
Figure 4:
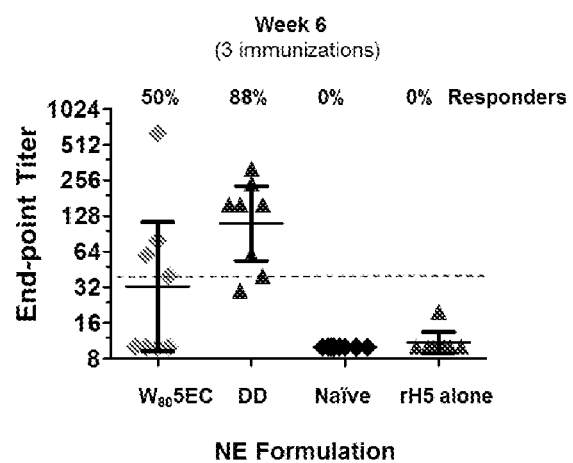

The DODAC formulation (DD) stimulated a more rapid rH5-specific IgG antibody response (Week 4) (See FIG. 4-A) and higher "functional" HAI antibody responses at Week 6 (See FIG. 4-B) compared to W805EC. The DODAC formulation stimulated a geometric mean HAI titer of 1:111 (7/8 animals ≥1:40) compared to only 1:32 for W805EC (4/8 animals ≥1:40). A cut-off for geometric mean titer (GMT) of ≥1:40 for HAI is accepted as a correlate of protection for influenza.

Figure 5:
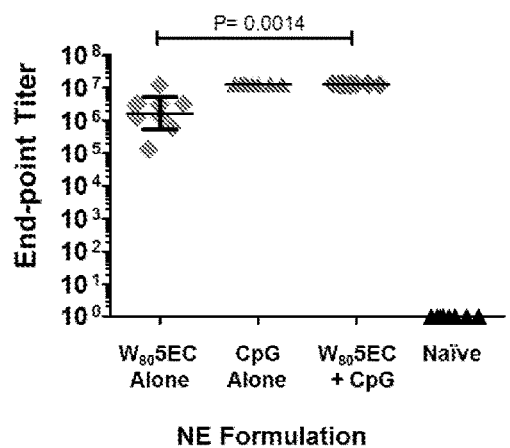
FIG. 5 shows serum rH5-specific antibody responses after intramuscular immunization of CD-1 mice using W805EC alone or in combination with CpG oligodeoxynucleotide (ODN) 1826. (A) 5% W805EC in combination with 20 μg CpG ODN and 10 μg rH5 antigen stimulated high levels (GMT>$10^7$) of rH5-specific IgG in serum after 3 immunizations (Week 6). (B) The combination of W805EC+CpG also activated the highest levels of "functional" HAI antibody (GMT: 160; 75% responders) when compared to W805EC alone (GMT: 32; 50% responders), or CpG alone (GMT: 77; 50% responders).
Figure 5:
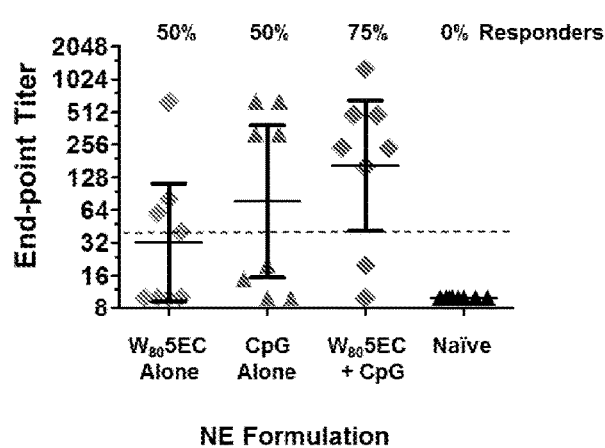

An adjuvant formulation comprising W805EC nanoemulsion together with CpG ODN 1826, a TLR9 agonist, was also evaluated. CD-1 mice were immunized IM at 2 week intervals using nanoemulsion plus 10 µg rH5 antigen. As shown in FIG. 5, 5% W805EC in combination with 20 µg CpG ODN and 10 µg rH5 antigen stimulated high levels (GMT>$10^7$) of rH5-specific IgG in serum after 3 immunizations (Week 6)(See FIG. 5A). The combination of W805EC+CpG also activated the highest levels of "functional" HAI antibody (GMT: 160; 75% responders) when compared to W805EC alone (GMT: 32; 50% responders), or CpG alone (GMT: 77; 50% responders)(See FIG. 5B).

Figure 6:
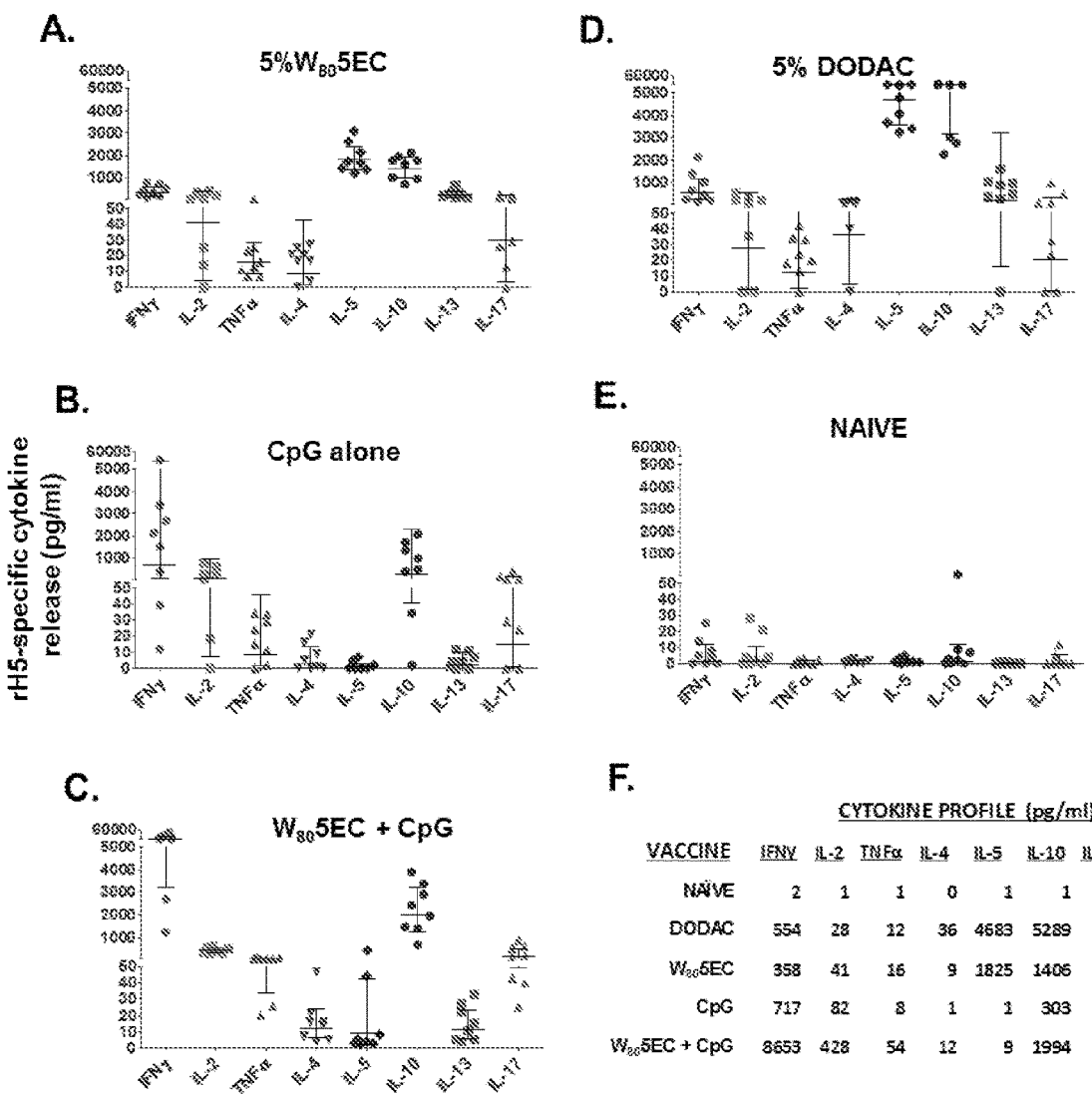
FIG. 6 shows the profile of cell-mediated immune responses measured by cytokine release upon rH5 antigen re-stimulation of spleen cells obtained after intramuscular immunization using nanoemulsion+CpG ODN combination vaccines.

The profile of cell-mediated immunity (Th1, Th2, and Th17) was determined by cytokines secretion analysis upon rH5 antigen re-stimulation of spleen cells obtained at the time of sacrifice on week 6 from mice immunized intramuscularly using the new nanoemulsion-formulations (See FIG. 6). Surprisingly, W805EC nanoemulsion in combination with CpG synergistically increased Th1 and Th17 responses while at the same time reducing or "shifting" the cellular response away from Th2 responses with concurrent retention of IL-10 to provide anti-inflammatory activity (See FIG. 6).

Overall, the combination of $W_{80}5EC$+CpG activated a distinct profile characterized by strikingly greater production of Th1 cytokines (IFNγ, IL-2 and TNFα) when compared to either W805EC or CpG alone (FIG. 6 A-C).

Figure 7:
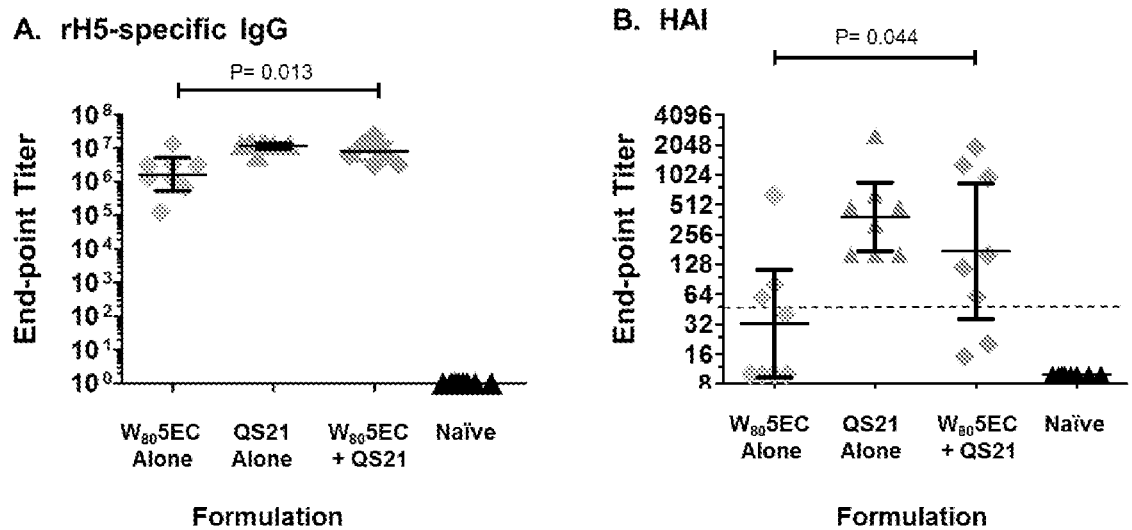
FIG. 7 shows serum rH5-specific antibody responses after intramuscular immunization of CD-1 mice using W805EC alone or in combination with QS21.
Figure 8:
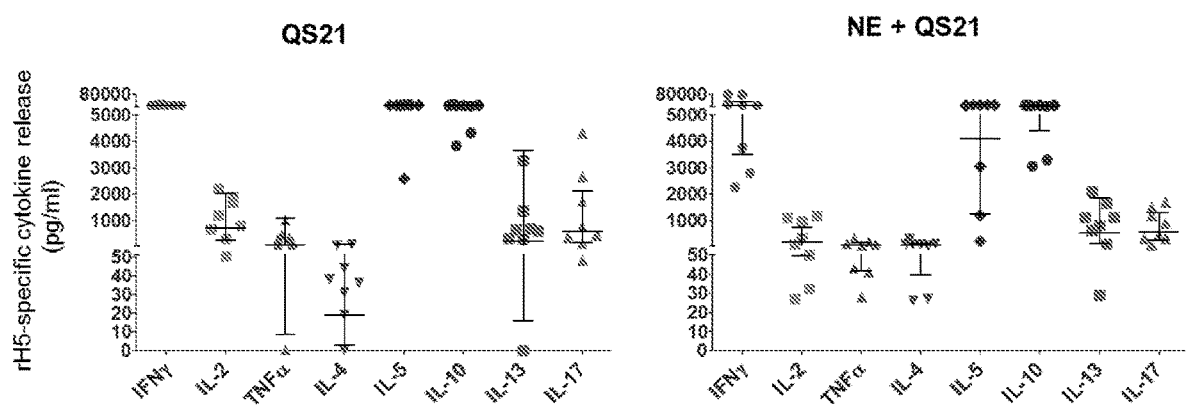
FIG. 8 shows the profile of cell-mediated immune responses stimulated by nanoemulsion+QS21 combination vaccines when administered by the intramuscular route in CD-1 mice.

In contrast to CpG ODN, addition of QS21 to the W805EC nanoemulsion formulation did not enhance serum rH5-specific IgG (See FIG. 7A), HAI antibody responses (SEE FIG. 7B) or cell-mediated immune responses (cytokine profile) (See FIG. 7) when compared to QS21 alone at a dose of 10 µg. QS21 stimulated high levels of HAI antibody (GMT 1:386) together with a strong and balanced Th1 plus Th2 cytokine profile (See FIG. 8).

Additional adjuvant formulations were formulated (See Table 9, below), administered via an intramuscular route of administration and analyzed for production of "functional" HAI and VN antibodies. Formulations are shown in Table 9 below using a combination of 5% $W_{80}5EC$ or 5% DODAC NE adjuvant together with immune modulators CpG at varying doses as shown in Table 9 and FIG. 8.

TABLE 9

Evaluation of $W_{80}5EC$ adjuvant in combination with QS21 or CpG ODN, or using nanoemulsions formulated with DODAC cationic surfactant by the intramuscular route in CD-1 mice.

| Group | Description | Amount of rH5 per each Immunization (µg per 50 µL dose) | Adjuvant System Concentration or Amount (µg) per 50 µL IM dose |
|---|---|---|---|
| 1 | 5% $W_{80}5EC$ | 10 | CpG (20 µg) |
| 2 | 5% DODAC NE + CpG | 10 | CpG (20 µg) |
| 3 | 5% DODAC NE | 10 | — |
| 4 | CpG | 10 | CpG (20 µg) |
| 5 | 5% DODAC NE + CpG | 10 | CpG (10 µg) |
| 6 | CpG | 10 | CpG (10 µg) |
| 7 | 5% DODAC NE + CpG | 10 | CpG (5 µg) |
| 8 | CpG | 10 | CpG (5 µg) |
| 9 | 5% DODAC NE + CpG | 5 | CpG (10 µg) |
| 10 | CpG | 5 | CpG (10 µg) |

Figure 10:
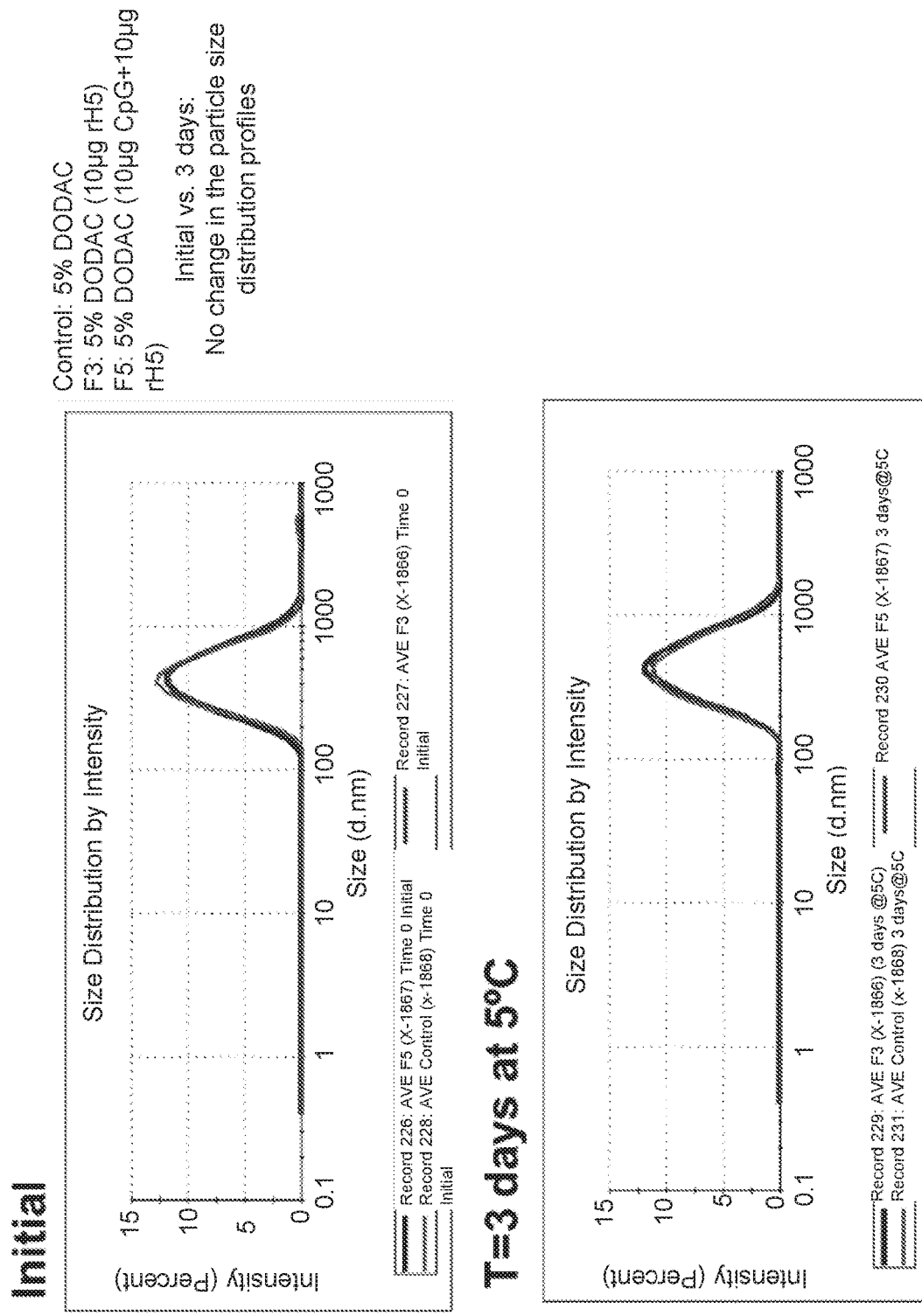
FIG. 10 shows the particle size distribution for NE+CpG ODN combination vaccines after storage at 5° C.
Figure 11:
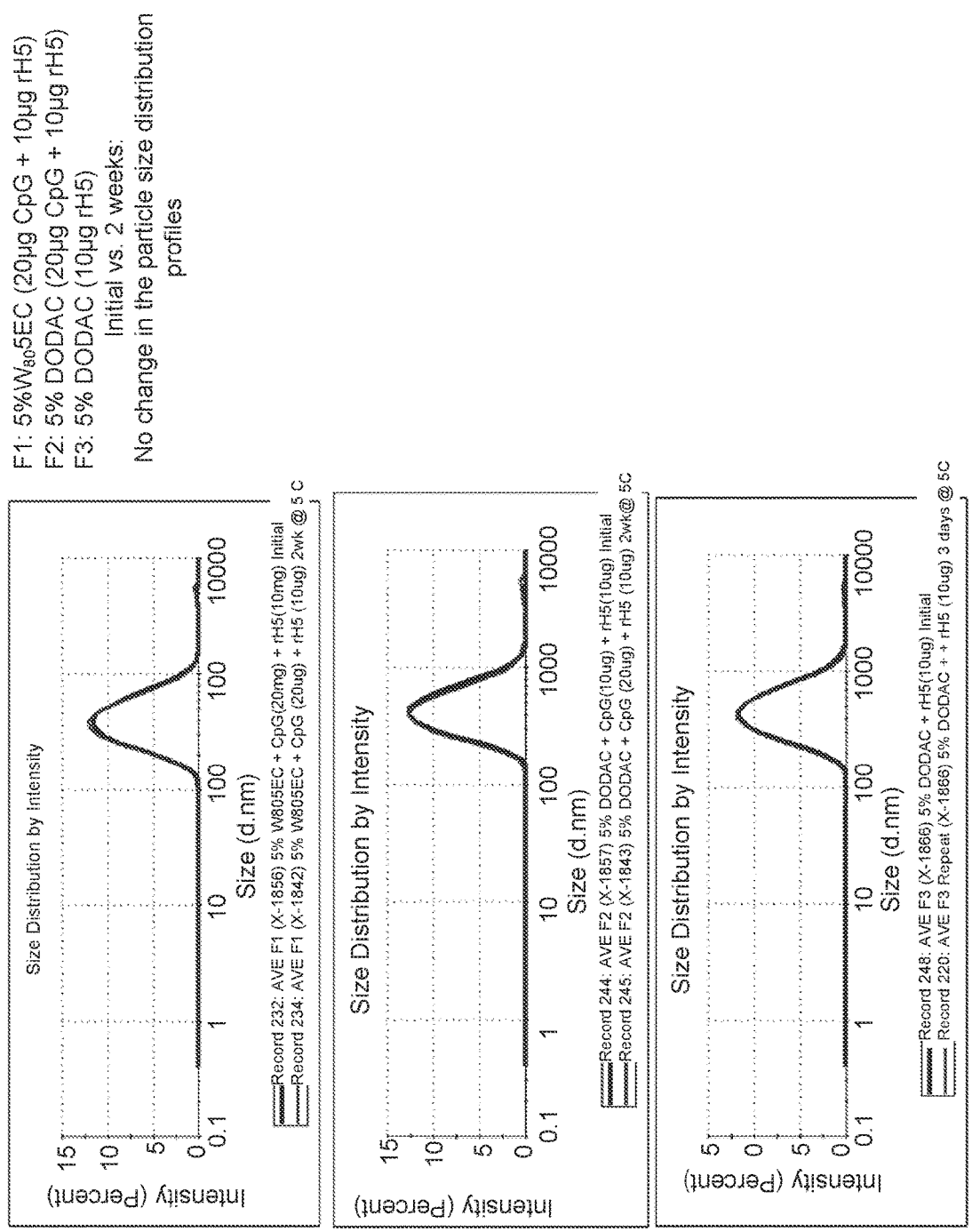
FIG. 11 shows the particle size distribution for NE+CpG ODN combination vaccines after storage at 5° C.
Figure 12:
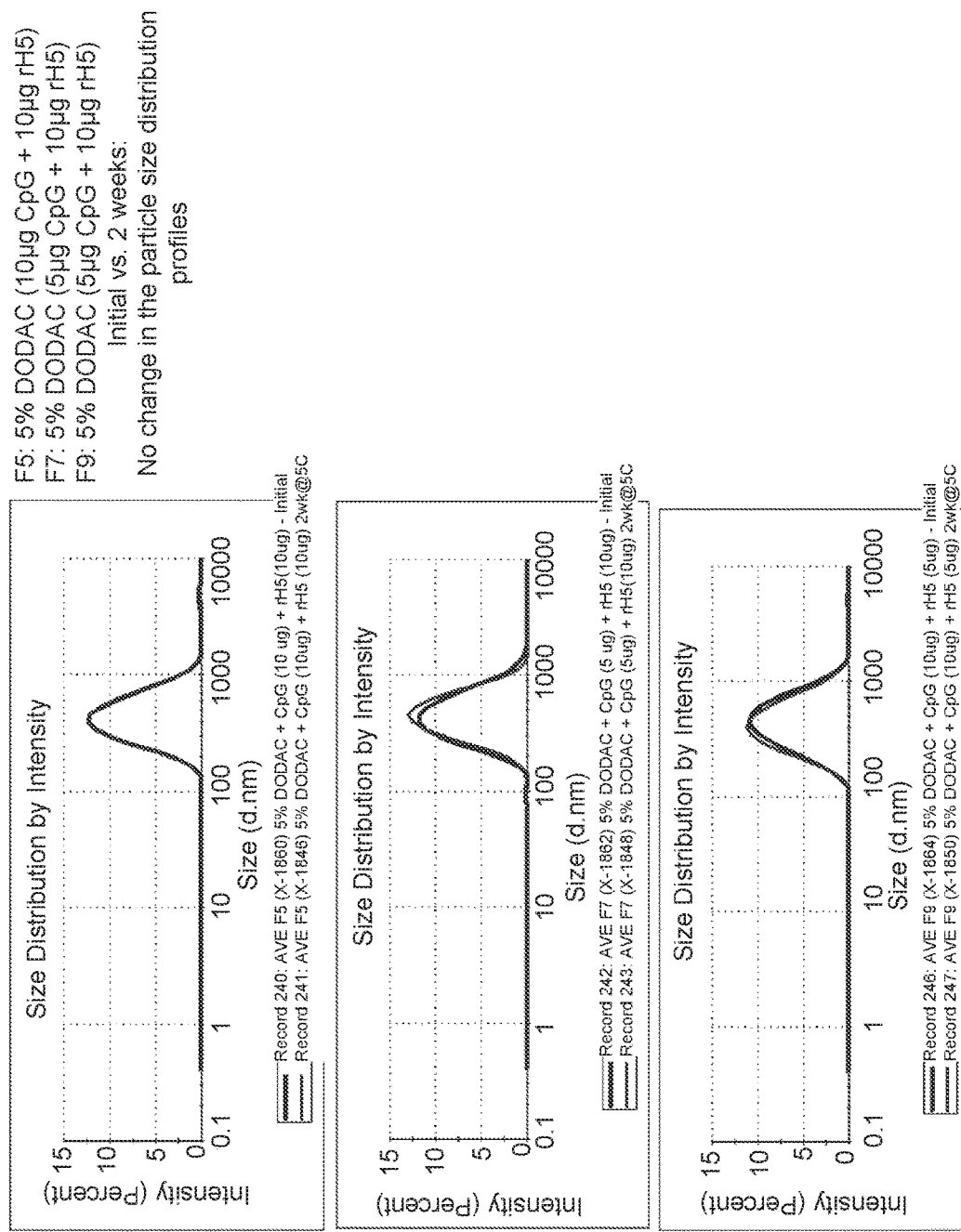
FIG. 12 shows the particle size distribution for NE+CpG ODN combination vaccines after storage at 5° C.

Single-radial immunodiffusion (SRID) analysis. This procedure was used to assess the antigen stability of nanoemulsion adjuvanted rH5 vaccines. The haemagluttinin (HA) concentration of stored vaccines was evaluated by SRID analysis with comparison to an rH5 antigen control in which the HA concentration is known. Briefly, 1% agarose is prepared using 1×PBS, pH 7.2. The anti-HA antibodies are added to the agarose and gently transferred to a gel bond using a sterile pipette. The analysis utilized sheep anti-rH5 (lot CRP 13-02-G765) developed at Fraunhofer USA Center for Molecular Biotechnology (FhCMB). The reference and test vaccines are diluted in PBS to achieve a range of rH5 concentrations as shown in FIG. 13. After solidification, 4 mm wells are prepared using a gel punch and 20 µl of the appropriate vaccine dilution is added to each well. The plates are incubated in a sealed humidity chamber at room temperature for 18-24 hours. After incubation, plates are submerged in sterile saline (20 minutes), rinsed for 10 minutes in purified water, dried on filter paper (2-6 hours), stained for 7-10 minutes, and destained for 4-5 minutes. Gel images are scanned and stored as a digital image for subsequent measurement of ring diameter in two dimensions. rH5 concentration is calculated based on orthogonal measurements of the diameters for each duplicate well and the dilution factors for both the reference and the samples using an Excel SRID Trivalent Calculation Spreadsheet as determined by the parallel line assay method. Stability Results of Appearance, pH, Particle Size Analysis, Polydispersity Index (PdI) of NE adjuvant stability and formulation of combination vaccines. The stability of NE+CpG ODN vaccines (See Table 10, below) was assessed based on physical-chemical parameters after storage for 3 days or 14 days at 5° C. (See Tables 10-11, and FIGS. 10-12). In addition, as shown in FIG. 13, evaluation of rH5 antigen in vaccine formulations designated 1-4, (Table 9) by single-radial immuno-diffusion analysis (SRID) demonstrated that there was no loss of antigen immunoreactivity or concentration (rH5 concentration of 200 µg/ml) after storage of the vaccines for 3-14 days at 5° C.

Thus, the invention provides adjuvant formulations that display excellent short-term nanoemulsion stability and compatibility with CpG ODN as required for extemporaneous preparation of the vaccines.

TABLE 10

Control formulations compared to the test formulations with rH5 and CpG in a buffered solution.

| Lot # | | Lot # | Storage Condition | Appearance | pH |
|---|---|---|---|---|---|
| Nanoemulsion Adjuvant | 60% DODAC/Tween 80 | X-1776B | 5° C. | Pass | 5.045 |
| Antigen Control | rH5 | Eng. Lot | −70° C. | Pass | 7.314 |
| Adjuvant Control | CpG | Adjuvant | −70° C. | Pass | 6.274 |
| F 4 | CpG (20 µg) + rH5 (10 µg) | X-1859 | Initial | Pass | 7.435 |
| | | X-1845 | 14 days@ 5° C. | Pass | 7.576 |
| F 6 | CpG (10 µg) + rH5 (10 µg) | X-1861 | Initial | Pass | 7.528 |
| | | X-1847 | 14 days @ 5° C. | Pass | 7.714 |
| F 8 | CpG (5 µg) + rH5 (10 µg) | X-1863 | Initial | Pass | 7.512 |
| | | X-1849 | 14 days@ 5° C. | Pass | 7.697 |
| F 10 | CpG (10 µg) + rH5 (5 µg) | X-1865 | Initial | Pass | 7.531 |
| | | X-1851 | 14 days@ 5° C. | Pass | 7.705 |

TABLE 11

Evaluation of appearance, pH, particle size and zeta potential of NE + CpG ODN combination vaccines after storage at 5° C.

| Lot # | | Lot # | Storage Condition | Appearance | pH | Particle Size (nm) | PdI |
|---|---|---|---|---|---|---|---|
| DPI | 60% DODAC in Water | X-1776B | (5° C.) | Pass | 5.045 | 414.7 ± 2.1 | 0.160 ± 0.021 |
| Control | Control: 5% DODAC in PBS (no rH5, No CpG) | X-1868 | Initial | Pass | 7.444 | 405.0 ± 4.1 | 0.178 ± 0.017 |
| | | X-1868 | 3 days @ 5° C. | Pass | 7.515 | 391.4+ 6.3 | 0.175 ± 0.005 |
| | | TBD | 14 days @ 5° C. | | | | |

TABLE 11-continued

Evaluation of appearance, pH, particle size and zeta potential of NE + CpG ODN combination vaccines after storage at 5° C.

| Lot # | | Lot # | Storage Condition | Appearance | pH | Particle Size (nm) | PdI |
|---|---|---|---|---|---|---|---|
| F 1 | 5% W$_{80}$5EC + CpG (20 μg) + rH5 (10 μg) | X-1856 X-1842 | Initial 14 days @ 5° C. | Pass Pass | 7.462 7.500 | 369.9 ± .3 369.1 ± 3.0 | 0.186 ± 0.007 0.175 ± 0.042 |
| F 2 | 5% DODAC + CpG (20 μg) + rH5 (10 μg) | X-1857 X-1843 | Initial 14 days @ 5° C. | Pass Pass | 7.395 7.388 | 411.2 ± 5.0 394.7 ± .6 | 0.153 ± 0.020 0.189 ± 0.036 |
| F 3 | % DODAC + rH5 (10 μg) | X-1866 X-1866 TBD | Initial 3 days @ 5° C. 14 days @ 5° C. | Pass Pass — | 7.416 7.492 — | 416.9 ± 5.3 395.9 ± 3.7 — | 0.173 ± 0.028 0.159 ± 0.013 — |
| F 5 | 5% DODAC + CpG (10 μg) + rH5 (10 μg) | X-1860 X-1846 | Initial 14 days @ 5° C. | Pass Pass | 7.486 7.553 | 397.2 ± 6.9 397.1 ± 4.1 | 0.175 ± 0.022 0.171 ± 0.028 |
| F 7 | 5% DODAC + CpG (5 μg) + rH5 (10 μg) | X-1862 X-1848 | Initial 14 days @ 5° C. | Pass Pass | 7.535 7.731 | 401.3 ± 1.5 400.4 ± 1.9 | 0.168 ± 0.008 0.158 ± 0.005 |
| F 9 | 5% DODAC + CpG (10 μg) + rH5 (5 μg) | X-1864 X-1850 | Initial 14 days @ 5° C. | Pass Pass | 7.500 7.629 | 398.1 ± 7.7 386.6 ± 1.0 | 0.177 ± 0.005 0.189 ± 0.013 |

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. A method of generating an immune response in a subject comprising administering to the subject an immunogenic composition comprising:
   (a) one or more antigens;
   (b) a nanoemulsion adjuvant which comprises oil, water, an organic solvent, a cationic surfactant, and a nonionic surfactant;
   and (c) at least one immunostimulatory compound selected from a toll-like receptor antagonist and a triterpene glycoside saponin.

2. The method of claim 1, wherein the immune response is greater than the immune response generated in a subject administered a composition containing the one or more antigens and only the nanoemulsion adjuvant, and/or is greater than the immune response generated in a subject administered a composition containing the one or more antigens and only the immunostimulatory compound.

3. The method of claim 1, wherein the toll-like receptor antagonist is a synthetic oligodeoxynucleotide (ODN); a polyinosinic-polycytidylic acid (poly (IC); monophosphoryl lipid A; (MPL); flagellin; imiquimod; a multi-pattern recognition receptor (multi-PRR ligand); a RIG-I-like receptor agonist; NOD or a NOD-like receptor ligand agonist; an inflammasome inducer; a cytosolic DNA sensor (CDS); a STING ligand; an immune cell receptor; a cytokine; a chemokine; a synthetic glycolipid; or a vitamin.

4. The method of claim 1, wherein the one or more antigens are selected from an inactivated microbial pathogen, an isolated and/or recombinant peptide, an isolated and/or recombinant protein, a glycoprotein, a lipoprotein, a glycopeptide, a lipopeptide, a toxoid, a carbohydrate, and a tumor-specific antigen.

* * * * *